US006251397B1

(12) United States Patent
Paul et al.

(10) Patent No.: US 6,251,397 B1
(45) Date of Patent: *Jun. 26, 2001

(54) PROTEINS ENCODED BY POLYNUCLEIC ACIDS ISOLATED FROM A PORCINE REPRODUCTIVE AND RESPIRATORY SYNDROME VIRUS AND IMMUNOGENIC COMPOSITIONS CONTAINING THE SAME

(75) Inventors: Prem S. Paul; Xiang-Jin Meng; Patrick Halbur; Igor Morozov, all of Ames, IA (US)

(73) Assignees: Iowa State University Research Foundation, Inc., Ames, IA (US); American Cyanamid Company, Madison, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/478,316

(22) Filed: Jun. 7, 1995

Related U.S. Application Data

(63) Continuation-in-part of application No. 08/301,435, filed on Sep. 1, 1994, which is a continuation-in-part of application No. 08/131,625, filed on Oct. 5, 1993, now Pat. No. 5,695,766, which is a continuation-in-part of application No. 07/969,071, filed on Oct. 30, 1992, now abandoned.

(51) Int. Cl.[7] .................................................... A61K 39/12

(52) U.S. Cl. ...................................... 424/186.1; 424/204.1; 424/218.1; 530/350

(58) Field of Search ............................. 424/139.1, 147.1, 424/159.1, 186.1, 199.1, 204.1, 209.1, 235.1, 218.1; 435/69.1, 69.3, 172.3, 173.3, 320.1; 530/388.3, 350; 536/23.72

(56) References Cited

U.S. PATENT DOCUMENTS

| 5,476,778 | 12/1995 | Chladek et al. ........................ 3/199.4 |
| 5,695,766 | * 12/1997 | Paul et al. .......................... 424/204.1 |

FOREIGN PATENT DOCUMENTS

| 0595436 | 5/1994 | (EP) . |
| 2282811 | 4/1995 | (GB) . |
| WO 92/21375 | 12/1992 | (WO) . |
| WO 93/03760 | * 3/1993 | (WO) ............................. A61K/39/00 |
| 93/07898 | 4/1993 | (WO) . |

OTHER PUBLICATIONS

Conzelmann et al. "Molecular Characterization of Porcine Reproductive and Respiratory Syndrome Virus, a Member of the Arterivirus Group". Virology. vol. 193:329–339, 1993.*

Collins et al. "Isolation of swine infertility and respiratory syndrome virus (isolate ATCC VR–2332) in North America and experimental reproduction of the disease in gnotobiotic pigs". J. Vet. Diagn. Invest. vol. 4:117–126, 1992.*

Hill et al. "Prevalence of SIRS In Iowa Swine Herds". Am. Assoc. Swine Practitioner Newsletter. vol. 4:47, 1992.*

Compiled by Sherwood et al. "International reports of PRRS Status and Control:1992". PDIC. pp. 1–58, 1992.*

Ellis et al. "New Technologies for Making Vaccines". Vaccines. Plotkin et al., Eds. W.B. Saunders. Chapter 29:568–575, 1988.*

Morozove, et al, "Sequence Analysis of Open Reading Frames (ORFs) 2 to 4 of a U.S. Isolate of Porcine Reproductive and Respiratory Syndrome Virus", Arch. Virology, 1995, vol. 140, pp. 1313–1319.

Nelson et al, "Differential of U.S. and European Isolate of Porcine Reproductive and Respiratory Syndrome Virus by Monoclonal Antibodies" Journal of Clinical Microbiology, Dec. 1993, vol. 31, No. 12, pp. 3184–3189.

Goyal, S.M., "Porcine Reproductive and Respiratory Syndrome", J. Vet. Diagn. Invest., 1993, vol. 5, pp. 656, 664.

Domingo et al, "New Observations on Antigenic Diversification of RNA Viruses. Antigenic Variation is Not Dependent on Immune Selection", Journal of General Virology, 1993, vol. 74, pp. 2039–2045.

Wensvoort et al, *Vet. Quarterly*, 13:121–130 (1991).

Christianson et al, *Can. J. Vet. Res.*, 53:485–488 (1992).

Meulenberg et al, *Virology*, 192:62–72 (1993).

Meulenberg et al, *J. Gen. Virol.*, 74:1697–1701 (1993).

Wensvoort et al, *J. Vet. Diagn. Invest.*, 4:134–138 (1992).

Plagemann and Moennig, *Adv. Virus Res.*, 41:99–192 (1992).

Godeny et al, *Virology*, 194:585–596 (1993).

Mardassi et al, *J. Gen. Virol.*, 75:681–685 (1994).

(List continued on next page.)

Primary Examiner—Donna C. Wortman
(74) Attorney, Agent, or Firm—Oblon, Spivak, McClelland, Maier & Neustadt, P.C.

(57) ABSTRACT

The present invention provides a purified preparation containing, for example, a polynucleic acid encoding at least one polypeptide selected from the group consisting of proteins encoded by one or more open reading frames (ORF's) of an Iowa strain of porcine reproductive and respiratory syndrome virus (PRRSV), antigenic regions of such proteins which are at least 5 amino acids in length and which effectively protect a porcine host against a subsequent challenge with a PRRSV isolate, and combinations thereof in which amino acids non-essential for antigenicity may be conservatively substituted. The present invention also concerns a polypeptide encoded by such a polynucleic acid; a vaccine comprising an effective amount of such a polynucleic acid or protein; antibodies which specifically bind to such a polynucleic acid or protein; methods of producing the same; and methods of protecting a pig against a PRRSV and treating a pig infected by a PRRSV.

9 Claims, 21 Drawing Sheets

OTHER PUBLICATIONS

Chen et al, *J. Gen. Virol.*, 74:643–660 (1993).
den Boon et al, *J. Virol.*, 65:2910–2920 (1990).
de Vries et al, *Nucleic Acids Res.*, 18:3241–3247 (1990).
Kuo et al., *J. Virol.*, 65:5118–5123 (1991).
Kuo et al, *Vir. Res.*, 23:55–72 (1992).
Meulenberg et al, *Virology*, 206:155–163 (1995).
de Vries et al, *J. Virol.*, 66:6294:6303 (1992).
Faaberg et al, *J. Virol.*, 69:613–617 (1995).
Cafruny et al, *Vir. Res.*, 5:357–375 (1986).
Meng et al, *J. Vet. Diagn. Invest.*, 5:254–258 (1993).

* cited by examiner

```
                                              +1>ORF2
VR2385   CCTGTCATTGAACCAACTTTAGGCCTGAATTGAGATGAAATGGGGTCTATGCAAAGCCTT   60
ISU3927  ...A.............G..T..AG.C...A...C..........C............   60
ISU55    ...A...........................A..........................   60
ISU22    ...............................A...............G.C........   60
VR2332   ...............................A.................C........   60
ISU1894  ..C............................A.................CG........  60
ISU79    ...............................A.................C........   60

VR2385   TTTGACAAAATTGGCCAACTTTTTGTGGATGCTTTCACGGAGTTCTTGGTGTCCATTGTT  120
ISU3927  .......G..C..T..............................................  120
ISU55    ........................C...................................  120
ISU22    .............................................................  120
VR2332   .............................................................  120
ISU1894  .............................................................  120
ISU79    .............................................................  120

VR2385   GATATCATTATATTTTTGGCCATTTTGTTTGGCTTCACCATCGCAGGTTGGCTGGTGGTC  180
ISU2927  .......C..............................T..C..C..............  180
ISU55    ...................................................C........  180
ISU22    ...................................................C........  180
VR2332   ...................................................C........  180
ISU1894  .......C...........................................C........  180
ISU79    ............C......................................C........  180

VR2385   TTTTGCATCAGATTGGTTTGCTCCGCGATACTCCGTGCGCGCCCTGCCATTCACTCTGAG  240
ISU3297  ...........................................................C.....  240
ISU55    ..........................C..................................  240
ISU22    ...............................................................  240
VR2332   ...................................A..........................  240
ISU1894  ...................................A..........................  240
ISU79    ...................................A..........................  240

VR2385   CAATTACAGAAGATCCTATGAGGCCTTTCTCTCTCAGTGCCAGGTGGACATTCCCACCTG  300
ISU3297  ..........................T..............................G....  300
ISU55    ..........................T...................................  300
ISU22    ..........................T......T..C........A.................  300
VR2332   ..........................T......T..C........A.................  300
ISU1894  ..........................T......T.A.C........A.................  300
ISU79    ..........................T......T..C........A.................  300

VR2385   GGGAACTAAACATCCTTTGGGGATGCTTTGGCACCATAAGGTGTCAACCCTGATTGATGA  360
ISU3927  .....A.G........A.............C.................................  360
ISU55    .....T........................T..................................  360
ISU22    ..............................T.G................................  360
VR2332   ..................................................................  360
ISU1894  ..............................T...................................  360
ISU79    ..............................T...................................  360
```

FIG.1A

```
VR2385    AATGGTGTCGCGTCGAATGTACCGCATCATGGAAAAAGCAGGACAGGCTGCCTGGAAACA    420
ISU3927   ............................................................    420
ISU55     ............................................................    420
ISU22     .....................................G......................    420
VR2332    .....................................G......................    420
ISU1894   ............C........................G......................    420
ISU79     G...........................................................    420

VR2385    GGTAGTGAGCGAGGCTACGCTGTCTCGCATTAGTAGTTTGGATGTGGTGGCTCATTTTCA    480
ISU3927   ...G.....T..........................G..................C....    480
ISU55     ...G....................................................C....    480
ISU22     ...G..........................................................    480
VR2332    ...G..........................................................    480
ISU1894   ...G..................C.......................................    480
ISU79     ...G..........................................................    480

VR2385    GCATCTTGCCGCCATTGAAGCCGAGACCTGTAAATATCTGGCCTCTCGGCTGCCCATGCT    540
ISU3927   ...C.........................T.........T.............T.......    540
ISU55     .............................T................................    540
ISU22     ........T....................T..................C.............    540
VR2332    .....A.........................................T..........C...    540
ISU1894   .............................T.........T..................C...    540
ISU79     .............C.............................T.............C....    540
                                                  -89(mRNA3)
VR2385    ACACCACCTGCGCATGACAGGGTCAAATGTAACCATAGTGTATAATAGTACTTTGAATCA    600
ISU3927   ....A.......T..T........................C.....................    600
ISU55     ....A...........................................................   600
ISU22     ....A...........................................................   600
VR2332    ....A..........................................C................   600
ISU1894   ...TA........A...................................C.G.G..         600
ISU79     ....A...........................................................G  600
                                                                        +1>
VR2385    GGTGTTTGCTGTTTTCCCAACCCCTGGTTCCCGGCCAAAGCTTCATGATTTCCAGCAATG    660
ISU3927   ..........A......C....T.........C........T...................    660
ISU55     ....C.....A...................................T...............    660
ISU22     ..........A...................................T...............    660
VR2332    ..........A....T..............................T...............    660
ISU1894   ..........A...................................T...............    660
ISU79     ..........A.............................................C..T...   660
          ORF3
VR2385    GCTAATAGCTGTACATTCCTCTATATTTTCCTCTGTTGCAGCTTCTTGTACTCTTTTTGT    720
ISU3927   ....................C....CC..................................    720
ISU55     ..............................................................    720
ISU22     .T.................C...........................C.............    720
VR2332    .T.................C...........................................  720
ISU1894   .T.................C...........................................  720
ISU79     ............G......C....................................C.....   720
```

FIG. 1B

```
VR2385    TGTGCTGTGGTTGCGGGTTCCAATGCTACGTACTGTTTTTGGTTTCCGCTGGTTAGGGGC    780
ISU3927   ....T......A...A.G............T.............................    780
ISU55     ...........................T..C.............................    780
VR2385    ............................................................    780
ISU22     ........................A.....T.............................    780
VR2332    ........................A...................................    780
ISU1894   .......C...................................................G    780
ISU79     ........................A...................................    780
                                          **<ORF2
VR2385    AATTTTTCTTTCGAACTCACGGTGAATTACACGGTGTGCCCGCCTTGCCTCACCCGGCAA    840
ISU3927   ........C....G....T.................A......................G    840
ISU55     ..............A.....C................T..A...................    840
VR2385    ............................................................    840
ISU22     ............G........................T..A...................    840
VR2332    ..............A......................T..A...................    840
ISU1894   .......C....T........................T..A...................    840
ISU79     ..............TA.....................A......................    840
                                ***
VR2385    GCAGCCGCAGAGGCCTACGAACCCGGCAGGTCCCTTTGGTGCAGGATAGGGCATGATCGA    900
ISU3927   ........C..AT........AA.....T............C...A..............    900
ISU55     .....A..............T.....T.........................T......C    900
ISU22     ...........AT.......T.....T.........................T....C..    900
VR2332    .....A.....AT.......T.....T.........................T....C..    900
ISU1894   ..........T.........T.....T.........................T....C..    900
ISU79     ....................T.....T.........................T.C.....    900

VR2385    TGTGGGGAGGACGATCATGATGAACTAGGGTTTGTGGTGCCGTCTGGCCTCTCCAGCGAA    960
ISU3927   .....T.........C..C........A...ACA..A...C.............AA...    960
ISU55     ...............C............................................    960
ISU22     ...............C..G........A...A..AC....T...................    960
VR2332    ...............C.G.........A..A..C..........................    960
ISU1894   ...............C..G........A..A..C..........................    960
ISU79     .....A......C....C.G........A..A.A...........................    960
              -236(mRNA3-1)
VR2385    GGCCACTTGACCAGTGCTTACGCCTGGTTGGCGTCCCTGTCCTTCAGCTATACGGCCCAG    1020
ISU3927   .T...T........T.............TT...........T..C...............    1020
ISU55     ........_____.T.....................T.......T..C..A.........    1020
ISU22     .......T....T............TTT.................C..............    1020
VR2332    ........TG...T...........T.T.................C..............    1020
ISU1894   .........T...T...........TTT.................C..............    1020
ISU79     ........_____.T..........T.T.................C..............    1020
                                                        +1>ORF4-1
VR2385    TTCCATCCCGAGATATTCGGGATAGGGAATGTGAGTCGAGTCTATGTTGACATCAAGCAC    1080
ISU3927   ..T..............A........AAG.............___...........T..T    1080
ISU55     ....T....................A....T....___..........G...T       1080
ISU22     ........................C......T...___..............A..T    1080
VR2332    ................................T...___..............A..T    1080
ISU1894   ................................T...___..............A..T    1080
ISU79     .......C........................T...___..............A..T    1080
```

FIG. 1C

```
VR2385   CAATTCATTTGCGCTGTTCATGATGGGCAGAACACCACCTTGCCCCACCATGACAACATT  1140
ISU3927  ...C......T.......C...................T.G............  1140
ISU55    ..........C.....C..C........G...T.....T.G.........T...  1140
ISU22    ...C....C.....C.AA.....C....A.........T.GT............  1140
VR2332   ...C....C.....C.AA.....C..............T.GT............  1140
ISU1894  ...C..........C.AA.....C..A.....G.....T.GT........T...  1140
ISU79    ...C....C.....C.AA.....C..............T.GT............  1140
                                                         -10(mRNA4)
VR2385   TCAGCCGTGCTTCAGACCTATTACCAGCATCAGGTCGACGGGGGCAATTGGTTTCACCTA  1200
ISU3927  ..T.....T..........A..C..A.....T..T.....C..._____...  1200
ISU55    ........T.C.....T.....A.....A........C..._____...  1200
ISU22    ........T.............A.....A........T..._____...  1200
VR2332   ........T.............A.....A........C..._____...  1200
ISU1894  ........T.............A.....A........T..C..._____...  1200
ISU79    ..G.....T.............A.....A........C..._____...  1200
         +1>ORF4                                              **
VR2385   GAATGGGTGCGTCCCTTCTTTTCCTCTTGGTTGGTTTTAAATGTCTCTTGGTTTCTCAGG  1260
ISU3927  ......C.................................G......C.........  1260
ISU55    ......C...................................................  1260
ISU22    ......C.T.......................A.........................  1260
VR2332   ......C.T...............................G.................  1260
ISU1894  ......C.T.......................A.................A.......  1260
ISU79    ......C.........................A.........................  1260
         *<ORF3-1
VR2385   CGTTCGCCTGCAAGCCATGTTTCAGTTCGAGTCTTTCAGACATCAAGACCAACACCACCG  1320
ISU3927  ............................................................  1320
ISU55    ...............................G.......T.................  1320
ISU22    ..............A................G....T..T..................  1320
VR2332   ..............A................G....T..T..................  1320
ISU1894  ..............A.....C..........G....T..T.............T....  1320
ISU79    ..............A................G.......T..................  1320

VR2385   CAGCGGCAGGCTTTGCTGTCCTCCAAGACATCAGTTGCCTTAGGCATCGCAACTCGGCCT  1380
ISU3927  .G..A...AAT..C.......G.....G.C............G......A..A  1380
ISU55    .........................................T...............  1380
ISU22    ........A...............G.................G...............  1380
VR2332   ........A.................................G...............  1380
ISU1894  ........A..................................................  1380
ISU79    ........A..................................................  1380
                                                      ***<ORF3
VR2385   CTGAGGCGATTCGCAAAGTCCCTCAGTGCCGCACGGCGATAGGGACACCCGTGTATATCA  1440
ISU3927  ........T......A............................................  1440
ISU55    ........T......A.......T..T...................A........T.  1440
ISU22    ...............A.......T...............................T.  1440
VR2332   ...............A.......T.............................G.T.  1440
ISU1894  ...............A.......T...............................T.  1440
ISU79    ...............A.......T..........................TA......T.  1440
```

FIG. 1D

```
VR2385    CTGTCACAGCCAATGTTACCGATGAGAATTATTTGCATTCCTCTGATCTTCTCATGCTTT    1500
ISU3927   ..A..........A..A........C............T....................    1500
ISU55     ..G..........A........................C....................    1500
ISU22     .CA..........G..A............A....T....C...................    1500
VR2332    .CA..........G..A............A....T....C...................    1500
ISU1894   .CA..........G..A............A....T....C...................    1500
ISU79     .CA..........G..A....A.......A....T....C........C.         1500

VR2385    CTTCTTGCCTTTTCTATGCTTCTGAGATGAGTGAAAAGGGATTTAAGGTGGTATTTGGCA    1560
ISU3927   .C............C...................G..........G.............    1560
ISU55     ..............C.................................A..........    1560
ISU22     ..................................G.........................    1560
VR2332    ............................................................    1560
ISU1894   ..............C......................A.....C...............    1560
ISU79     ..........................................G......T.........    1560

VR2385    ATGTGTCAGGCATCGTGGCAGTGTGCGTCAACTTCACCAGTTACGTCCAACATGTCAAGG    1620
ISU3927   ............C......T.....A....T..T.....C..T.........C.......    1620
ISU55     ...................T..........T.....C.......................    1620
ISU22     ...................T.....T....T..T.....C..T............G..    1620
VR2332    ...................T.....T....T..T.....C...................    1620
ISU1894   ...................T.....T....T..T.....C...............G..    1620
ISU79     ...................T.....T....T..T.....C.....T.........G..    1620

VR2385    AATTTACCCAACGTTCCTTGGTAGTTGACCATGTGCGGCTGCTCCATTTCATGACGCCCG    1680
ISU3927   .G......C.....A..G..C......................A..T.           1680
ISU55     ........C.........C........................A..T.           1680
ISU22     .G......C........G..C.............T........A..T.           1680
VR2332    .G......C..C.....G..C.............T........A..T.           1680
ISU1894   .G......C..C.....G..C.............T........A..T.           1680
ISU79     .G......C.....A..G..C......................A..T.           1680
                                                         ***<ORF4
VR2385    AGACCATGAGGTGGGCAACTGTTTTAGCCTGTCTTTTTACCATTCTGTTGGCAATTTGAA    1740
ISU3927   .A..T...........................CG..........               1740
ISU55     ..............................G.........C..                1740
ISU22     ..............................G..............              1740
VR2332    ..............................G..............              1740
ISU1894   .A............................G.........C..                1740
ISU79     ...............C..............G.T.............             1740
             +1>ORF5
VR2385    TGTTTAAGTATGTTGGGGAAATGCTTGACCGCGGGCTGTTGCTCGCAATTGCTTTTTTTA    1800
ISU3927   ...........................................G..C........G    1800
ISU55     .........................................A......TC........G    1800
ISU22     ........C................................G.........C...G    1800
VR2332    ..........A...............................G.........C...G    1800
ISU1894   ..........................................G.........C...G    1800
ISU79     ..................T......................G.........C...G    1800
```

FIG. 1E

```
VR2385   TGGTGTATCGTGCCGTCTTGTTTTGTTGCGCTCGTCAGCGCCAACGGGAACAGCGGCTCA  1860
ISU3927  ................TC...C...C...................AAC.G....---..C  1860
ISU55    ....................G.............C..........A.C.G..A.A....T  1860
ISU22    ....T...........TC.......C..T.....C........G.AAC.G....A....C  1860
VR2332   ................TC.......C..T.....C..A.....G.AACG.....A....C  1860
ISU1894  ................TC.......C..T.....C..A.....G..CC......A....C  1860
ISU79    ................TC......AC..T.....C.GA....C..A.C......A....T  1860

VR2385   AATTTACAGCTGATTTACAACTTGACGCTATGTGAGCTGAATGGCACAGATTGGCTAGCT  1920
ISU3927  C........T.......T...C............................C.....G...  1917
ISU55    C........T.......T....................................T.....  1920
ISU22    C..C........................................................  1920
VR2332   C..C........................................................  1920
ISU1894  C..C........................................................  1920
ISU79    C..C.G..AT..................................................  1920

VR2385   AATAAATTTGACTGGGCAGTGGAGTGTTTTGTCATTTTTCCTGTGTTGACTCACATTGTC  1980
ISU3927  ...........T.......A...............C.....C.................T  1977
ISU55    GG.G........................................................  1980
ISU22    ...........T.......A...............C.....C..T...............  1980
VR2332   ..C........T.......A...............C.....C..T...............  1980
ISU1894  G..........T.......A...............C.....C..T...............  1980
ISU79    G...G......T.......A.C.............C........T...............  1980

VR2385   TCTTATGGTGCCCTCACTACTAGCCATTTCCTTGACACAGTCGGTCTGGTCACTGTGTCT  2040
ISU3927  ..C........A.....C..C.............................T.........  2037
ISU55    ..C..............C..C.......................................  2040
ISU22    ..C.................C......................C.T.A............  2040
VR2332   ..C.................C......................C.T.A............  2040
ISU1894  ..C........................C...............CCT.A............  2040
ISU79    ..C.....C........C..C..................A.T.C.T.A............  2040

VR2385   ACCGCTGGGTTTGTTCACGGGCGGTATGTTCTGAGTAGCATGTACGCGGTCTGTGCCCTG  2100
ISU3927  .....C......CA...........................C..................  2097
ISU55    .....C..C...TCC..........................C..................  2100
ISU22    .....C.......................C...........C..................  2100
VR2332   .....C.......................C..A........C..................  2100
ISU1894  .....C.......................C..A........C..................  2100
ISU79    .....C.......................C..A........C..................  2100

VR2385   GCTGCGTTGATTTGCTTCGTCATTAGGCTTGCGAAGAATTGCATGTCCTGGCGCTACTCA  2160
ISU3927  ........T..................T..........C....................T  2157
ISU55    ...........................T..A.............................  2160
ISU22    ..........C.......A....C...T....A..........................G  2160
VR2332   ..........C................T....A........................G.G  2160
ISU1894  ........AGC................T....A.......................T..G  2160
ISU79    ..........C................T...T............................  2160
```

FIG.1F

```
VR2385    TGTACCAGATATACCAACTTTCTTCTGGACACTAAGGGCAGACTCTATCGTTGGCGGTCG  2220
ISU3927   ....................C.......................................A  2217
ISU55     ............................................................  2220
ISU22     ......................C.....................................  2220
VR2332    ............................................................  2220
ISU1894   .......................................................AT...  2220
ISU79     .....T.......................T..............................  2220

VR2385    CCTGTCATCATAGAGAAAAGGGGCAAAGTTGAGGTCGAAGGTCACCTGATCGACCTCAAA  2280
ISU3927   ..................G....T..G..................T..........A...  2277
ISU55     ........................T.....................T...........G  2280
ISU22     ...............................................T............  2280
VR2332    ...............................................T............  2280
ISU1894   ...............................................T............  2280
ISU79     ..................G............................T........T.....  2280

VR2385    AGAGTTGTGCTTGATGGTTCCGCGGCTACCCCTGTAACCAGAGTTTCAGCGGAACAATGG  2340
ISU3927   .A..................A.....T................................  2337
ISU55     ......................A.....A......A............G......  2340
VR2385    ............................................................  2340
ISU22     ..........................T...A......A.....................  2340
VR2332    ..........................T...A......A.....................  2340
ISU1894   .............C........T...A......A..........................  2340
ISU79     ..........................T...A......A......................  2340
                    ***<ORF5
VR2385    AGTCGTCCTTAG  2352
ISU3927   G.......C...  2349
ISU55     G...........  2352
VR2385    ............  2352
ISU22     G...........  2352
VR2332    G...........  2352
ISU1894   G...........  2352
ISU79     G...........  2352
```

FIG. 1G

```
A
VR2385    MKWGLC--K----AFLTKLAN-FLWMLSRSSWCPLLISLYFWPFCLASPSQVGWWSFASDWFAPRYSVRALPFTLSNYRRSYEAFLSQCQ    83
ISU22     .......P.-.-.-..................................P.............................................    83
ISU79     .......P.-.-.-.............S....................P.............................................    83
ISU55     .......-.-.-.-.............S....................P.............................................    83
ISU1894   ...P...-.-.-...............................................P...................................    83
ISU3927   ...Q.P.-.-.-.....RSV........S..................LPA.............................................    83
VR2332    ...P...-.-.-..............................................P....................................    83
LV        .Q..H.GV SASCSWTPS.SSLLV.LI------.PF.---.Y.G...DY...F.E....F.........P........GL.PN.R

```
B
VR2385  MANSCTFLYIFLCCSFLYSFCCAVVAGSNATYCFWFPLVRGNFSFELTVNYTVCPPCLTRQAAAEAYEPGRSLWCRIGHDRCGEDDHDEL  90
ISU55   .............................................T.............................Y...........  90
ISU79   ...A.H.......L.............T................................I...........Y...............  90
ISU1894 V...H.......................A..................V..........................Y.............  90
ISU22   V...H.................TF...................................I...........Y................  90
ISU3927 .....H.L.............V.TDA..F................M...........QI..N........N.................  90
VR2332  V...H.................T....................................T.I.........Y................  90
LV      ..HQ.ARFHF...GFIC.LVHS.LASN.SS.L......AH.T....I....I.M.S.S..RQ

FIG. 2C

```
D
VR2385    MLGKCLTAGCCSQLLFLWCIVPSCFVA--LVSANGNSGSNLQLIYNLTLCELNGTDWLANKFDWAVECFVIFPVLTHIVSYGALTTSHFL    88
VR2332    .....E......R..S......F.AV--..AN.SND.S.H...........................................S......    88
ISU55     .........Y..S........W..-..A...SSNS.H..............................GE.....................    88
ISU1894   ............R..S......F.AV--..AN.SA..S.H..........................D.....S.................    88
ISU79     ............R..S.F....F.AV--..A..SNS.S.H.................................S...........L....    88
ISU22     ........V...R..S......F.TV--..AD.HS..S.H..........................DR.....S.................    88
ISU3927   .............RS......F.L

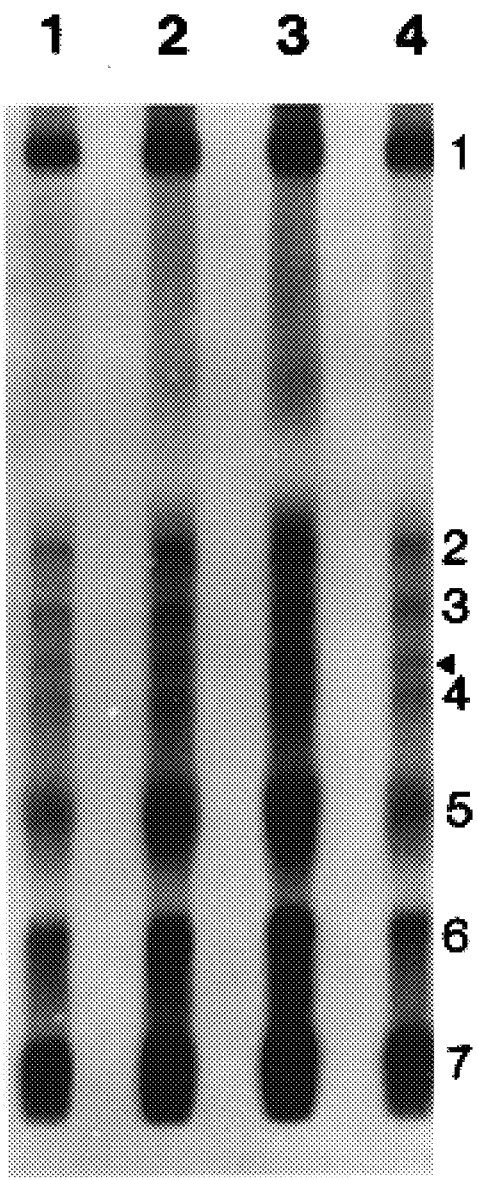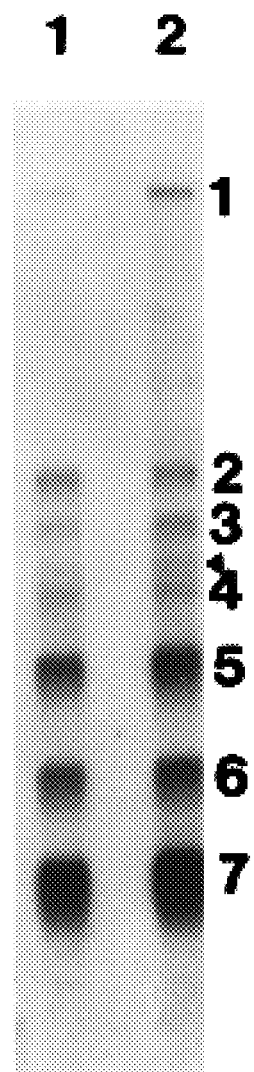
FIG.6A
FIG.6B

```
                        -89            +1>ORF3
ISU-1894-mRNA3         GUAACC...AUG
ISU-79-mRNA3           GUAACC...AUG

-236           +1>ORF4
ISU-1894               UUGACu...AUG
ISU-79-mRNA            UUGACC...AUG

-10            +1>ORF4
ISU-1894-mRNA4         UUCACC...AUG
ISU-79-mRNA4           UUCACC...AUG
```

```
                      -26 (mRNA2)              +1>ORF2
ISU79    GTTTTATTTCCCTCCGGGCCCTGTCATTGAACCAACTTTAGGCCTGAATTGAAATGAAAT  60
ISU1894  ....................C.....................................  ...

ISU79    GGGGTCCATGCAAAGCCTTTTTTGACAAAATTGGCCAACTTTTTGTGGATGCTTTCACGGA  120
ISU1894  ......G....................................................  120

ISU79    GTTCTTGGTGTCCATTGTTGATATCATTATATTCTTGGCCATTTTGTTTGGCTTCACCAT  180
ISU1894  ....C...............C.....T................................  180

ISU79    CGCCGGTTGGCTGGTGGTCTTTTGCATCAGATTGGTTTGCTCCGCGATACTCCGTACGCG  240
ISU1894  ............................................................  240

ISU79    CCCTGCCATTCACTCTGAGCAATTACAGAAGATCTTATGAGGCCTTTCTTTCCCAGTGCC  300
ISU1894  ..................................................T.A......  300

ISU79    AAGTGGACATTCCCACCTGGGGAACTAAACATCCTTTGGGGATGTTTTGGCACCATAAGG  360
ISU1894  ............................................................  360

ISU79    TGTCAACCCTGATTGATGAGATGGTGTCGCGTCGAATGTACCGCATCATGGAAAAAGCAG  420
ISU1894  ...................A............C..........................  420

ISU79    GACAGGCTGCCTGGAAACAGGTGGTGAGCGAGGCTACGCTGTCTCGCATTAGTAGTTTGG  480
ISU1894  .G...................................................C.....  480

ISU79    ATGTGGTGGCTCATTTTCAGCATCTTGCCGCCATCGAAGCCGAGACCTGTAAATATTTGG  540
ISU1894  ...............................T...........T...............  540
                                              -89(mRNA3)
ISU79    CCTCCCGGCTGCCCATGCTACACAACCTGCGCATGACAGGGTCAAATGTAACCATAGTGT  600
ISU79    .................T........A..................  ...........  600

ISU79    ATAATAGTACTTTGAATCGGGTGTTTGCTATTTTCCCAACCCCTGGTTCCCGGCCAAAGC  660
ISU1894  ............C.G.G.A.........................................  660
         +1>ORF3
ISU79    TTCATGACTTTTCAGCAATGGCTAATAGCTGTGCATTCCTCCATATTTTCCTCTGTTGCAG  720
ISU1894  .......T..........T..........A..............................  720

ISU79    CTTCTTGTACTCTCTTTGTTGTGCTGTGGTTGCGGGTTCCAATACTACGTACTGTTTTTG  780
ISU1894  .............T............C..........G.....................  780
                                                    ***<ORF2(ISU79)
ISU79    GTTTCCGCTGGTTAGGGGCAATTTTTCTTTCGAACTCATAGTGAATTACACGGTGTGCCC  840
ISU1894  ....................G........C.........G................T..  840
                                                    ***<ORF2(ISU1894)
```

FIG. 9A

```
ISU79    ACCTTGCCTCACCCGGCAAGCAGCCGCAGAGGCCTACGAACCCGGTAGGTCTCTTTGGTG 900
ISU1894  .........................T.................................. 900

ISU79    CAGGATAGGGTACGATCGATGTGGAGAGGACGACCATGACGAGCTAGGGTTTATGATACC 960
IAU1894  ............T..C........G........T.......................... 960
                              -236(ISU79 mRNA3-1)
ISU79    GTCTGGCCTCTCCAGCGAAGGCCACTTGACCAGTGTTTACGCCTGGTTGGCGTTCTTGTC1020
ISU1894  .C...................T........................T.....1020

ISU79    CTTCAGCTACACGGCCCAGTTCCACCCCGAGATATTCGGGATAGGGAATGTGAGTCGAGT1080
ISU1894  ....................T.......................................1080
            +1>ORF3-1
ISU79    TTATGTTGACATCAAACATCAACTCATCTGCGCCGAACATGACGGGCAGAACACCACCTT1140
ISU1894  ....................T..................A......G.......1140

ISU79    GCCTCGTCATGACAACATTTCGGCCGTGTTTCAGACCTATTACCAACATCAAGTCGACGG1200
ISU1894  .........T.....A....................................T..1200
                 -10(mRNA4)+1>ORF4
ISU79    CGGCAATTGGTTTCACCTAGAATGGCTGCGTCCCTTCTTTTCCTCATGGTTGGTTTTAAA1260
ISU1894  .............._____.........T................................1260
                      ***<ORF3-1
ISU79    TGTCTCTTGGTTTCTCAGGCGTTCGCCTGCAAACCATGTTTCAGTTCGAGTCTTGCAGAC1320
ISU1894  ..........A.........................C.............T1320

ISU79    ATTAAGACCAACACCACCGCAGCGGCAAGCTTTGCTGTCCTCCAAGACATCAGTTGCCTT1380
ISU1894  ................T............................................1380
                                                                  **
ISU79    AGGCATCGCAACTCGGCCTCTGAGGCGATTCGCAAAATCCCTCAGTGCCGTACGGCGATA1440
ISU1894  .............................................................1440
         *<ORF3
ISU79    GGGACACCTATGTATATTACCATCACAGCCAATGTGACAGATGAAAATTATTTACATTCT1500
ISU1894  ........CG...................G...........1500

ISU79    TCTGATCTCCTCATGCTCTCTTCTTGCCTTTTCTATGCTTCTGAGATGAGTGAAAAGGGA1560
ISU1894  ................T............C.......................A...1560

ISU79    TTTGAGGTGGTTTTTGGCAATGTGTCAGGCATCGTGGCTGTGTGTGTCAATTTTACCAGC1620
ISU1894  ..CA.......A................................................1620
                                                              -105
ISU79    TACGTTCAACATGTCAGGGAGTTTACCCAACGCTCCTTGATGGTCGACCATGTGCGGCTG1680
ISU1894  .....C..........................C..G...._____....T..1680
               -70          -55(ISU79 mRNA5)
ISU79    CTCCATTTCATGACACCTGAGACCATGAGGTGGGCAACCGTTTTAGCCTGTCTTTTTGCT1740
ISU1894  ...............A.........................T................C1740
                      -70(ISU1894 mRNA5)
```

FIG. 9B

```
                      ***<ORF4    +1>ORF5
ISU79   ATTCTGTTGGCAATTTGAATGTTTAAGTATGTTGGGGAAATGCTTGACCGTGGGCTGTTG1800
ISU1894 ......C..............................................C........1800

ISU79   CTCGCGATTGCTTTCTTTGTGGTGTATCGTGCCGTTCTGTTTTACTGTGCTCGCCGACGC1860
ISU1894 ...........................................G...........A....1860

ISU79   CCACAGCAACAGCAGCTCTCATCTGCAATTGATTTACAACTTGACGCTATGTGAGCTGAA1920
ISU1894 .AG.GC............C.....A..GC...............................1920

ISU79   TGGCACAGATTGGCTAGCTGATAGATTTGATTGGGCAGTGGAGAGCTTTGTCATCTTTCC1980
ISU1894 ...................A.......................T...............1980

ISU79   TGTTTTGACTCACATTGTCTCCTATGGCGCCCTCACCACCAGCCATTTCCTTGACACAAT2040
ISU1894 C.....................T........T..T......C............G.2040

ISU79   TGCTTTAGTCACTGTGTCTACCGCCGGGTTTGTTCACGGGCGGTATGTCCTAAGTAGCAT2100
ISU1894 C..C........................................................2100

ISU79   CTACGCGGTCTGTGCCCTGGCTGCGTTGACTTGCTTCGTCATTAGGTTTGTGAAGAATTG2160
ISU1894 ...................AG.............CA...........2160

ISU79   CATGTCCTGGCGCTACTCATGTACTAGATATACCAACTTTCTTCTGGATACTAAGGGCAG2220
ISU1894 ............T..G.....C.......................C...........2220

ISU79   ACTCTATCGTTGGCGGTCGCCTGTCATCATAGAGAAGAGGGGCAAAGTTGAGGTCGAAGG2280
ISU1894 .............AT..................A.........................2280
                                            -32       -23(mRNA6)
ISU79   TCATCTGATCGATCTCAAAAGAGTTGTGCTTGATGGTTCCGTGGCAACCCCTATAACCAG2340
ISU1894 ............C...................C..............._____..2340
               +1>ORF6           ***<ORF5
ISU79   AGTTTCAGCGGAACAATGGGGTCGTCCTTAGATGACTTCTGTTATGATAGTACGGCTCCA2400
ISU1894 ............................................CC.............2400

ISU79   CAAAAGGTGCTTTTGGCATTTTCTATTACCTACACGCCAGTAATGATATATGCCCTAAAG2460
ISU1894 ................G..................G...............2460

ISU79   GTGAGTCGCGGCCGACTGCTAGGGCTTCTGCACCTTTTGATTTTCCTGAACTGTGCTTTC2520
ISU1894 ..........................................C.......T........2520

ISU79   ACCTTCGGGTACATGACATTCATGCACTTTCAGAGTACAAATAAGGTCGCGCTCACTATG2580
ISU1894 .................G..........................................2580
```

FIG. 9C

| | | |
|---|---|---|
| ISU79 | GGAGCAGTAGTTGCACTCCTTTGGGGGGTGTACTCAGCCATAGAAACCTGGAAATTCATC | 2640 |
| ISU1894 | ................................................................ | 2640 |
| ISU79 | ACCTCCAGATGCCGTTTGTGCTTGCTAGGCCGCAAGTACATTCTGGCCCCTGCCCACCAC | 2700 |
| ISU1894 | ................................................................ | 2700 |

-129

| | | |
|---|---|---|
| ISU79 | GTTGAAAGTGCCGCAGGCTTTCATCCGATTGCGGCAAATG<u>ATAACC</u>ACGCATTTGTCGTC | 2760 |
| ISU1894 | ........................................<u>......</u>................ | 2760 |
| ISU79 | CGGCGTCCCGGCTCCACTACGGTCAACGGCACATTGGTGCCCGGGTTGAAAAGCCTCGTG | 2820 |
| ISU1894 | ................................................................ | 2820 |

-15 (mRNA7)    +1>ORF7***<ORF6

| | | |
|---|---|---|
| ISU79 | TTGGGTGGCAGAAAAGCTGTTAAACAGGGAGTGG<u>TAAACC</u>TTGTCAAATATGCCAAATAA | 2880 |
| ISU1894 | ..................................<u>......</u>....................... | 2880 |
| ISU79 | CAACGGCAAGCAGCAGAAGAGAAAGAAGGGGGATGGCCAGCCAGTCAATCAGCTGTGCCA | 2940 |
| ISU1894 | ................................................................ | 2940 |
| ISU79 | GATGCTGGGTAAGATCATCGCCCAGCAAAACCAGTCTAGAGGCAAGGGACCGGGAAAGAA | 3000 |
| ISU1894 | .......................T............C......................... | 3000 |
| ISU79 | AAATAAGAAGAAAAACCCGGAGAAGCCCCATTTTCCTCTAGCGACTGAAGATGATGTCAG | 3060 |
| ISU1894 | ...C............................................................ | 3060 |
| ISU79 | ACATCACTTTACCCCTAGTGAGCGGCAATTGTGTCTGTCGTCAATCCAAACTGCCTTTAA | 3120 |
| ISU1894 | .........C...........................................G..C....... | 3120 |
| ISU79 | TCAAGGCGCTGGGACTTGCACCCTGTCAGATTCAGGGAGGATAAGTTACACTGTGGAGTT | 3180 |
| ISU1894 | ................................................................ | 3180 |

**

| | | |
|---|---|---|
| ISU79 | TAGTTTGCCTACGCATCATACTGTGCGCTTGATCCGCGTCACAGCATCACCCTCAGCATG | 3240 |
| ISU1894 | .........A...................................................... | 3240 |

*<ORF7

| | | |
|---|---|---|
| ISU79 | ATGGGCTGGCATTCTTGAGGCATCCCAGTGTTTGAATTGGAAGAATGCGTGGT | 3293 |
| ISU1894 | .................................................... | 3293 |

FIG. 9D

PROTEINS ENCODED BY POLYNUCLEIC ACIDS ISOLATED FROM A PORCINE REPRODUCTIVE AND RESPIRATORY SYNDROME VIRUS AND IMMUNOGENIC COMPOSITIONS CONTAINING THE SAME

This is a continuation-in-part of application Ser. No. 08/301,435, filed on Sep. 1, 1994, which is a continuation-in-part of application Ser. No. 08/131,625, filed on Oct. 5, 1993, now U.S. Pat. No. 5,695,766, which is a continuation-in-part of application Ser. No. 07/969,071, filed on Oct. 30, 1992, now abandoned. The entire contents of application Ser. Nos. 08/301,435 and 08/131,625, filed on Sep. 1, 1994 and Oct. 5, 1993, respectively, are incorporated herein by reference in their entireties.

BACKGROUND OF THE INVENTION

1. Field of the Invention

The present invention concerns polynucleic acids isolated from a porcine reproductive and respiratory syndrome virus (PRRSV), a protein and/or a polypeptide encoded by the polynucleic acids, a vaccine which protects pigs from a PRRSV based on the protein or polynucleic acids, methods of making the proteins, polypeptides and polynucleic acids, a method of protecting a pig from PRRS using the vaccine, a method of producing the vaccine, a method of treating a pig infected by or exposed to a PRRSV, and a method of detecting a PRRSV.

2. Discussion of the Background

Porcine reproductive and respiratory syndrome (PRRS), a new and severe disease in swine, was first reported in the U.S.A. in 1987, and was rapidly recognized in many western European countries (reviewed by Goyal, J. Vet. Diagn. Invest., 1993, 5:656–664; and in U.S. application Ser. Nos. 08/131,625 and 08/301,435). The disease is characterized by reproductive failure in sows and gilts, pneumonia in young growing pigs, and an increase in preweaning mortality (Wensvoort et al., Vet. Q., 13:121–130, 1991; Christianson et al., 1992, Am. J. Vet. Res. 53:485–488; U.S. application Ser. Nos. 08/131,625 and 08/301,435).

The causative agent of PRRS, porcine reproductive and respiratory syndrome virus (PRRSV), was identified first in Europe and then in the U.S.A. (Collins et al., 1992, J. Vet. Diagn. Invest., 4:117–126). The European strain of PRRSV, designated as Lelystad virus (LV), has been cloned and sequenced (Meulenberg et al., 1993, Virology, 192:62–72 and J. Gen. Virol., 74:1697–1701; Conzelmann et al., 1993, Virology, 193:329–339).

PRRSV was provisionally classified in the proposed new virus family of Arteriviridae, which includes equine arteritis virus (EAV), lactate dehydrogenase-elevating virus (LDV) and simian hemorrhagic fever virus (SHFV) (Plagemann and Moennig, 1992, Adv. Virus. Res., 41:99–192; Godeny et al., 1993, Virology, 194:585–596; U.S. application Ser. Nos. 08/131,625 and 08/301,435). This group of single plus-strand RNA viruses shares many characteristics such as genome organization, replication strategy, morphology and macrophage tropism (Meulenberg et al., 1993; U.S. application Ser. Nos. 08/131,625 and 08/301,435). Subclinical infections and persistent viremia with concurrent antibody production are also characteristic histopathologic properties of the arteriviruses.

Antigenic, genetic and pathogenic variations have been reported among PRRSV isolates (Wensvoort et al., 1992, J. Vet. Diagn. Invest., 4:134–138; Mardassi et al., 1994, J. Gen. Virol., 75:681–685; U.S. application Ser. Nos. 08/131,625 and 08/301,435). Furthermore, U.S. and European PRRSV represent two distinct genotypes (U.S. application Ser. Nos. 08/131,625 and 08/301,435). Antigenic variability also exists among different North American isolates as well (Wensvoort et al., 1992). Marked differences in pathogenicity have been demonstrated not only between U.S. and European isolates, but also among different U.S. isolates (U.S. application Ser. Nos. 08/131,625 and 08/301,435).

The genomic organization of arteriviruses resembles coronaviruses and toroviruses in that their replication involves the formation of a 3'-coterminal nested set of subgenomic mRNAs (sg mRNAs) (Chen et al., 1993, J. Gen. Virol. 74:643–660; Den Boon et al., 1990, J. Virol., 65:2910–2920; De Vries et al., 1990, Nucleic Acids Res., 18:3241–3247; Kuo et al., 1991, J. Virol., 65:5118–5123; Kuo et al., 1992; U.S. application Ser. Nos. 08/131,625 and 08/301,435). Partial sequences of several North American isolates have also been determined (U.S. application Ser. Nos. 08/131,625 and 08/301,435; Mardassi et al., 1994, J. Gen. Virol., 75:681–685).

The genome of PRRSV is polyadenylated, about 15 kb in length and contains eight open reading frames (ORFs; Meulenberg et al., 1993; U.S. application Ser. Nos. 08/131, 625 and 08/301,435). ORFs 1a and 1b probably encode viral RNA polymerase (Meulenberg et al., 1993). ORFs 5, 6 and 7 were found to encode a glycosylated membrane protein (E), an unglycosylated membrane protein (M) and a nucleo-capsid protein (N), respectively (Meulenberg et al., 1995). ORFs 2 to 4 appear to have the characteristics of membrane-associated proteins (Meulenberg et al., 1993; U.S. application Ser. No. 08/301,435). However, the translation products of ORFs 2 to 4 were not detected in virus-infected cell lysates or virions (Meulenberg et al., 1995).

The major envelope glycoprotein of EAV encoded by ORF 5 may be the virus attachment protein, and neutralizing monoclonal antibodies (MAbs) are directed to this protein (de Vries, J. Virol. 1992; 66:6294–6303; Faaberg, J. Virol. 1995; 69:613–617). The primary envelope glycoprotein of LDV, a closely related member of PRRSV, is also encoded by ORF 5, and several different neutralizing MAbs were found to specifically immunoprecipitate the ORF 5 protein (Cafruny et al., Vir. Res., 1986; 5:357–375). Therefore, it is likely that the major envelope protein of PRRSV encoded by ORF 5 may induce neutralizing antibodies against PRRSV.

It has been proposed that antigenic variation of viruses is the result of direct selection of variants by the host immune responses (reviewed by Domingo et al., J. Gen. Virol. 1993, 74:2039–2045). Thus, these hypervariable regions are likely due to the host immune selection pressure and may explain the observed antigenic diversity among PRRSV isolates.

The M and N proteins of U.S. PRRSV isolates, including ISU 3927, are highly conserved (U.S. application Ser. No. 08/301,435). The M and N proteins are integral to preserving the structure of PRRSV virions, and the N protein may be under strict functional constraints. Therefore, it is unlikely either that (a) the M and N proteins are subjected to major antibody selection pressure or that (b) ORFs 6 and 7, which are likely to encode the M and N proteins, are responsible for or correlated to viral virulence. Interestingly, however, higher sequence variation of the LDV M protein was observed between LDV isolates with differing neurovirulence (Kuo et al., 1992, Vir. Res. 23:55–72).

ORFs 1a and 1b are predicted to translate into a single protein (viral polymerase) by frameshifting. ORFs 2 to 6 may encode the viral membrane associated proteins.

In addition to the genomic RNA, many animal viruses produce one or more sg mRNA species to allow expression of viral genes in a regulated fashion. In cells infected with PRRSV, seven species of virus-specific mRNAs representing a 3'-coterminal nested set are synthesized (mRNAs 1 to 7, in decreasing order of size). mRNA 1 represents the genomic mRNA. Each of the sg mRNAs contains a leader sequence derived from the 5'-end of the viral genome.

The numbers of the sg mRNAs differ among arteriviruses and even among different isolates of the same virus. A nested set of 6 sg mRNAs was detected in EAV-infected cells and European PRRSV-infected cells. However, a nested set of six (LDV-C) or seven (LDV-P) sg mRNAs, in addition to the genomic RNA, is present in LDV-infected cells. The additional sg mRNA 1-1 of LDV-P contains the 3'-end of ORF 1b and can potentially be translated to a protein which represents the C-terminal end of the viral polymerase. Sequence analysis of the sg mRNAs of LDV and EAV indicates that the leader-mRNA junction motif is conserved. Recently, the leader-mRNA junction sequences of the European LV were also shown to contain a common motif, UCAACC, or a highly similar sequence.

The sg mRNAs have been shown to be packaged into the virions in some coronaviruses, such as bovine coronavirus (BCV) and transmissible gastroenteritis virus (TGEV). However, only trace amounts of the sg mRNAs were detected in purified virions of mouse hepatitis virus (MHV), another coronavirus. The sg mRNAs of LDV, a closely related member of PRRSV, are also not packaged in the virions, and only the genomic RNA was detected in purified LDV virions.

The sg mRNAs of LDV and EAV have been characterized in detail. However, information regarding the sg mRNAs of PRRSV strains, especially the U.S. PRRSV, is very limited. Thus, a need is felt for a more thorough molecular characterization of the sg mRNAs of U.S. PRRSV.

The packaging signal of MHV is located in the 3'-end of ORF 1b, thus only the genomic RNA of MHV is packaged. The sg mRNAs of BCV and TGEV, however, are found in purified virions. The packaging signal of BCV and TGEV has not been determined. The Aura alphavirus sg mRNA is efficiently packaged into the virions, presumably because the packaging signal is present in the sg mRNA. The sindbis virus 26S sg mRNA is not packaged into virions because the packaging signal is located in the genome segment (not present in sg mRNA). The sg mRNAs of LDV, a closely related member of PRRSV, are also not packaged into the virions.

Many mechanisms are involved in the generation of the sg mRNAs. It has been proposed that coronaviruses utilize a unique leader RNA-primed transcription mechanism in which a leader RNA is transcribed from the 3' end of the genome-sized negative-stranded template RNA, dissociates from the template, and then rejoins the template RNA at downstream intergenic regions to prime the transcription of sg mRNAs. The model predicts that the 5'-leader contains a specific sequence at its 3'-end which is repeated further downstream in the genome, preceding each of the ORFs 2 to 7. The leader joins to the body of each of the sg mRNAs via the leader-mRNA junction segment.

PRRSV is an important cause of pneumonia in nursery and weaned pigs. PRRSV causes significant economic losses from pneumonia in nursery pigs (the exact extent of which are not fully known). Reproductive disease was the predominant clinical outcome of PRRSV infections during the past few years, due to the early prevalence of relatively low virulence strains of PRRSV. Respiratory disease has now become the main problem associated with PRRSV, due to the increasing prevalence of relatively high virulence strains of PRRSV. A need is felt for a vaccine to protect against disease caused by the various strains of PRRSV.

Surprisingly, the market for animal vaccines in the U.S. and worldwide is larger than the market for human vaccines. Thus, there exists an economic incentive to develop new veterinary vaccines, in addition to the substantial public health benefit which is derived from protecting farm animals from disease.

SUMMARY OF THE INVENTION

Accordingly, one object of the present invention is to provide a polynucleic acid isolated from a porcine reproductive and respiratory syndrome virus (PRRSV).

It is a further object of the present invention to provide an isolated polynucleic acid which encodes a PRRSV protein.

It is a further object of the present invention to provide a PRRSV protein, either isolated from a PRRSV or encoded by a PRRSV polynucleic acid.

It is a further object of the present invention to provide a protein- or polynucleic acid-based vaccine which protects a pig against PRRS.

It is a further object of the present invention to provide a method of raising an effective immunological response against a PRRSV using the vaccine.

It is a further object of the present invention to provide a method of producing a protein- or polynucleic acid-based vaccine which protects a pig against PRRS.

It is a further object of the present invention to provide a method of treating a pig exposed to a PRRSV or suffering from PRRS.

It is a further object of the present invention to provide a method of detecting PRRSV.

It is a further object of the present invention to provide an antibody which immunologically binds to a PRRSV protein or to an antigenic region of such a protein.

It is a further object of the present invention to provide an antibody which immunologically binds to a protein- or polynucleic acid-based vaccine which protects a pig against a PRRSV.

It is a further object of the present invention to provide a diagnostic kit for assaying or detecting a PRRSV.

It is a further object of the present invention to provide the above objects, where the PRRS virus is an Iowa strain of PRRSV.

These and other objects, which will become apparent during the following description of the preferred embodiments, have been provided by a purified and/or isolated polypeptide selected from the group consisting of proteins encoded by one or more open reading frames (ORF's) of an Iowa strain of porcine reproductive and respiratory syndrome virus (PRRSV), proteins at least 94% but less than 100% homologous with a protein encoded by an ORF 2 of an Iowa strain of PRRSV, proteins at least 88% but less than 100% homologous with a protein encoded by ORF 3 of an Iowa strain of PRRSV, proteins at least 93% homologous with an ORF 4 of an Iowa strain of PRRSV, proteins at least 90% homologous with an ORF 5 of an Iowa strain of PRRSV, proteins at least 97% but less than 100% homologous with proteins encoded by one or both of ORF 6 and ORF 7 of an Iowa strain of PRRSV, antigenic regions of such proteins which are at least 5 amino acids in length and which effectively stimulate protection in a porcine host against a subsequent challenge with a PRRSV isolate, and combinations thereof; an isolated polynucleic acid which encodes such a polypeptide or polypeptides; a vaccine comprising an effective amount of such a polynucleotide or polypeptide(s); antibodies which specifically bind to such a polynucleotide or polypeptide; methods of producing the same; and methods of (i) effectively protecting a pig against PRRS, (ii) treating a pig exposed to a PRRSV or suffering from PRRS, and (iii) detecting a PRRSV using the same.

BRIEF DESCRIPTION OF THE FIGURES

FIGS. 1A–1G show a nucleotide sequence comparison of ORFs 2 to 5 of U.S. isolates ISU 79 (SEQ ID NO:7), ISU 1894 (SEQ ID NO:6), ISU 3927 (SEQ ID NO.2), ISU 22 (SEQ ID NO:4) and ISU 55 (SEQ ID NO:3) with other known PRRSV isolates (VR2385: SEQ ID NO:1; VR2332, SEQ ID NO:5);

FIGS. 2A, 2B, 2C and 2D respectively show the alignment of the deduced amino acid sequences of ORF 2, ORF 3, ORF 4 and ORF 5 of U.S. isolates ISU 79 (SEQ ID NOS:10, 18, 29 and 36, respectively), ISU 1894 (SEQ ID NOS:12, 19, 27 and 35, respectively), ISU 22 (SEQ ID NOS:9, 20, 28 and 37, respectively), ISU 55 (SEQ ID NOS:11, 17, 26 and 34, respectively) and ISU 3927 (SEQ ID NOS:13, 21, 30 and 38, respectively) with other known PRRSV isolates (VR2385: SEQ ID NOS: 8, 15, 24 and 32, respectively; VR2332: SEQ ID NOS:14, 22, 25 and 33, respectively; LV: SEQ ID NOS:15, 23, 31 and 39, respectively);

FIGS. 6A and 6B show a Northern hybridization of total RNAs isolated from CRL 11171 cells infected with ISU 79 at different multiplicities of infection (m.o.i.) (A), and polyadenylated RNA from cells infected with PRRSV isolates ISU 55 and ISU 79 (B);

FIGS. 9A–9D show the sequence alignment of ORFs 2 to 7 of ISU 1894 (SEQ ID NO:41) and ISU 79(SEQ ID NO:40), where the start codon of each ORF is indicated by +>, the termination codon of each ORF is indicated by asterisks (*), the determined or predicted leader-mRNA junction sequences are underlined and the locations of the leader-mRNA junction sequences relative to the start codon of each ORF are indicated by minus (−) numbers of nucleotides upstream of each ORF.

DETAILED DESCRIPTION OF THE PREFERRED EMBODIMENTS

Figure 3:
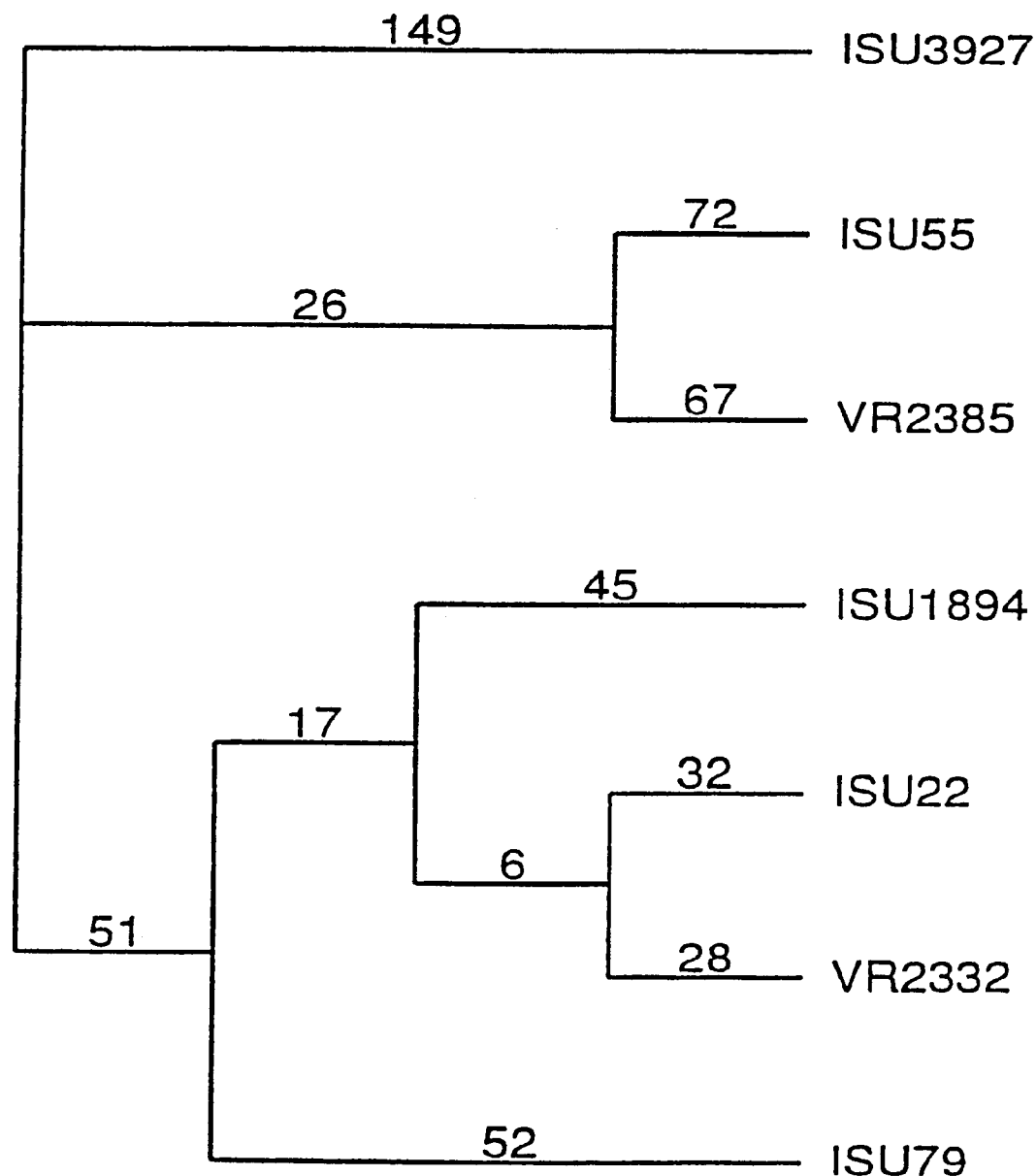
FIG. 3 shows a phylogenetic tree based on the nucleotide sequences of ORFs 2 to 7 of seven U.S. PRRSV isolates with differing virulence.

In the present application, the nucleotide sequences of the ORFs 2 to 5 of a low virulence isolate and four other Iowa strain PRRSV isolates with "moderate" and high virulence have been determined. Based on comparisons of ORFs 2 to 7 of various PRRSV isolates, the least virulent U.S. isolate known (ISU 3927) has relatively high sequence variations in ORFs 2 to 4, as compared to the variations in other U.S. isolates. Furthermore, based on analysis of the sequences of the ORFs, at least three minor genotypes exist within the major genotype of U.S. PRRSV.

Homology is determined with a GENEWORKS program (Intelligenetics, Inc.), using the following parameters (default values): cost to open a gap is 5, cost to lengthen a gap is 25, minimum diagonal length is 4, and maximum diagnol offset is 10.

Sequence analysis of the ORF 5 protein of different PRRSV isolates reveal three hypervariable regions which contained non-conserved amino acid substitutions. These regions are hydrophilic and also antigenic as predicted by computer analysis.

In the present invention, a "porcine reproductive and respiratory syndrome virus" or "PRRSV" refers to a virus which causes the diseases PRRS, PEARS, SIRS, MSD and/or PIP (the term "PIP" now appears to be disfavored), including the Iowa strain of PRRSV, other strains of PRRSV found in the United States (e.g., VR 2332), strains of PRRSV found in Canada (e.g., IAF-exp91), strains of PRRSV found in Europe (e.g., Lelystad virus, PRRSV-10), and closely-related variants of these viruses which may have appeared and which will appear in the future.

The "Iowa strain" of PRRSV includes (a) PRRSV isolates deposited in the American Type Culture Collection by the present inventors and/or described in this application and/or in either of prior U.S. application Ser. Nos. 08/131,625 and 08/301,435, (b) PRRS viruses which produce more than six sg mRNAs when cultured or passaged in CRL 11171 cells, (c) PRRSVs which produce at least 40% gross lung lesions or lung consolidation in 5-week-old caesarean-derived, colostrum-deprived piglets 10 days post-infection, (d) a PRRSV isolate having a genome which encodes a protein having the minimum homology to a PRRSV ORF described in Table 2 below, and/or (d) any PRRSV isolate having the identifying characteristics of such a virus.

The present vaccine is effective if it protects a pig against infection by a porcine reproductive and respiratory syndrome virus (PRRSV). A vaccine protects a pig against infection by a PRRSV if, after administration of the vaccine to one or more unaffected pigs, a subsequent challenge with a biologically pure virus isolate (e.g., VR 2385, VR 2386, or other virus isolate described below) results in a lessened severity of any gross or histopathological changes (e.g., lesions in the lung) and/or of symptoms of the disease, as compared to those changes or symptoms typically caused by the isolate in similar pigs which are unprotected (i.e., relative to an appropriate control). More particularly, the present vaccine may be shown to be effective by administering the vaccine to one or more suitable pigs in need thereof, then after an appropriate length of time (e.g., 1–4 weeks), challenging with a large sample ($10^{3-7}$ $TCID_{50}$) of a biologically pure PRRSV isolate. A blood sample is then drawn from the challenged pig after about one week, and an attempt to isolate the virus from the blood sample is then performed (e.g., see the virus isolation procedure exemplified in Experiment VIII below). Isolation of the virus is an indication that the vaccine may not be effective, and failure to isolate the virus is an indication that the vaccine may be effective.

Thus, the effectiveness of the present vaccine may be evaluated quantitatively (i.e., a decrease in the percentage of consolidated lung tissue as compared to an appropriate control group) or qualitatively (e.g., isolation of PRRSV from blood, detection of PRRSV antigen in a lung, tonsil or lymph node tissue sample by an immunoperoxidase assay method [described below], etc.). The symptoms of the porcine reproductive and respiratory disease may be evaluated quantitatively (e.g., temperature/fever), semi-quantitatively (e.g., severity of respiratory distress [explained in detail below], or qualitatively (e.g., the presence or absence of one or more symptoms or a reduction in severity of one or more symptoms, such as cyanosis, pneumonia, heart and/or brain lesions, etc.).

An unaffected pig is a pig which has either not been exposed to a porcine reproductive and respiratory disease infectious agent, or which has been exposed to a porcine reproductive and respiratory disease infectious agent but is not showing symptoms of the disease. An affected pig is one which shows symptoms of PRRS or from which PRRSV can be isolated.

The clinical signs or symptoms of PRRS may include lethargy, respiratory distress, "thumping" (forced expiration), fevers, roughened haircoats, sneezing, coughing, eye edema and occasionally conjunctivitis. Lesions may include gross and/or microscopic lung lesions, myocarditis, lymphadenitis, encephalitis and rhinitis. In addition, less virulent and non-virulent forms of PRRSV and of the Iowa strain have been found, which may cause either a subset of the above symptoms or no symptoms at all. Less virulent and non-virulent forms of PRRSV can be used according to the present invention to provide protection against porcine reproductive and respiratory diseases nonetheless.

The phrase "polynucleic acid" refers to RNA or DNA, as well as mRNA and cDNA corresponding to or complementary to the RNA or DNA isolated from the virus or infectious agent. An "ORF" refers to an open reading frame, or polypeptide-encoding segment, isolated from a viral genome, including a PRRSV genome. In the present polynucleic acid, an ORF can be included in part (as a fragment) or in whole, and can overlap with the 5'- or 3'-sequence of an adjacent ORF (see for example, FIG. 1 and Experiment 1 below). A "polynucleotide" is equivalent to a polynucleic acid, but may define a distinct molecule or group of molecules (e.g., as a subset of a group of polynucleic acids).

In the Experiments described hereinbelow, the isolation, cloning and sequencing of ORFs 2 to 5 of (a) a low virulence U.S. PRRSV isolate and (b) two other U.S. PRRSV isolates of varying virulence were determined. The nucleotide and deduced amino acid sequences of these three U.S. isolates were compared with the corresponding sequences of other known PRRSV isolates (see, for example, U.S. application Ser. No. 08/301,435). The results indicate that considerable genetic variations exist not only between U.S. PRRSV and European PRRSV, but also among the U.S. isolates as well.

The amino acid sequence identity between the seven U.S. PRRSV isolates studied was 91–99% in ORF 2, 86–98% in ORF 3, 92–99% in ORF 4 and 88–97% in ORF 5. The least virulent U.S. isolate known (ISU 3927) has higher sequence variations in ORFs 2 to 4 than in ORFs 5 to 7, as compared to other U.S. isolates. Three hypervariable regions with antigenic potential have been identified in the major envelope glycoprotein encoded by ORF 5.

Pairwise comparison of the sequences of ORFs 2 to 7 and phylogenetic tree analysis implied the existence of at least three groups of PRRSV variants (or minor genotypes) within the major genotype of U.S. PRRSV. The least virulent U.S. isolate known forms a distinct branch from other U.S. isolates with differing virulence. The results of this study have implications for the taxonomy of PRRSV and vaccine development.

In a further experiment, the sg mRNAs in PRRSV-infected cells were characterized. The data showed that a 3'-coterminal nested set of six or seven sg mRNAs is formed in cells infected with different isolates of PRRSV. However, unlike some of the coronaviruses and alphavirus, the sg mRNAs of PRRSV are not packaged into the virion, and only was the genomic RNA of PRRSV detected in purified virions. Variations in the numbers of the sg mRNAs among different PRRSV isolates with differing virulence were also observed. Further sequence analysis of ORFs 2 to 7 of two U.S. isolates and their comparison with the European LV reveal the heterogeneic nature of the leader-mRNA junction sequences of PRRSV.

As demonstrated in Experiment 2 below, a 3'-coterminal nested set of six or more sg mRNAs is formed in cells infected with different isolates of PRRSV. The presence of a nested set of sg mRNAs further indicates that U.S. PRRSV, like the European isolate Lelystad virus (LV), belongs to the newly proposed Arteriviridae family including LDV, EAV and SHFV. Northern blot analysis with ORF-specific probes indicates that the structure of the PRRSV sg mRNAs is polycistronic, and each of the sg mRNAs except for sg mRNA 7 contains multiple ORFs. Therefore, the sequence of each sg mRNA is contained within the 3'-portion of the next larger sg mRNA, and not all 5'-ends of the sg mRNAs overlap with the sequences of the smaller sg mRNAs.

There is no apparent correlation, however, between the numbers of sg mRNAs and viral pneumovirulence. An additional species, sg mRNA 4-1, was found to contain a small ORF (ORF 4-1) with a coding capacity of 45 amino acids at its 5'-end.

In Experiment 2 below, the sg mRNAs of PRRSV are shown not to be packaged into the virions. Whether sg mRNAs are packaged into virions may depend an whether the sg mRNAs contain a packaging signal. Since the sg mRNAs of PRRSV are not packaged into virions, the encapsidation signal of PRRSV is likely localized in the ORF 1 region which is unique to the viral genome, but which is not present in the sg mRNAs.

In Experiment 2 below, the junction segments (the leader-mRNA junction sequences) of sg mRNAs 3 and 4 of two U.S. isolates of PRRSV, ISU 79 and ISU 1894, are determined. The knowledge of the leader-mRNA junction sequence identities provides means for effectively producing (a) chimeric viruses to be used as an infectious clone and/or as a vaccine, and (b) vectors for inserting or "shuttling" one or more genes into a suitable, infectable host. Methods for designing and producing such chimeric viruses, infectious clones and vectors are known (see, for example, Sambrook et al, "Molecular Cloning: A Laboratory Manual", 2nd ed., Cold Spring Harbor Laboratory, Cold Spring Harbor, N.Y.).

The leader-mRNA junction sequence of sg mRNAs 3 and 4 of the two isolates are different (TTGACC for mRNA 4-1 of ISU 79, GTAACC for mRNA 3, and TTCACC for mRNA 4). Most of the nucleotide differences in the junctions are present in the first 3 nucleotides. The last 3 nucleotides are invariable, suggesting that the joining of the leader sequence to the bodies of sg mRNAs occurs within the 5'-end of the leader-mRNA junction sequence. Similar observations have been reported for LV, EAV and LDV.

The acquisition of the additional sg mRNA 4-1 in isolate ISU 79 is due to a single nucleotide substitution which generates a new leader mRNA junction sequence. This substitution occurs in the last nucleotide of the junction segment, suggesting that the last nucleotide of the leader-mRNA junction motif is critical for the binding of the leader and for the initiation of transcription.

Although the sequence homology between the leader and the intergenic regions of coronaviruses led to the hypothesis that basepairing might be essential in the leader-primed transcription, no experimental evidence has documented for the requirement of base-pairing in transcription of the sg mRNAs. For example, the sequence at the 3'-end of the leader of both coronaviruses and arteriviruses that is involved in the fusion process remains unknown.

Several lines of evidence support the leader-primed transcription mechanism for coronaviruses, but the presence of negative-stranded sg mRNAs and sg replicative intermediates (sg RI) in coronavirus-infected cells suggests that the mechanism involved in sg mRNA synthesis is more complex than mere base-pairing of the leader sequence with a junction sequence. However, negative-stranded sg mRNAs have not been detected in arteriviruses except for LDV, and sg RIs have been detected only in EAV-infected cells. Therefore, sg mRNA synthesis in arteriviruses, and particularly in PRRSV, may be less complicated than in coronaviruses.

Sequence analysis of the ORFs 2 to 7 of two U.S. PRRSV isolates and comparison of the sequences with LV reveals the heterogeneity of the leader-mRNA junction sequences. The presence of the leader-mRNA junction motifs at positions which do not correspond to a sg mRNA raises a question as to whether the short stretch of only six nucleotides which are conserved in the leader and junction sequences in the genomes of PRRSV and other arteriviruses is sufficient for efficient binding of the leader to these specific junction sites upstream of the ORFs. This apparent discrepancy, however, may be explained by the following two possibilities.

First, additional structural elements, such as secondary structures or the sequences surrounding the leader-mRNA junction segment, are expected to be involved in the fusion (binding) of the leader to the specific sites. It has been shown that, in MHV, the sequence flanking the consensus sequence (leader-mRNA junction sequence) of UCUAAAC affects the efficiency of sg DI RNA transcription, and that the consensus sequence was necessary but not sufficient in and of itself for the synthesis of the DI mRNA.

Second, the distance between two leader-mRNA junction regions may affect the transcription of sg mRNAs. It has been demonstrated that the downstream leader-mRNA junction region was suppressing sg DI RNA synthesis of MHV from the upstream leader-mRNA junction region. The suppression was significant when the two leader-mRNA junction sequence separation was less than 35 nucleotides. However, significant inhibition of larger sg DI RNA synthesis (from the upstream leader-mRNA junction sequence) was not observed when the two leader-mRNA junction regions were separated by more than 100 nucleotides.

The previously reported experimental results are consistent with the observations reported in Experiment 2 below, where an additional species of sg mRNA 4-1, in addition to the sg mRNA 4, is observed in some of the PRRSV isolates. The leader-mRNA junction sequences of sg mRNAs 4 and 4-1 in the Iowa strain of PRRSV are separated by about 226 nucleotides. Therefore, the synthesis of the larger sg mRNA 4-1 from the upstream leader-mRNA junction sequence is not suppressed by the presence of the downstream leader-mRNA 4 junction sequence.

In contrast, multiple potential leader-mRNA junction sequences were found at different positions upstream of ORFs 3, 5, 6 and 7, but there were no sg mRNAs corresponding to these leader-mRNA junction motifs in the Northern blot analysis. Most of these leader-mRNA junction sequences are separated by less than 50 nucleotides from the downstream leader-mRNA junction region, except for ORF 7 (in which the two potential leader-mRNA junction sequences are separated by 114 nucleotides). However, sg mRNA 7 in Northern blot analysis showed a widely-diffused band. Therefore, transcription of the larger sg mRNA 7 from the upstream leader-mRNA junction sequence may not be significantly suppressed by the downstream junction sequence, but it is not easily distinguishable from the abundant sg mRNA 7 by Northern blot analysis.

The Present Polynucleotides and Polypeptides

ORF's 2–7 of plaque-purified PRRSV isolate ISU-12 (deposited on Oct. 30, 1992, in the American Type Culture Collection, 10801 University Boulevard, Manassas, Va. 20110-2209 U.S.A., under the accession numbers VR 2385 [3×plaque-purified] and VR 2386 [non-plaque-purified]) and ORF's 6–7 of PRRSV isolates ISU-22, ISU-55, ISU-3927 (deposited on Sep. 29, 1993, in the American Type Culture Collection under the accession numbers VR 2429, VR 2430 and VR 2431, respectively), ISU-79 and ISU-1894 (deposited on Aug. 31, 1994, in the American Type Culture Collection under the accession numbers VR 2474 and VR 2475, respectively) are described in detail in U.S. application Ser. No. 08/301,435. However, the techniques used to isolate, clone and sequence these genes can be also applied to the isolation, cloning and sequencing of the genomic polynucleic acids of any PRRSV. Thus, the present invention is not limited to the specific sequences disclosed in the Experiments below.

For example, primers for making relatively large amounts of DNA by the polymerase chain reaction (and if desired, for making RNA by transcription and/or protein by translation in accordance with known in vivo or in vitro methods) can be designed on the basis of sequence information where more than one sequence obtained from a PRRSV genome has been determined (e.g., ORF's 2–7 of VR 2385, VR 2429, VR 2430, VR 2431, VR 2474, ISU-1894, VR 2332 and Lelystad virus). A region from about 15 to 50 nucleotides in length having at least 80% and preferably at least 90% identity is selected from the determined sequences. A region where a deletion occurs in one of the sequences (e.g., of at least 5 nucleotides) can be used as the basis for preparing a selective primer for selective amplification of the polynucleic acid of one strain or type of PRRSV over another (e.g., for the differential diagnosis of North American and European PRRSV strains).

Once the genomic polynucleic acid is amplified and cloned into a suitable host by known methods, the clones can be screened with a probe designed on the basis of the sequence information disclosed herein. For example, a region of from about 50 to about 500 nucleotides in length is selected on the basis of either a high degree of identity (e.g., at least 90%) among two or more sequences (e.g., in ORF's 6–7 of the Iowa strains of PRRSV disclosed in Experiment III below), and a polynucleotide of suitable length and sequence identity can be prepared by known methods (such as automated synthesis, or restriction of a suitable fragment from a polynucleic acid containing the selected region, PCR amplification using primers which hybridize specifically to the polynucleotide, and isolation by electrophoresis). The polynucleotide may be labeled with, for example, $^{32}$P (for radiometric identification) or biotin (for detection by fluorometry). The probe is then hybridized with the polynucleic acids of the clones and detected according to known methods.

The present Inventors have discovered that one or more of ORFs 2–4 may be related to the virulence of PRRSV. For example, at least one isolate of PRRSV which shows relatively low virulence also appears to have a deletion in ORF 4 (see, for example, Experiments VIII–XI in U.S. application Ser. No. 08/301,435). Furthermore, the least virulent known isolate (VR 2431) shows a relatively high degree of variance in both nucleotide and amino acid sequence information in ORFs 2–4, as compared to other U.S. PRRSV isolates. Thus, in one embodiment, the present invention concerns polynucleotides and polypeptides related to ORFs 2–4 of VR 2431.

In a further embodiment, the present invention is concerned with a polynucleic acid obtained from a PRRSV isolate which confers immunogenic protection directly or indirectly against a subsequent challenge with a PRRSV, but in which the polynucleic acid is deleted or mutated to an extent which would render a PRRSV containing the polynucleic acid either low-virulent (i.e., a "low virulence" (lv) phenotype; see the corresponding explanation in U.S. application Ser. No. 08/301,435) or non-virulent (a so-called "deletion mutant"). Preferably, one or more of ORFs 2–4 is/are deleted or mutated to an extent which would render a PRRS virus non-virulent. However, it may be desirable to retain regions of one or more of ORFs 2–4 in the present polynucleic acid which (i) encode an antigenic and/or immunoprotective peptide fragment and which (ii) do not confer virulence to a PRRS virus containing the polynucleic acid.

The present invention also encompasses a PRRSV per se in which one or more of ORFs 2–4 is deleted or mutated to an extent which renders it either low-virulent or non-virulent (e.g., VR 2431). Such a virus is useful as a vaccine or as a vector for transforming a suitable host (e.g., MA-104, PSP 36, CRL 11171, MARC-145 or porcine alveolar macrophage cells) with a heterologous gene. Preferred heterologous genes which may be expressed using the present deletion mutant may include those encoding a protein or an antigen other than a porcine reproductive and respiratory syndrome virus antigen (e.g., pseudorabies and/or swine influenza virus proteins and/or polypeptide-containing antigens, a porcine growth hormone, etc.) or a polypeptide-based adjuvant (such as those discussed in U.S. application Ser. No. 08/301,435 for a vaccine composition).

It may also be desirable in certain embodiments of the present polynucleic acid which contain, for example, the 3'-terminal region of a PRRSV ORF (e.g., from 200 to 700 nucleotides in length), at least part of which may overlap with the 5'-region of the ORF immediately downstream. Similarly, where the 3'-terminal region of an ORF may overlap with the 5'-terminal region of the immediate downstream ORF, it may be desirable to retain the 5'-region of the ORF which overlaps with the ORF immediately downstream.

The present Inventors have also discovered that ORF 5 in the PRRSV genome appears to be related to replication of the virus in mammalian host cells capable of sustaining a culture while infected with PRRSV. Accordingly, the present invention is also concerned with polynucleic acids obtained from a PRRSV genome in which ORF 5 may be present in multiple copies (a so-called "overproduction mutant"). For example, the present polynucleic acid may contain at least two, and more preferably, from 2 to 10 copies of ORF 5 from a high-replication (hr) phenotype PRRSV isolate.

Interestingly, the PRRSV isolate ISU-12 has a surprisingly large number of potential start codons (ATG/AUG sequences) near the 5'-terminus of ORF 5, possibly indicating alternate start sites of this gene. Thus, alternate forms of the protein encoded by ORF 5 of a PRRSV isolate may exist, particularly where alternate ORF's encode a protein having a molecular weight similar to that determined experimentally (e.g., from about 150 to about 250 amino acids in length). The most likely coding region for ORF 5 of ISU-12 is indicated in FIG. 1.

One can prepare deletion and overproduction mutants in accordance with known methods. For example, one can prepare a mutant polynucleic acid which contains a "silent" or degenerate change in the sequence of a region encoding a polypeptide. By selecting and making an appropriate degenerate mutation, one can substitute a polynucleic acid sequence recognized by a known restriction enzyme (see, for example, Experiment 2 below). Thus, if a silent, degenerate mutation is made at one or two of the 3'-end of an ORF and the 5'-end of a downstream ORF, one can insert a synthetic polynucleic acid (a so-called "cassette") which may contain a polynucleic acid encoding one or multiple copies of an hr ORF 5 protein product, of a PRRSV or other viral envelope protein and/or an antigenic fragment of a PRRSV protein. The "cassette" may be preceded by a suitable initiation codon (ATG), and may be suitably terminated with a termination codon at the 3'-end (TAA, TAG or TGA). Of course, an oligonucleotide sequence which does not encode a polypeptide may be inserted, or alternatively, no cassette may be inserted. By doing so, one may provide a so-called deletion mutant.

The present invention also concerns regions and positions of the polypeptides encoded by ORFs of VR 2431 which may be responsible for the low virulence of this isolate. Accordingly, the present isolated and/or purified polypeptide may be one or more encoded by a "low-virulence mutation" of one or more of ORFs 2, 3 and 4 of a PRRSV (or a low-virulence fragment thereof at least 5 amino acids in length) in which one or more of positions 12–14 of the polypeptide encoded by ORF 2 are RGV (in which "R", "G" and "V" are the one-letter abbreviations for the corresponding amino acids), positions 44–46 are LPA, position 88 is A, position 92 is R, position 141 is G, position 183 is H, position 218 is S, position 240 is S and positions 252–256 are PSSSW (SEQ ID NO:42), or any combination thereof. Other amino acid residue identities which can be further combined with one or more of the above amino acid position identities include those at position 174 (I) and position 235 (M).

The present isolated and/or purified polypeptide may also be one encoded by an ORF 3 of a PRRSV in which one or more of the specified amino acid identities may be selected from those at positions 11 (L), 23 (V), 26–28 (TDA), 65–66 (QI), 70 (N), 79 (N), 93 (T), 100–102 (KEV), 134 (K), 140 (N), 223–227 (RQRIS; SEQ ID NO:43), 234 (A) and 235 (M), or any combination thereof, which may be further combined with one or more of positions 32 (F), 38 (M), 96 (P), 143 (L), 213–217 (FQTS; SEQ ID NO:44), 231 (R), and 252 (A).

The present isolated and/or purified polypeptide may also be one encoded by an ORF 4 of a PRRSV in which one or more of the specified amino acid identities may be selected from those at positions 13 (E), 43 (N), 56 (G), 58–59 (TT), 134 (T), 139 (I) and any combination thereof, which may be further combined with one or more of positions 2–3 (AA), 51 (G) and 63 (P).

The present invention also concerns polynucleotide sequences encoding polypeptide sequences of 5 or more amino acids, preferably 10 or more amino acids, and up to the full length of the polypeptide, encoded by any one of ORFs 2–4 of VR 2431, in which the polynucleotides at the codon(s) corresponding to the amino acid positions detailed in the preceding three paragraphs are replaced with polynucleotides encoding the corresponding amino acids of the proteins encoded by the corresponding ORF of VR 2431.

In a further embodiment of the present invention, the polynucleic acid encodes one or more proteins, or antigenic regions thereof, of a PRRSV. Preferably, the present nucleic acid encodes at least one antigenic region of a PRRSV membrane (envelope) protein. More preferably, the present polynucleic acid encodes a hypervariable region from a ORF 5 PRRSV protein product (see the discussion below) or (b) contains at least one copy of the ORF-5 gene from a high virulence (hv) phenotype isolate of PRRSV (see the description of "hv phenotype" in U.S. application Ser. No. 08/301,435) and a sufficiently long fragment, region or sequence of at least one of ORF-2, ORF-3, ORF-4, ORF-5 and/or ORF-6 from the genome of a PRRSV isolate to encode an antigenic region of the corresponding protein(s) and effectively stimulate protection against a subsequent challenge with, for example, a hv phenotype PRRSV isolate.

Even more preferably, at least one entire envelope protein encoded by ORF-2, ORF-3, ORF-5 and/or ORF-6 of a PRRSV is contained in the present polynucleic acid, and the present polynucleic acid excludes or modifies a sufficiently long portion of one of ORFs 2–4 from a PRRSV to render a PRRSV containing the same either low-virulent or nonvirulent. Most preferably, the polynucleic acid is isolated from the genome of an isolate of the Iowa strain of PRRSV (for example, VR 2385 (3×plaque-purified ISU-12), VR 2386 (non-plaque-purified ISU-12), VR 2428 (ISU-51), VR 2429 (ISU-22), VR 2430 (ISU-55), VR 2431 (ISU-3927), VR 2474 (ISU-79) and/or ISU-1894).

A further preferred embodiment of the present invention includes a polynucleotide encoding an amino acid sequence from a hypervariable region of ORF 5 of a PRRSV, preferably of an Iowa strain of PRRSV. Thus, such polynucleotides encode one (or more) of the following amino acid sequences:

included. (The present invention specifically excludes the proteins and polynucleotides of ORF 5 of LV and VR 2332.)

A further preferred embodiment of the present invention concerns a purified preparation which may comprise, consist essentially of or consist of a polynucleic acid having a sequence of the formula (I) or (II):

$$5'\text{-}\alpha\text{-}\beta\text{-}3' \tag{I}$$

$$5'\text{-}\alpha\text{-}\beta\text{-}\gamma\text{-}3' \tag{II}$$

wherein α encodes at least one polypeptide, or antigenic or low-virulence fragment thereof encoded by a polynucleotide selected from the group consisting of ORFs 2, 3 and 4 of an Iowa strain of PRRSV and regions thereof encoding such antigenic and/or low-virulence fragments; and β is at least one copy of an ORF 5 from an Iowa strain of PRRSV or an antigenic fragment thereof (e.g. one or more hypervariable regions), preferably a full-length copy from a high replication (hr) phenotype; and γ encodes at least one polypeptide or antigenic fragment thereof encoded by a polynucleotide selected from the group consisting of ORF 6 and ORF 7 of an Iowa strain of PRRSV and regions thereof encoding the antigenic fragments.

Alternatively, the present invention may concern a purified preparation which may comprise, consist essentially of or consist of a polynucleic acid having a sequence of the formula (III):

$$5'\text{-}\beta\text{-}\delta\text{-}\gamma\text{-}3' \tag{III}$$

where β and γ are as defined above; and δ is either a covalent bond or a linking polynucleic acid which does not materially affect transcription and/or translation of the polynucleic acid. Preferably, β is a polynucleotide encoding at least one hypervariable region of a protein encoded by an ORF 5 of an Iowa strain of PRRSV, and more preferably, encodes a full-length protein encoded by an ORF 5 of an Iowa strain of PRRSV.

The present invention may also concern a purified preparation which may comprise, consist essentially of or consist of a polynucleic acid having a sequence of the formula (IV):

$$5'\text{-}\alpha\text{-}\beta\text{-}\delta\text{-}\gamma\text{-}3' \tag{IV}$$

where α, β, γ and δ are as defined in formulas (I)–(III) above.

The present invention may also concern a purified preparation which may comprise, consist essentially of or consist

TABLE 1

| Hypervariable Region 1 (positions 32–38) | Hypervariable Region 2 (positions 57–66) | Hypervariable Region 3 (positions 120–128) |
|---|---|---|
| NGNSGSN (SEQ ID NO: 45) | ANKFDWAVET (SEQ ID NO: 46) | LICFVIRLA (SEQ ID NO: 47) |
| SNDSSSH (SEQ ID NO: 48) | ANKFDWAVEP (SEQ ID NO: 49) | LTCFVIRFA (SEQ ID NO: 50) |
| SSSNSSH (SEQ ID NO: 51) | AGEFDWAVET (SEQ ID NO: 52) | LICFVIRFT (SEQ ID NO: 53) |
| SANSSSH (SEQ ID NO: 54) | ADKFDWAVEP (SEQ ID NO: 55) | LACFVIRFA (SEQ ID NO: 56) |
| HSNSSSH (SEQ ID NO: 57) | ADRFDWAVEP (SEQ ID NO: 58) | LTCFVIRFV (SEQ ID NO: 59) |
| SNSSSSH (SEQ ID NO: 60) | SSHFGWAVET (SEQ ID NO: 61) | LTCFIIRFA (SEQ ID NO: 62) |
| NNSSSSH (SEQ ID NO: 63) |  | FICFVIRFA (SEQ ID NO: 64) |
| NGGDSST(Y) (SEQ ID NO: 65–66) |  | FVCFVIRAA (SEQ ID NO: 57) |

In this embodiment, the polynucleotide may encode further amino acid sequences of a PRRSV ORF 5 (as disclosed in FIG. 3 or in U.S. application Ser. Nos. 08/131,625 or 08/301,435), as long as one or more of the hypervariable regions at positions 32–38, 57–66 and/or 120–128 are of a polynucleic acid, an expression vector or a plasmid having a sequence of the formula (V):

$$5'\text{-}\epsilon\text{-}\zeta\text{-}\iota\text{-}\kappa\text{-}\xi\text{-}3' \tag{V}$$

where ε, which is optionally present, is a 5'-terminal polynucleotide sequence which provides a means for operationally expressing the polynucleotides α, β, γ and δ; ξ is a polynucleotide of the formula KTVACC, where K is T, G or U, and V is A, G or C; C is a polynucleotide of at most about 130 (preferably at most 100) nucleotides in length; κ is a polynucleotide comprising one or more genes selected from the group consisting of a conventional marker or reporter gene, α, β, γ, and operationally linked combinations thereof, where α, β, and γ are as defined in formulas (I)–(IV) above; and ξ, which is optionally present, is a 3'-terminal polynucleotide sequence which does not suppress the operational expression of the polynucleotides α, β, γ and δ, and which may be operationally linked to ε (for example, in a plasmid).

Suitable marker or reporter genes include, e.g., those providing resistance to an antibiotic such as neomycin, erythromycin or chloramphenicol; those encoding a known, detectable enzyme such as β-lactamase, DHFR, horseradish peroxidase, glucose-6-phosphate dehydrogenase, alkaline phosphatase, and enzymes disclosed in U.S. Pat. 4,190,496, col. 32, line 33 through col. 38, line 44 (incorporated herein by reference), etc.; and those encoding a known antibody (e.g., mouse IgG, rabbit IgG, rat IgG, etc.) or known antigenic protein such as Protein A, Protein G, bovine serum albumin (BSA), keyhole limpet hemocyanin (KLH), bovine gamma globulin (BGG), lactalbumin, polylysine, polyglutamate, lectin, etc.

The polynucleotide ι is preferably a polynucleotide sequence at least 80% homologous to a polynucleotide sequence from a PRRSV genome located between a leader-mRNA junction sequence and the start codon of the ORF immediately downstream. "About 130" nucleotides in length refers to a length of the polynucleotide ι which does not adversely affect the operational expression of κ. For example, in ISU 79, a leader-mRNA junction sequence which does not suppress expression of ORF 7 can be found 129 bases upstream from the start codon of ORF 7 (see Experiment 2 below). Suitable exemplary sequences for the polynucleotide ι can be deduced from the sequences shown in FIGS. 1 and 9.

The present polynucleic acid may also comprise, consist essentially of or consist of combinations of the above sequences, either as a mixture of polynucleotides or covalently linked in either a head-to-tail (sense-antisense) or head-to-head fashion. Polynucleic acids complementary to the above sequences and combinations thereof (antisense polynucleic acid) are also encompassed by the present invention. Thus, in addition to possessing multiple or variant copies of ORF 5, the present polynucleic acid may also contain multiple or variant copies of one or more of ORF's 1–7, including antigenic or hypervariable regions of ORF 5, of Iowa strain PRRSV's.

Similar to the methods described above and in the Experiments described below and in U.S. application Ser. Nos. 08/131,625 and 08/301,435, one can prepare a library of recombinant clones (e.g., using E. coli as a host) containing suitably prepared restriction fragments of a PRRSV genome (e.g., inserted into an appropriate plasmid expressible in the host). The clones are then screened with a suitable probe (e.g, based on a conserved sequence of ORF's 2–3; see, for example, FIG. 22 of U.S. application Ser. No. 08/301,435). Positive clones can then be selected and grown to an appropriate level. The polynucleic acids can then be isolated from the positive clones in accordance with known methods. A suitable primer for PCR can then be designed and prepared as described above to amplify the desired region of the polynucleic acid. The amplified polynucleic acid can then be isolated and sequenced by known methods.

The present purified preparation may also contain a polynucleic acid selected from the group consisting of sequences having at least 97% sequence identity (or homology) with at least one of ORFs 5–7 of VR 2385, VR 2430 and/or VR 2431; and sequences encoding a polypeptide having at least the minimum sequence identity (or homology) with at least one of ORF's 2–5 of VR 2385, VR 2428, VR 2429, VR 2430, VR 2431, VR 2474 and ISU-1894, as follows:

TABLE 2

| Relative to | Minimum % Homology with ORF: | | | |
|---|---|---|---|---|
| Isolate: | 2 | 3 | 4 | 5 |
| VR 2385 | 99 | 92 | 95 | 90 |
| VR 2429 | 100 | 99 | 99 | 98 |
| VR 2430 | 98 | 95 | 96 | 90 |
| VR 2431 | 94 | 88 | 93 | 92 |
| VR 2474 | 99 | 97 | 97 | 95 |
| ISU 1894 | 97 | 97 | 99 | 97 |

Preferably, the polynucleic acid excludes or modifies a sufficiently long region or portion of one or more of ORFs 2–4 of the hv PRRSV isolates VR 2385, VR 2429, ISU-28, ISU-79 and/or ISU-984 to render the isolate low-virulent or non-virulent.

In the context of the present application, "homology" refers to the percentage of identical nucleotide or amino acid residues in the sequences of two or more viruses, aligned in accordance with a conventional method for determining homology (e.g., the MACVECTOR or GENEWORKS computer programs, aligned in accordance with the procedure described in Experiment III in U.S. application Ser. No. 08/301,435).

Preferably, the present isolated polynucleic acid encodes a protein, polypeptide, or antigenic fragment thereof which is at least 10 amino acids in length and in which non-homologous amino acids which are non-essential for antigenicity may be conservatively substituted. An amino acid residue in a protein, polypeptide, or antigenic fragment thereof is conservatively substituted if it is replaced with a member of its polarity group as defined below:
Basic amino acids:
 lysine (Lys), arginine (Arg), histidine (His)
Acidic amino acids:
 aspartic acid (Asp), glutamic acid (Glu), asparagine (Asn), glutamine (Gln)
Hydrophilic, nonionic amino acids:
 serine (Ser), threonine (Thr), cysteine (Cys), asparagine (Asn), glutamine (Gln)
Sulfur-containing amino acids:
 cysteine (Cys), methionine (Met)
Hydrophobic, aromatic amino acids:
 phenylalanine (Phe), tyrosine (Tyr), tryptophan (Trp)
Hydrophobic, nonaromatic amino acids:
 glycine (Gly), alanine (Ala), valine (Val), leucine (Leu), isoleucine (Ile), proline (Pro)

More particularly, the present polynucleic acid encodes one or more of the protein(s) encoded by the second, third, fourth, fifth, sixth and/or seventh open reading frames (ORF's 2–7) of the PRRSV isolates VR 2385, VR 2386, VR 2428, VR 2429, VR 2430, VR 2431, VR 2474 and/or ISU-1894 (e.g., one or more of the sequences shown in FIG. 3 and/or SEQ ID NOS:15, 17, 19, 43, 45, 47, 49, 51, 53, 55, 57, 59, 61, 63 and 65 of U.S. application Ser. No. 08/301, 435).

ORF's 6 and 7 are not likely candidates for controlling virulence and replication phenotypes of PRRSV, as the nucleotide sequences of these genes are highly conserved among high virulence (hv) and low virulence (lv) isolates (see Experiment III of U.S. application Ser. No. 08/301, 435). However, ORF 5 in PRRSV isolates appears to be less conserved among high replication (hr) and low replication (lr) isolates. Therefore, it is believed that the presence of an ORF 5 from an hr PRRSV isolate in the present polynucleic acid will enhance the production and expression of a recombinant vaccine produced from the polynucleic acid.

Furthermore, ORF 5 of PRRSV contains three hydrophilic, hypervariable regions typically associated with antigenicity in a polypeptide. Thus, the present invention also encompasses polynucleotides encoding a polypeptide comprising one or more hypervariable regions of a PRRSV ORF 5, preferably a polypeptide of the formula a-b-c-d-e-f-g, where:

a is an amino group, a poly(amino acid) corresponding to positions 1–31 of a protein encoded by a PRSSV ORF 5, or a fragment of such a poly(amino acid) which does not adversely affect the antigenicity of the polypeptide;

b is an amino acid sequence selected from the group consisting of those sequences listed under Hypervariable Region No. 1 in Table 1 above, c is an amino acid sequence corresponding to positions 39–56 of a protein encoded by a PRSSV ORF 5 (preferably a sequence of the formula LQLIYNLTLCELNGTDWL, (SEQ ID NO:68) in which one or more [preferably 1–10] amino acids may be conservatively substituted), d is an amino acid sequence selected from the group consisting of those sequences listed under Hypervariable Region No. 2 in Table 1 above, e is an amino acid sequence corresponding to positions 67–119 of a protein encoded by a PRRSV ORF 5, in which one or more (preferably 1–20, and more preferably 1–10) amino acid residues may be conservatively substituted and which does not adversely affect the antigenicity of the polypeptide, f is an amino acid sequence selected from the group consisting of those sequences listed under Hypervariable Region No. 3 in the Table above, and g is a carboxy group (a group of the formula —COOH), an amino acid sequence corresponding to positions 129–200 of a protein encoded by a PRSSV ORF 5 or a fragment thereof which does not adversely affect the antigenicity of the polypeptide.

Accordingly, it is preferred that the present polynucleic acid, when used for immunoprotective purposes (e.g., in the preparation of a vaccine), contain at least one copy of ORF 5 from a high-replication isolate (i.e., an isolate which grows to a titer of $10^6$–$10^7$ $TCID_{50}$ in, for example, CRL 11171 cells; also see the discussions in Experiments VIII–XI U.S. application Ser. No. 08/301,435).

On the other hand, the lv isolate VR 2431 appears to be a deletion mutant, relative to hv isolates (see Experiments III and VIII–XI U.S. application Ser. No. 08/301,435). The deletion appears to be in ORF 4, based on Northern blot analysis. Accordingly, when used for immunoprotective purposes, the present polynucleic acid preferably does not contain a region of ORF 4 from an hv isolate responsible for high virulence, and more preferably, excludes the region of ORF 4 which does not overlap with the adjacent ORF's 3 and 5.

It is also known (at least for PRRSV) that neither the nucleocapsid protein nor antibodies thereto confer immunological protection against PRRSV to pigs. Accordingly, the present polynucleic acid, when used for immunoprotective purposes, contains one or more copies of one or more regions from ORF's 2, 3, 4, 5 and 6 of a PRRSV isolate encoding an antigenic region of the viral envelope protein, but which does not result in the symptoms or histopathological changes associated with PRRS when administered to a pig. Preferably, this region is immunologically cross-reactive with antibodies to envelope proteins of other PRRSV isolates.

Similarly, the protein encoded by the present polynucleic acid confers protection against PRRS to a pig administered a composition comprising the protein, and antibodies to this protein are immunologically cross-reactive with the envelope proteins of other PRRSV isolates. More preferably, the present polynucleic acid encodes the entire envelope protein of a PRRSV isolate or a protein at least 80% homologous thereto and in which non-homologous residues are conservatively substituted, or alternatively a protein at least 98% homologous thereto. Most preferably, the present polynucleotide is one of the sequences shown in FIG. 1, encompassing at least one of the open reading frames recited therein.

Relatively short segments of polynucleic acid (about 20 bp or longer) in the genome of a virus can be used to screen or identify tissue and/or biological fluid samples from infected animals, and/or to identify related viruses, by methods described herein and known to those of ordinary skill in the fields of veterinary and viral diagnostics and veterinary medicine. Accordingly, a further aspect of the present invention encompasses an isolated (and if desired, purified) polynucleic acid consisting essentially of a fragment of from 15 to 2000 bp, preferably from 18 to 1000 bp, and more preferably from 21 to 100 bp in length, derived from ORF's 2–7 of a PRRSV genome (preferably the Iowa strain of PRRSV). Particularly preferably, the present isolated polynucleic acid fragments are obtained from a terminus of one or more of ORF's 2–7 of the genome of the Iowa strain of PRRSV, and most preferably, are selected from the group consisting of the primers described in Experiments 1 and 2 below and SEQ ID NOS:1–12, 22 and 28–34 of U.S. application Ser. No. 08/301,435.

The present invention also concerns a diagnostic kit for assaying a porcine reproductive and respiratory syndrome virus, comprising (a) a first primer comprising a polynucleotide having a sequence of from 10 to 50 nucleotides in length which hybridizes to a genomic polynucleic acid from an Iowa strain of porcine reproductive and respiratory syndrome virus at a temperature of from 25 to 75° C., (b) a second primer comprising a polynucleotide having a sequence of from 10 to 50 nucleotides in length, said sequence of said second primer being found in said genomic polynucleic acid from said Iowa strain of porcine reproductive and respiratory syndrome virus and being downstream from the sequence to which the first primer hybridizes, and (c) a reagent which enables detection of an amplified polynucleic acid. Preferably, the reagent is an intercalating dye, the fluorescent properties of which change upon intercalation into double-stranded DNA.

The present isolated polynucleic acid fragments can be obtained by: (i) digestion of the cDNA corresponding to (complementary to) the viral polynucleic acids with one or more appropriate restriction enzymes, (ii) amplification by PCR (using appropriate primers complimentary to the 5' and 3'-terminal regions of the desired ORF(s) or to regions upstream of the 5'-terminus or downstream from the 3'-terminus) and cloning, or (iii) synthesis using a commercially available automated polynucleotide synthesizer.

Another embodiment of the present invention concerns one or more proteins or antigenic fragments thereof from a PRRS virus, preferably from the Iowa strain of PRRSV. As described above, an antigenic fragment of a protein from a PRRS virus (preferably from the Iowa strain of PRRSV) is at least 5 amino acids in length, particularly preferably at least 10 amino acids in length, and provides or stimulates an immunologically protective response in a pig administered a composition containing the antigenic fragment.

Methods of determining the antigenic portion of a protein are known to those of ordinary skill in the art (see the description above). In addition, one may also determine an essential antigenic fragment of a protein by first showing that the full-length protein is antigenic in a host animal (e.g., a pig). If the protein is still antigenic in the presence of an antibody which specifically binds to a particular region or sequence of the protein, then that region or sequence may be non-essential for immunoprotection. On the other hand, if the protein is no longer antigenic in the presence of an antibody which specifically binds to a particular region or sequence of the protein, then that region or sequence is considered to be essential for antigenicity.

Three hypervariable regions in ORF 5 of PRRSV have been identified by comparing the amino acid sequences of the ORF 5 product of all available PRRSV isolates (see, for example, FIG. 2D). Amino acid variations in these three regions are significant, and are not structurally conserved (FIG. 2D). All three hypervariable regions are hydrophilic and antigenic. Thus, these regions are likely to be exposed to the viral membrane and thus be under host immune selection pressure, hypervariable regions as antigenic determinants in the ORF 5 envelope protein.

The present invention also concerns a protein or antigenic fragment thereof encoded by one or more of the polynucleic acids defined above, and preferably by one or more of the ORF's of a PRRSV, more preferably of the Iowa strain of PRRSV. The present proteins and antigenic fragments are useful in immunizing pigs against PRRSV, in serological tests for screening pigs for exposure to or infection by PRRSV (particularly the Iowa strain of PRRSV), etc.

For example, the present protein may be selected from the group consisting of the proteins encoded by ORF's 2–7 of VR 2385, ISU-22 (VR 2429), ISU-55 (VR 2430), ISU-1894, ISU-79 (VR 2474) and ISU-3927 (VR 2431) (e.g., one or more of the sequences shown in FIG. 2 and/or SEQ ID NOS:15, 17, 19, 43, 45, 47, 49, 51, 53, 55, 57, 59, 61, 67, 69 and 71 of U.S. application Ser. No. 08/301,435); antigenic regions of at least one of these proteins having a length of from 5 amino acids to less than the full length of the protein; polypeptides having the minimum homology with the protein encoded by the PRSSV ORF indicated in Table 2 above; and polypeptides at least 97% homologous with a protein encoded by one of the ORF's 6–7 of VR 2385, VR 2429, VR 2430, ISU-1894, ISU-79 and VR 2431 (e.g., SEQ ID NOS:17, 19, 43, 45, 47, 49, 51, 53, 55, 57, 59 and 61 of U.S. application Ser. No. 08/301,435). Preferably, the present protein has a sequence encoded by an ORF selected from the group consisting of ORFs 2–5 of VR 2385, VR 2428, VR 2429, VR 2430, VR 2431, VR 2474 and ISU-1894 (see, for example, FIGS. 2A–D); variants thereof which provide effective immunological protection to a pig administered the same and in which from 1 to 100 (preferably from 1 to 50 and more preferably from 1 to 25) deletions or conservative substitutions in the amino acid sequence exist; and antigenic fragments thereof at least 5 and preferably at least 10 amino acids in length which provide effective immunological protection to a pig administered the same.

More preferably, the present protein variant or protein fragment has a binding affinity (or association constant) of at least 1% and preferably at least 10% of the binding affinity of the corresponding full-length, naturally-occurring protein to a monoclonal antibody which specifically binds to the full-length, naturally-occurring protein (i.e., the protein encoded by a PRRSV ORF).

The present invention also concerns a method of producing a polypeptide, comprising expressing the present polynucleic acid in an operational expression system, and purifying the expressed polypeptide from the expression system. Suitable expression systems include those conventionally used for either in vitro or in vivo expression of proteins and polypeptides, such as a rabbit reticulocyte system for in vitro expression, and for in vivo expression, a modified or chimeric PRRSV (used to infect an infectable host cell line, such as MA-104, CRL 11171, PSP-36, PSP-36-SAH, MARC-145 and porcine alveolar macrophages), or a conventional expression vector containing the present polynucleic acid, under the operational control of a known promoter (e.g., a thymidine kinase promoter, SV40, etc.) for use in conventional expression systems (e.g., bacterial plasmids and corresponding host bacteria, yeast expression systems and corresponding host yeasts, etc.). The expressed polypeptide or protein is then purified or isolated from the expression system by conventional purification and/or isolation methods.

Other features of the invention will become apparent in the course of the following descriptions of exemplary embodiments, which are given for illustration of the invention, and are not intended to be limiting thereof.

Experiment I

Summary

The sequences of ORFs 2 to 5 of one low virulence, one "moderate" virulence and one high virulence U.S. PRRSV isolate have been determined and analyzed. Comparisons with known sequences of other PRRSV isolates show that considerable sequence variations at both nucleotide and amino acid levels exist in ORFs 2 to 5 of seven U.S. isolates with differing virulence. However, ORFs 6 and 7 of these seven U.S. isolates are highly conserved (U.S. application Ser. No. 08/301,435). Extensive sequence variations were also found in ORFs 2 to 7 between the European LV and the U.S. isolates. The least virulent U.S. PRRSV isolate known (ISU-3927) displayed the most sequence variation, in comparison with other U.S. isolates.

The phylogenetic relationship of the U.S. isolates was also analyzed. Phylogenetic analysis of the ORFs 2 to 7 of the U.S. isolates indicated that there are at least three groups of PRRSV variants (or minor genotypes) within the major U.S. PRRSV genotype. Consequently, it is highly likely that a number of additional major or minor genotypes will be identified as more virus isolates from different geographic regions are examined.

Interestingly, the least virulent U.S. isolate known (ISU 3927) forms a branch distinct from other U.S. isolates. Analysis of the nucleotide and amino acid sequences also showed that the isolate ISU 3927 exhibits the most variations in ORFs 2 to 4, relative to other U.S. isolates. Many of these variations in isolate ISU 3927 result in non-conserved amino acid substitutions. However, these non-conserved changes in isolate ISU 3927, as compared to other U.S. isolates, do not appear to be limited to a particular region; they are present throughout ORFs 2 to 4. Therefore, a specific correlation between sequence variations and viral virulence is not yet fully elucidated (although certain positions in ORF 3 appear to be possibly related to virulence; see FIG. 2B, positions 30, 48, 54–56, 134, 140, 143, 147, 153, 206, and 215; amino acids at one or more of these positions may serve as a basis for mutating other known proteins encoded by a PRRSV ORF 3).

Results

The amino acid sequence identity between seven U.S. PRRSV isolates was 91–99% in ORF 2, 86–98% in ORF 3, 92–99% in ORF 4 and 88–97% in ORF 5. The least virulent U.S. isolate known has higher sequence variations in the ORFs 2 to 4 than in ORFs 5 to 7, as compared to other U.S. isolates. Three hypervariable regions with antigenic potential were identified in the major envelope glycoprotein encoded by ORF 5.

Pairwise comparison of the sequences of ORFs 2 to 7 and phylogenetic tree analysis implied the existence of at least three groups of PRRSV variants (or minor genotypes) within the major genotype of U.S. PRRSV. The least virulent U.S. isolate known forms a distinct branch from other U.S. isolates with differing virulence. The results of this study have implications for the taxonomy of PRRSV and vaccine development.

FIG. 1 shows a nucleotide sequence comparison of ORFs 2 to 5 of U.S. isolates ISU 3927, ISU 22 and ISU 55 with other known PRRSV isolates. The nucleotide sequence of VR 2385 is shown on top, and only differences are indicated. The start codon of each ORF is indicated by +>, and the termination codon of each ORF is indicated by asterisks (*). The leader-mRNA junction sequences for subgenomic mRNAs 3, 4 and 4-1 are underlined, and the locations of the junction sequences relative to the start codon of each ORF are indicated by minus (–) numbers of nucleotides upstream of each ORF. The sequences of VR 2385 (U.S. application Ser. Nos. 08/131,625 and 08/301,435), VR 2332, ISU 79 and ISU 1894 (U.S. application Ser. No. 08/301,435) used in this alignment were previously reported.

Materials and Methods

Cells and viruses:

The ATCC CRL 11171 cell line was used to propagate the PRRSV. The cells were grown in Dulbecco's minimal essential medium (DMEM) supplemented with 10% fetal bovine serum (FBS) and 1×antibiotics (penicillin G 10,000 unit/ml, streptomycin 10,000 mg/ml and amphotericin B 25 mg/ml).

Three U.S. isolates of PRRSV used in this study, designated as ISU 22, ISU 55 and ISU 3927, were isolated from pig lungs obtained from different farms in Iowa during PRRS outbreaks. All three isolates were plaque-purified three times on CRL 11171 cells before further experimentation. Comparative pathogenicity studies showed that isolate ISU 3927 is the least virulent isolate among 10 different U.S. PRRSV isolates. Isolate ISU 22 is a high virulence isolate and isolate ISU 55 is "moderately" pathogenic. All of the three virus isolates used in this experiment were at seventh passage.

Isolation of PRRSV intracellular RNAs:

Confluent monolayers of CRL 11171 cells were infected with the three U.S. isolates of PRRSV, ISU 22, ISU 55 and ISU 3927, respectively, at a multiplicity of infection (m.o.i.) of 0.1. At 24 hrs. postinfection, the infected cells were washed three times with cold PBS buffer. The total intracellular RNAs were then isolated by guanidinium isothiocyanate and phenol-chloroform extraction (Stratagene). The presence of virus-specific RNA species in the RNA preparation was confirmed by Northern blot hybridization (data not shown). The total intracellular RNAs were quantified spectrophotometrically.

Reverse transcription and polymerase chain reaction (RT-PCR):

First strand complementary (c) DNA was synthesized from the total intracellular RNAs by reverse transcription using random primers as described previously (Meng et al., 1993, J. Vet. Diagn. Invest., 5:254–258). For amplification of the entire protein coding regions of the ORFs 2 to 5 of the three isolates of PRRSV, two sets of primers were designed on the basis of the sequences of VR 2385 and LV. Primers JM259 (5'-GGGGATCCTTTTGTGGAGCCGT-3'; SEQ ID NO: 68) and JM260 (5'-GGGGAATTCGGGATA GGGAATGTG-3'; SEQ ID NO: 69) amplified the sequence of ORFs 4 and 5, and primers XM992 (5'-GGG GGATCCTGTTGG-TAATAG(A)GTCTG-3'; SEQ ID NOS: 70–71 and XM993 (5'-GGTGAATTCGTTTTATT TCCCTCCGGGC-3'; SEQ ID NO: 72) amplified the sequence of ORFs 2 and 3. Unique restriction sites (EcoRI or BamHI) at the 5' end of these primers were introduced to facilitate cloning. A degenerate base, G (A), was synthesized in primer XM 992 based on the sequences of VR 2385 and LV (Meulenberg et al., 1993; U.S. application Ser. No. 08/301,435). PCR was performed as described previously (Meng et al., 1993, J. Vet. Diagn. Invest., 5:254–258).

Cloning and nucleotide sequencing:

The RT-PCR products were analyzed by a 0.8% agarose gel electrophoresis. The two PCR fragments representing ORFs 2 and 3 as well as ORFs 4 and 5, respectively, were purified by the glassmilk procedure (GENECLEAN kit, BIO 101, Inc.). The purified fragments were each digested with BamHI and EcoRI, and cloned into the vector pSK+ as described previously (Meng et al., 1993). The *E. Coli* DH 5α cells were used for transformation of recombinant plasmids. White colonies were selected and grown in LB broth containing 100 mg/ml ampicillin. The *E. Coli* cells containing recombinant plasmid were lysed with lysozyme, and the plasmids were then isolated by using the Qiagen column (QIAGEN Inc.).

Plasmids containing viral inserts were sequenced with an automated DNA Sequencer (Applied Biosystem, Inc.). Three or more independent CDNA clones representing the entire sequence of ORFs 2 to 5 from each of the three PRRSV isolates were sequenced with universal and reverse primers. Several virus-specific primers, XM969 (5'-GATAGAGTCTGCCCTTAG-3'; SEQ ID NO: 73), XM970 (5'-GGTTTCACCTAGAATGGC-3'; SEQ ID NO: 74), XM1006 (5'-GCTTCTGAGATGAGTGA-3'; SEQ ID NO: 75), XM077 (5'-CAACCAGGCGTAAACACT-3'; SEQ ID NO: 76) and XM078 (5'-CTGAGCAATT ACAGAAG-3'; SEQ ID NO: 77), were also used to determine the sequence of ORFs 2 to 5.

Sequence analyses:

Sequence data were combined and analyzed by using MacVector (International Biotechnologies, Inc.) and GeneWorks (IntelliGenetics, Inc.) computer software programs. Phylogenetic analyses were performed using the PAUP software package version 3.1.1 (David L. Swofford, Illinois Natural History Survey, Champaign, Ill.). PAUP employs the maximum parsimony algorithm to construct phylogenetic trees.

Results

Nucleotide sequence analyses of ORFs 2 to 5:

The sequences of ORFs 2 to 5 of five PRRSV isolates, ISU 79, ISU 1894, ISU 22, ISU 55 and ISU 3927, were determined and compared with other known PRRSV isolates including VR 2385, VR 2332 and LV (Meulenberg et al., 1993). The sequences of ORFs 6 and 7 of isolates VR 2385, ISU 22, ISU 55, ISU 79, ISU 1894 and ISU 3927 were reported previously (U.S. application Ser. No. 08/301,435). The isolates used in this experiment have been shown to differ in pneumovirulence in experimentally-infected pigs (U.S. application Ser. Nos. 08/131,625 and 08/301,435). ISU 3927 is the least virulent isolate among ten different U.S. PRRSV isolates (U.S. application Ser. No. 08/131,625 and U.S. application Ser. No. 08/301,435).

Like other U.S. PRRSV isolates, ORFs 2 to 4 of these isolates overlapped each other (FIG. 1). However, unlike LV, ORFs 4 and 5 of the U.S. isolates are separated by 10 nucleotides (FIG. 1). ORFs 4 and 5 of LV overlapped by one nucleotide. The single nucleotide substitution from A of the start codon of ORF 5 in LV to T in the U.S. isolates places the start codon of ORF 5 of the U.S. isolates 10 nucleotides downstream of the ORF 4 stop codon. Therefore, a 10-nucleotide noncoding sequence appears between ORFs 4 and 5 of the known U.S. isolates (FIG. 1).

ORF 2 of ISU 79 is 3 nucleotides shorter than other U.S. isolates. The single nucleotide substitution from TGG to TAG just before the stop codon of ORF 2 creates a new stop codon in ISU 79 (FIG. 1). A 3-nucleotide deletion was also found in ORF 5 of ISU 3927, compared to other U.S. isolates (FIG. 1). The size of ORFs 2 to 5 of all the U.S. isolates are identical, except for the ORF 2 of ISU 79 and ORF 5 of ISU 3927, both of which are 3 nucleotides shorter than the other ORFs (FIG. 1).

Sequence comparisons of ORFs 2 to 5 of the seven U.S. PRRSV isolates shown in FIG. 1 indicate that there are considerable nucleotide sequence variations in ORFs 2 to 5 of the U.S. isolates (FIG. 1). The nucleotide sequence identity was 96–98% in ORF 2, 92–98% in ORF 3, 92–99% in ORF 4, and 90–98% in ORF 5 between VR 2385, VR 2332, ISU 22, ISU 55, ISU 79, and ISU 1894 (Table 3).

The least virulent isolate ISU 3927 has the most variations among the seven U.S. isolates (FIG. 1 and Table 3). The nucleotide sequence identity between ISU 3927 and other U.S. isolates was 93–94% in ORF 2, 89–90% in ORF 3, and 91–93% in ORF 4 (Table 3). Like ORFs 6 and 7 (U.S. application Ser. No. 08/301,435), ORF 5 of ISU 3927 has no significant changes except for a 3-nucleotide deletion (FIG. 1). ORF 5 of ISU 3927 shares 91–93% nucleotide sequence identity with the ORF 5 of other U.S. isolates (Table 3).

However, extensive sequence variation was found in ORFs 2 to 5 between LV and the U.S. isolates (FIG. 1 and Table 3). The nucleotide sequence identity between LV and the U.S. isolates was 65–67% in ORF 2, 61–64% in ORF 3, 63–66% in ORF 4, and 61–63% in ORF 5 (Table 3). Extensive genetic variations in ORFs 6 and 7 between LV and U.S. PRRSV also exists (U.S. application Ser. Nos. 08/131,625 and 08/301,435). These results indicate that the least virulent isolate ISU 3927 is also the most distantly related of the U.S. isolates, with genetic variations occurring mostly in ORFs 2 to 4.

The single nucleotide substitution from TGG to TAG before the stop codon in ORF 2 observed in ISU 79 was also present in isolates ISU 55 and ISU 3927, both of which produce seven sg mRNAs, but not in isolates ISU 22, ISU 1894 or VR 2385, which each synthesize only six sg mRNAs (U.S. application Ser. Nos. 08/131,625 and 08/301,435). The results indicate that the leader-mRNA 4–1 junction sequence of ISU 55 and ISU 3927 is very likely to be the same as ISU 79 (FIG. 1).

The leader-mRNA junction sequences for sg mRNAs 3 and 4 of ISU 79 and ISU 1894 were determined to be GUAACC at 89 nucleotides upstream of ORF 3 for sg mRNA 3, and UUCACC at 10 nucleotides upstream of ORF 4 for sg mRNA 4 (U.S. application Ser. No. 08/301,435; see also Experiment 2 below). A sequence comparison of isolates ISU 22, ISU 55 and ISU 3927 with isolates VR 2385, ISU 79 and ISU 1894 indicates that the leader-mRNA junction sequences for sg mRNAs 3 and 4 are conserved among the U.S. isolates (FIG. 1).

Analysis of the deduced amino acid sequences encoded by ORFs 2 to 5:

FIG. 2 shows the alignment of the deduced amino acid sequences of ORF 2 (A), ORF 3 (B), ORF 4 (C) and ORF 5 (D) of U.S. isolates ISU 22, ISU 55 and ISU 3927 with other known PRRSV isolates. The sequence of VR 2385 is shown on top, and only differences are indicated. Deletions are indicated by (–). The proposed signal peptide sequence in the ORF 5 of LV (D) is underlined (Meulenberg et al., 1995). Three hypervariable regions with antigenic potentials in ORF 5 (D) were indicated by asterisks (*). The published sequences used in this alignment were LV (Meulenberg et al., 1993), VR 2385 (application Ser. Nos. 08/131,625 and 08/301,435), VR 2332, ISU 79 and ISU 1894 (U.S. application Ser. No. 08/301,435).

On the basis of its high content of basic amino acids and its hydrophilic nature, the translation product of ORF 7 is predicted to be the nucleocapsid protein (U.S. application Ser. Nos. 08/131,625 and 08/301,435; Meulenberg et al., 1993; Conzelmann et al., 1993; Mardassi et al., 1994). The ORF 6 product lacks a potential amino-terminal signal sequence and contains several hydrophobic regions which may represent the potential transmembrane fragments. Therefore, the ORF 6 product was predicted to be the M protein (U.S. application Ser. Nos. 08/131,625 and 08/301,435; Meulenberg et al., 1993; Conzelmann et al., 1993).

Computer analysis shows that the products encoded by ORFs 2 to 5 of the U.S. isolates all have hydropathy characteristics reminiscent of membrane-associated proteins. The translation products of ORFs 2 to 5 each contain a hydrophobic amino terminus. The N-terminal hydrophobic sequences may function as a signal sequence for each of these ORFs, and they may be involved in the transportation of ORFs 2 to 5 to the endoplasmic reticulum of infected cells. At least one additional hydrophobic domain in each of ORFs 2 to 5 was found at the carboxy termini. These additional hydrophobic domains may function as membrane anchors.

The deduced amino acid sequences of ORFs 2 to 5 of the seven U.S. isolates examined also varied considerably (FIG. 2), indicating that most of the nucleotide differences observed in FIG. 1 are not silent mutations. The amino acid sequence identity between VR 2385, VR 2332, ISU 22, ISU 55, ISU 79, and ISU 1894 was 95–99% in ORF 2, 90–98% in ORF 3, 94–98% in ORF 4, and 88–97% in ORF 5 (Table 3).

Again, the least virulent isolate ISU 3927 displayed more variations with other U.S. isolates in ORFs 2 to 4 (FIG. 2 and Table 3) than in ORFs 5 to 7 (U.S. application Ser. No. 08/301,435 and Table 3). ORFs 2 to 5 of LV share only 57–61%, 55–56%, 65–67%, and 51–55% amino acid sequence identity with those ORFs of the U.S. isolates, respectively (Table 3). Deletions or insertions were found throughout ORFs 2 to 5 in comparing European LV and U.S. isolates (FIG. 2).

Sequence comparison of the ORF 5 product showed that the N-terminal region of ORF 5 is extremely variable, both (a) between U.S. isolates and LV and also (b) among the various U.S. isolates (FIG. 2D). In LV, the first 32–33 amino acid residues of ORF 5 may represent the signal sequence (Meulenberg et al., 1995; FIG. 2D). Therefore, the potential signal sequence of ORF 5 in all the PRRSV isolates is very heterogeneous. This heterogeneity is not due to any host immune selection pressure, because the signal peptide will be cleaved out and not be present in mature virions.

Three additional hypervariable regions were also identified by comparing the amino acid sequences of ORF 5 of all the PRRSV isolates available (FIG. 2D). Amino acid variations in these three regions are significant, and are not structurally conserved (FIG. 2D). Computer analysis indicates that all three hypervariable regions are hydrophilic and antigenic. Thus, it is likely that these regions are exposed to the viral membrane and are under host immune selection pressure. However, further experiments may be necessary to confirm the specific functions of these hypervariable regions as antigenic determinants in the ORF 5 envelope protein.

The Phylogenetic relationships among U.S. isolates of PRRSV:

It has been shown previously that U.S. PRRSV and European PRRSV represent two distinct genotypes, based on analysis of the M and N genes (U.S. application Ser. No. 08/301,435). To determine the phylogenetic relationships of U.S. PRRSV isolates, ORFs 2 to 7 of the seven U.S. PRRSV isolates shown in FIGS. 1 and 2 were first aligned with the GeneWorks program (intelligenetics, Inc.). The PAUP program (David L. Swofford, Illinois Natural History Survey, Champaign, Ill.) was then used to construct phylogenetic tree illustrating relationship among U.S. isolates of PRRSV.

The phylogenetic tree of FIG. 3 was constructed by maximum parsimony methods with the aid of the PAUP software package version 3.1.1. The branch with the shortest length (most parsimonious) was found by implementing the exhaustive search option. The branch lengths (numbers of amino acid substitutions) are given above each branch. The sequences used in the analysis are LV, VR 2385, VR 2332, ISU 79 and ISU 1894.

The phylogenetic tree indicates that at least three groups of variants (or minor genotypes) exist within the major U.S. PRRSV genotype. The least virulent U.S. PRRSV isolate ISU 3927 forms a branch distinct from other U.S. isolates (FIG. 3). Isolates ISU 22, ISU 79, ISU 1894, and VR 2332 form another branch, representing a second minor genotype. The third minor genotype is represented by isolates ISU 79 and VR 2385 (FIG. 3). A very similar tree was also obtained by analyzing the last 60 nucleotides of ORF 1b of the seven U.S. isolates presented in FIG. 1 (data not shown). Identical tree topology was also produced by the unweighted pair-group method with arithmetic mean (UPGMA) using the GeneWorks program (data not shown).

In summary, the different genotypes of PRRSV have been confirmed and further elucidated. At least three minor genotypes within the major genotype of U.S. PRRSV have been identified, based on an analysis of the sequence of ORFs 2 to 7. Genetic variations not only between the European PRRSV and the U.S. PRRSV but among the U.S. PRRSV isolates have also been further confirmed as well, indicating the heterogeneous nature of PRRSV. The least virulent U.S. PRRSV isolate ISU 3927 has unexpectedly high sequence variations in ORFs 2 to 4, as compared to other U.S. isolates.

TABLE 3

Nucleotide and deduced amino acid sequence identities (%) of ORFS 2 to 5 of PRRSV

| ORF 2 | VR2385 | ISU22 | ISU55 | ISU79 | ISU1894 | ISU3927 | VR2332 | LV |
|---|---|---|---|---|---|---|---|---|
| VR2385 | ** | 97 | 96 | 96 | 95 | 91 | 98 | 58 |
| ISU22 | 97 | ** | 96 | 98 | 96 | 93 | 99 | 59 |
| ISU55 | 98 | 97 | ** | 96 | 95 | 91 | 97 | 61 |
| ISU79 | 96 | 97 | 97 | ** | 96 | 91 | 98 | 60 |
| ISU1894 | 96 | 97 | 96 | 96 | ** | 93 | 96 | 57 |
| ISU3927 | 94 | 94 | 94 | 93 | 93 | ** | 93 | 58 |
| VR2332 | 97 | 98 | 97 | 98 | 97 | 94 | ** | 59 |
| LV | 65 | 66 | 66 | 67 | 66 | 65 | 66 | ** |
| ORF 3 | | | | | | | | |
| VR2385 | ** | 91 | 94 | 92 | 90 | 87 | 91 | 55 |
| ISU22 | 92 | ** | 93 | 96 | 96 | 88 | 98 | 56 |
| ISU55 | 94 | 93 | ** | 94 | 93 | 87 | 94 | 56 |
| ISU79 | 94 | 96 | 94 | ** | 95 | 87 | 96 | 56 |
| ISU1894 | 92 | 97 | 93 | 96 | ** | 86 | 96 | 55 |
| ISU3927 | 90 | 90 | 89 | 90 | 90 | ** | 87 | 55 |
| VR2332 | 93 | 98 | 94 | 97 | 97 | 90 | ** | 56 |
| LV | 64 | 63 | 62 | 63 | 63 | 61 | 63 | ** |
| ORF 4 | | | | | | | | |
| VR2385 | ** | 94 | 96 | 94 | 95 | 83 | 94 | 66 |
| ISU22 | 93 | ** | 94 | 97 | 99 | 93 | 98 | 66 |
| ISU55 | 96 | 94 | ** | 96 | 96 | 93 | 95 | 67 |
| ISU79 | 93 | 97 | 94 | ** | 98 | 92 | 96 | 66 |
| ISU1894 | 92 | 98 | 94 | 96 | ** | 93 | 98 | 66 |
| ISU3927 | 91 | 93 | 92 | 91 | 91 | ** | 92 | 67 |
| VR2332 | 94 | 99 | 95 | 97 | 98 | 92 | ** | 65 |
| LV | 66 | 66 | 63 | 65 | 66 | 65 | 65 | ** |
| ORF 5 | | | | | | | | |
| VR2385 | ** | 90 | 91 | 88 | 89 | 91 | 89 | 54 |
| ISU22 | 93 | ** | 90 | 94 | 96 | 92 | 97 | 52 |
| ISU55 | 94 | 92 | ** | 89 | 89 | 90 | 89 | 51 |
| ISU79 | 91 | 95 | 91 | ** | 95 | 89 | 94 | 53 |
| ISU1894 | 92 | 97 | 90 | 94 | ** | 91 | 96 | 53 |
| ISU3927 | 91 | 93 | 91 | 91 | 91 | ** | 91 | 55 |
| VR2332 | 93 | 98 | 91 | 95 | 97 | 92 | ** | 53 |
| LV | 63 | 63 | 63 | 61 | 62 | 63 | 63 | ** |

Note:
The amino acid sequence comparisons are presented in the upper right half, and the nucleotide sequence comparisons are presented in the lower left half.

Experiment 2

During the replication of PRRSV, six subgenomic mRNAs (sg mRNAs), in addition to the genomic RNA, are synthesized. These sg mRNAs were characterized in this experiment.

The sg mRNAs of PRRSV form a 3'-coterminal nested set in PRRSV-infected cells. Each of these sg mRNAs is polycistronic and contains multiple open reading frames, except for sg mRNA 7 (as shown by Northern blot analysis using ORF-specific probes). The sg mRNAs were not packaged into virions, and therefore, only the genomic RNA was detected in purified virions, suggesting that the encapsidation signal of PRRSV is likely localized in the ORF 1 region.

The numbers of sg mRNAs in PRRSV-infected cells varies among PRRSV isolates with differing virulence. An additional species of sg mRNA in some PRRSV isolates was shown in Experiment 1 above to be derived from the sequence upstream of ORF 4, and has been designated as sg mRNA 4-1.

The leader-mRNA junction sequences of sg mRNAs 3 and 4 of isolates ISU 79 and ISU 1894, as well as sg mRNA 4-1 of the isolate ISU 79, contain a common six nucleotide sequence motif, T(G)TA(G/C)ACC. Sequence analysis of the genomic RNA of these two U.S. isolates and comparison with Lelystad virus (LV) revealed heterogeneity of the leader-mRNA junction sequences among PRRSV isolates. The numbers, locations and the sequences of the leader-mRNA junction regions varied between U.S. isolates and LV, as well as among U.S. isolates. The last three nucleotides, ACC, of the leader-mRNA junction sequences are invariable. Variations were found in the first three nucleotides.

By comparing the 5'-terminal sequence of sg mRNA 4-1 with the genomic sequence of ISU 79 and ISU 1894, it was found that a single nucleotide substitution, from T in ISU 1894 to C in ISU 79, led to a new leader-mRNA junction sequence in ISU 79, and therefore, an additional species of sg mRNA (sg mRNA 4-1). A small ORF, designated as ORF 4-1, with a coding capacity of 45 amino acids was identified at the 5'-end of sg mRNA 4-1.

Materials and Methods

Viruses and cells. The PRRSV isolates used (ISU 22, ISU 55, ISU 79, ISU 1894 and ISU 3927) were isolated from pig lungs obtained from different farms in Iowa. A continuous cell line, ATCC CRL 11171, was used for isolation and growth (culturing) of viruses. These PRRSV isolates were biologically cloned by three rounds of plaque purification and grown on the CRL 11171 cells. All of the virus isolates used in this study were at the seventh passage.

ISU 22 and ISU 79 are highly pathogenic and produce from 50 to 80% consolidation of the lung tissues in experimentally-infected five-week-old caesarean-derived colostrum-deprived pigs necropsied at 10 days post-inoculation. By contrast, ISU 55, ISU 1894 and ISU 3927 are of low pathogenicity and produce only 10 to 25% consolidation of lung tissues in the same experiment (U.S. application Ser. Nos. 08/131,625 and 08/301,435).

Preparation of virus-specific total intracellular RNAs, poly (A)$^+$ RNA and virion RNA. Confluent monolayers of CRL 11171 cells were infected with different isolates of PRRSV at the seventh passage at a multiplicity of infection (m.o.i.) of 0.1. PRRSV-specific total intracellular RNAs were isolated from PRRSV-infected cells by a conventional guanidinium isothiocyanate method (Stratagene). The poly (A)$^+$ RNA was enriched from the total intracellular RNAs by oligo (dT)-cellulose column chromatography (Invitrogen).

For isolation of PRRSV virion RNA, confluent CRL 11171 cells were infected with isolate ISU 3927 of PRRSV at a m.o.i. of 0.1. When more than 70% of the infected cells showed a cytopathic effect, the cultures were frozen and thawed three times, and the culture medium was clarified at 1200×g for 20 min. at 4° C. The virus was then precipitated with polyethylene glycol and subsequently purified by cesium chloride gradient centrifugation as described in U.S. application Ser. No. 08/131,625. The purified virus was treated with RNase A at a final concentration of 20 μ/ml for 90 min. at 37° C. The virus was then pelleted, and the virion RNA was isolated using a conventional guanidinium isothiocyanate method.

cDNA synthesis and polymerase chain reaction. cDNA was synthesized from total intracellular RNAs by reverse transcription using random primers and amplified by the polymerase chain reaction (RT-PCR) as described previously (Meng et al., 1993, J. Vet. Diagn. Invest., 5:254–258).

Northern blot analyses. Ten μg of total intracellular RNAs from virus infected cells and mock-infected cells were used per lane in a formaldehyde-agarose gel. For separation of poly (A)$^+$ RNA and virion RNA, fifteen ng of virion RNA and 0.2 μg of poly (A)$^+$ RNA were loaded per lane. The RNA was denatured with formaldehyde according to a conventional method (Sambrook et al, "Molecular Cloning: A Laboratory Manual", 2nd ed., Cold Spring Harbor Laboratory, Cold Spring Harbor, N.Y.). Electrophoretic separation of RNA, RNA blotting, and hybridization were performed as described in U.S. application Ser. No. 08/131,625. In some experiments, glyoxal-DMSO agarose gels were also performed as described in U.S. application Ser. No. 08/131,625.

For preparation of probes, a specific cDNA fragment from each of the ORFs 1b to 7 was generated by RT-PCR with ORF-specific primers. The primers were designed in such a way that each primer pair amplifies only a specific fragment of a given ORF, and the overlapping, neighboring ORFs are not included in any given cDNA probe. The primer pairs for generating cDNA probes representing ORFs 1b through 7 are IM729/IM782 for ORF 1b, IM312/IM313 for ORF 2, XM1022/IM258 for ORF 3, XM1024/XMI 023 for ORF 4, PP287/PP286 for ORF 5, PP289/XM780 for ORF 6, and PP285/PP284 for ORF 7 (Table 4).

Cloning, sequencing and nucleotide sequence analyses. Primers for RT-PCR were designed on the basis of PRRSV isolate VR 2385 sequences, which amplified the entire protein coding regions of ORFs 2 to 5 of PRRSV isolates ISU 79 and ISU 1894. Primers JM259 and JM260 were used for amplification of ORFs 4 and 5, and XM992 and XM993 for amplification of ORFs 2 and 3 (Table 4). Unique restriction sites (EcoRI and BamHI) at the termini of the PCR products were introduced, thus enabling a cassette approach to replacement of these ORFs.

The PCR products of ORFs 2–3 and ORFs 4–5 of ISU 79 and ISU 1984 were each digested with EcoRI and BamHI, then purified and cloned into vector pSK+ as described previously (Meng et al., 1993, J. Vet. Diagn. Invest., 5:254–258). Plasmids containing viral inserts were sequenced with a conventional automated DNA sequencer (Applied Biosystem, Inc.). At least three cDNA clones representing the entire sequence of ORFs 2 to 5 from each virus isolate were sequenced with universal and reverse primers, as well as other virus-specific sequencing primers (XM969, XM970, XM1006, XM078 and XM077; see Table 4).

To determine the leader-mRNA junction sequences of sg mRNAs 3, 4 and 4-1, primer pair IM755 and DP586 (Table 4) was used for RT-PCR to amplify the corresponding 5'-terminal sequences. The resulting PCR products were purified and sequenced by direct PCR sequencing using virus specific primers XMD77 and XM141 (Table 4). The sequences were combined and analyzed by MacVector (International Biotechnologies, Inc.) and GeneWorks (IntelliGenetics, Inc) computer software programs.

Oligonucleotides. The synthetic oligonucleotides used in this study were summarized in Table 4. These oligonucleotides were synthesized as single stranded DNA using an automated DNA synthesizer (Applied Biosystem) and purified by high pressure liquid chromatography (HPLC).

Results

Sg mRNAs are not packaged into PRRSV virions. To determine whether the sg mRNAs of PRRSV are packaged, virions of PRRSV isolate ISU 3927 were purified by CsCl gradient. The purified virions were treated with RNase A before pelleting the virion and extracting RNA, to remove any RNA species which may have adhered to the virion surface. RNAs from RNase A-treated virions along with the total intracellular RNAs from isolate ISU 3927 of PRRSV-infected cells were separated in a formaldehyde gel and hybridized with a probe generated from the 3'-terminal sequence of the viral genome by PCR with primers PP284 and PP285 (U.S. application Ser. No. 08/131,625; Table 4).

Figure 4:
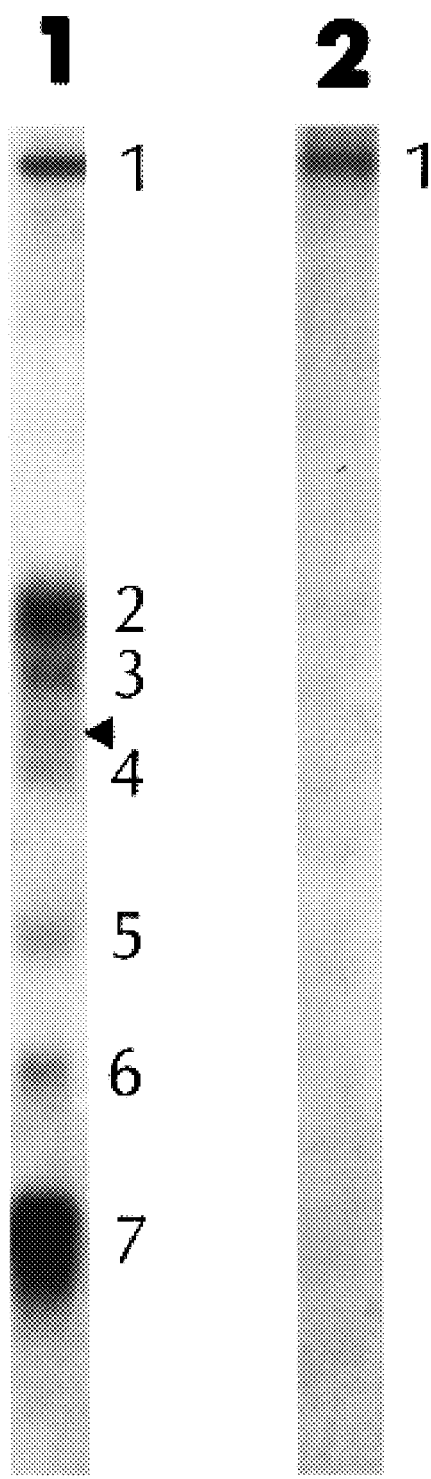
FIG. 4 shows a Northern blot analysis of RNAs isolated from ISU 3927-infected CRL 11171 cells (lane 1) and from purified virions of ISU 3927 (lane 2)

Only the genomic RNA was detected in the purified virions of PRRSV isolate ISU 3927 (FIG. 4), and no detectable amounts of sg mRNAs were observed in the purified virions even after 3 weeks exposure. In contrast, seven species of sg mRNAs, in addition to the genomic RNA, were detected in ISU 3927-infected cells (FIG. 4). Similar results were observed with two other U.S. isolates, ISU 55 and ISU 79.

Variation in the numbers of the sg mRNAs among U.S. PRRSV isolates with differing virulence. All arteriviruses known prior to the present invention, including U.S. PRRSV and European PRRSV, have been shown to produce six sg mRNAs, except for three LDV variants (LDV-P, LDV-a and LDV-v), which synthesize seven sg mRNAs. However, a nested set of six sg mRNAs is produced in the LDV-C strain.

To compare if there are any variations in the sg mRNAs among U.S. PRRSV isolates, confluent monolayers of CRL 11171 cells were infected with five different isolates of U.S. PRRSV with differing virulence at a m.o.i. of 0.1. Total intracellular RNAs were isolated from virus-infected cells at 24 h post-infection. A cDNA fragment was generated from the extreme 3'-end of the viral genome by PCR with primers PP284 and PP285 (Table 4). The cDNA fragment was labelled with $^{32}$P-dCTP by the random primer extension method, and hybridized with the total intracellular RNAs (separated on a formaldehyde gel).

Figure 5:
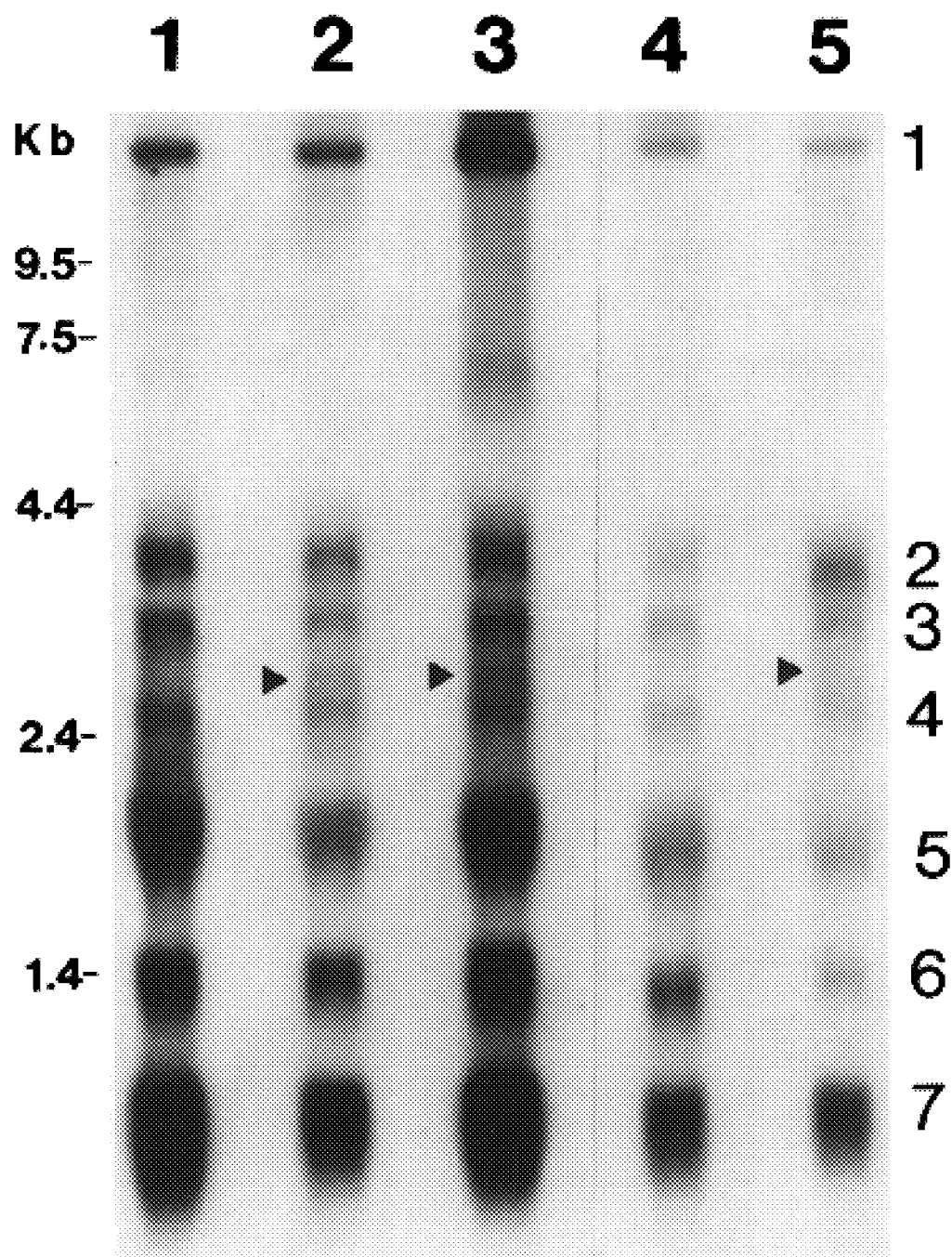
FIG. 5 shows a Northern blot analysis of total intracellular RNAs isolated from CRL 11171 cells infected with ISU22 (lane 1), ISU 55 (lane 2), ISU 79 (lane 3), ISU 1894 (lane 4) and ISU 3927 (lane 5), respectively.

Analyses of the RNAs showed that a nested set of six or more sg mRNAs, in addition to the genomic RNA, was present in cells infected with one of the five isolates of U.S. PRRSV with differing virulence (FIG. 5). Similar results were obtained when the total intracellular RNAs were separated on a glyoxal-DMSO agarose gel. PRRSV isolates ISU 55, ISU 79 and ISU 3927 produced seven easily distinguishable sg mRNAs, whereas isolates ISU 22 and ISU 1894 produced six sg mRNAs (FIG. 5). The U.S. PRRSV isolate VR 2385 also produces six sg mRNAs (U.S. application Ser. No. 08/131,625). An additional species of sg mRNA was located between sg mRNAs 3 and 4, and was designated as sg mRNA 4-1. The sg mRNAs differed little, if any, in size among the five isolates of PRRSV (FIG. 5). There appears to be no correlation, however, between the pneumovirulence and the numbers of the sg mRNAs observed in these five isolates.

Sg mRNA 4-1 is not a defective-interfering RNA and is not a result of nonspecific binding of the probes to ribosomal RNAs. It has been shown that, in coronaviruses, a variety of defective interfering RNA (DI RNA) of different sizes were generated when MHV was serially passaged in tissue culture at a high m.o.i. DI RNAs were also observed in cells infected with torovirus during undiluted passage. Therefore, the possibility of sg mRNA 4-1 of PRRSV being a DI RNA was investigated.

To exclude this possibility, the original virus stock of PRRSV isolate ISU 79, which produces the additional species of sg mRNA 4-1, was passaged four times in CRL 11171 cells at different m.o.i. of 0.1, 0.01 and 0.001, respectively. In a control experiment, four undiluted passages of the original virus stock of ISU 79 were performed. After four passages, total intracellular RNAs were isolated from virus-infected cells and Northern blot analysis was repeated with the same probe generated from the extreme 3'-end of the viral genome.

Analyses of the sg mRNAs showed that the additional species of sg mRNA 4-1 was still present in all RNA preparations with different m.o.i., as well as in RNA preparations from undiluted passages (FIG. 6A). Moreover, there was no interference or reduction in the synthesis of other sg mRNAs in the presence of sg mRNA 4-1, as is usually the case with DI RNA.

It has been demonstrated that the DI RNAs of MHV disappeared after two high-dilution passages. Therefore, if the original virus stock of ISU 79 contained DI RNA, then the DI RNA should disappear after four high-dilution passages. The experimental data above suggests that, unlike DI RNA, the replication of sg mRNA 4-1 is independent of the amount of standard virus. Thus, sg mRNA 4-1 is not a DI RNA.

In Northern blot analysis of total intracellular RNAS, the probes may nonspecifically bind to the 18S and 28S ribosomal RNAs, which are abundant in total cytoplasmic RNA preparations. Alternatively, the abundant ribosomal RNAs may cause retardation of virus-specific sg mRNAs which may co-migrate corrugate with the ribosomal RNAs in the gel.

Two additional bands due to the nonspecific binding of probes to the ribosomal RNAs have been observed in LV-infected cells and LDV-infected cells. Therefore, it is possible that sg mRNA 4-1 of PRRSV is due to the nonspecific binding of probes to the ribosomal RNAs.

To rule out this possibility, polyadenylated RNA was isolated from total intracellular RNAs of CRL 11171 cells infected with either of two PRRSV isolates, ISU 55 and ISU 79. Both ISU 55 and ISU 79 produce the additional species of sg mRNA 4-1 (FIG. 5). Northern blot analysis of the polyadenylated RNA showed that the additional species of sg mRNA 4-1 in cells infected with either of these two isolates was still present (FIG. 6B), indicating that sg mRNA 4-1 is not due to the nonspecific binding of a probe to the ribosomal RNAS.

The sg mRNAs represent a 3'-coterminal nested set and the sg mRNA 4-1 is derived from the sequence upstream of ORF 4. Six sg mRNAs, in addition to the genomic RNA, are detected in cells infected with VR 2385 using a cDNA probe from the extreme 3'-end of the viral genome (U.S. application Ser. No. 08/131,625). Thus, like Berne virus (BEV), LDV, EAV, coronaviruses and LV, the replication of U.S. PRRSV also requires the synthesis of a 3'-coterminal nested set of sg mRNAs (U.S. application Ser. Nos. 08/131,625 and 08/301,435).

To analyze these sg mRNAs in more detail, seven cDNA fragments specific for each of ORFs 1b through 7 were amplified by PCR. The design of primers for PCR was based on the sequence of VR 2385. The sequences and locations of the primers, IM729 and IM782 for ORF 1b, IM312 and IM313 for ORF 2, XM1022 and IM258 for ORF 3, XM1024 and XM1023 for ORF 4, PP286 and PP287 for ORF 5, PP289 and XM780 for ORF 6, and PP284 and PP285 for ORF 7 and the 3' noncoding region (NCR), are shown in Table 4. The primers were designed in such a way that each set of primers will only amplify a fragment from a particular ORF, and the overlapping sequences between neighboring ORFs are not included in any given fragment. Therefore, each of these seven DNA fragments represents only one particular ORF except for fragment 7, which represents both ORF 7 and the 3'-NCR.

These seven DNA fragments were labeled with $^{32}$P-dCTP and hybridized to Northern blots of total intracellular RNAs extracted from cells infected with either of two U.S. isolates of PRRSV, ISU 1894 and ISU 79. Total intracellular RNAs isolated from mock-infected CRL 11171 cells were included as a control.

Figure 7A:
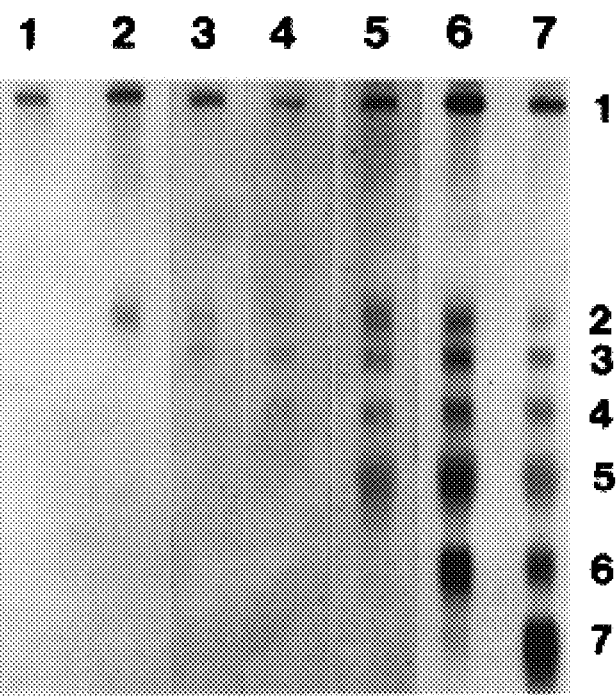
FIGS. 7A and 7B show a Northern blot analysis of total intracellular mRNAs isolated from CRL 11171 cells infected with ISU 1894 (A) and ISU 79 (B)
Figure 7B:
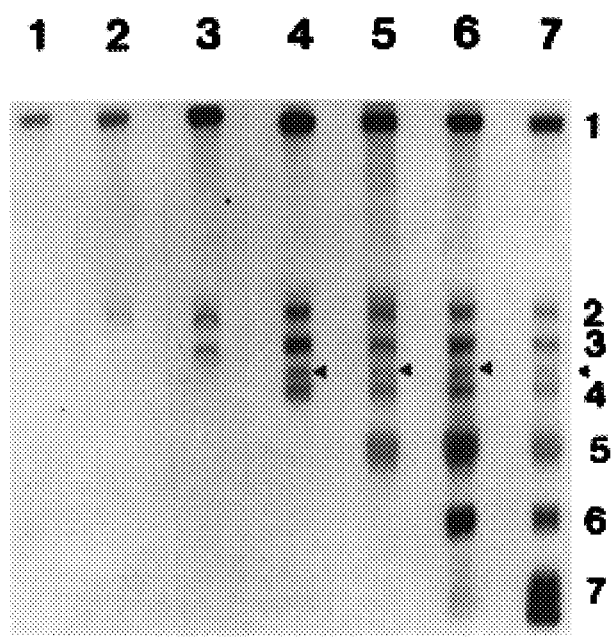

Northern blot analyses showed that Probe 1, generated from ORF 1b, hybridized only with the genomic RNA. Probes 2 through 7 each hybridized with one more additional RNA species besides the genomic RNA (FIG. 7). The results indicate that a 3'-coterminal nested set of six (ISU 1894) or more (ISU 79) sg mRNAs is formed in PRRSV-infected cells (FIGS. 7A and 7B), with the smallest 3'-terminal RNA (sg mRNA 7) encoding ORF 7. The sg mRNAs of U.S. PRRSV all contain the 3'-end of the genomic RNA, but extend for various distances towards the 5'-end of the genome, depending on the size of the given sg mRNA.

The sg mRNA 4-1 of PRRSV isolate ISU 79 hybridized with probes 4 through 7, but not with probes 1, 2 and 3 (FIG. 7B), suggesting that sg mRNA 4-1 contains ORFs 4 through 7 as well as the 3'-NCR. Therefore, sg mRNA 4-1 is generated from the sequence upstream of ORF 4.

A single nucleotide substitution leads to the acquisition of the additional species of sg mRNA 4-1. Northern blot hybridization data showed that sg mRNA 4-1 is derived from the sequence upstream of ORF 4 (FIG. 7B). To determine the exact location and the leader-mRNA junction sequence of sg mRNA 4-1, a set of primers, IM755 and DP586, was designed (Table 4). The forward primer IM755 was based on the 3'-end of the leader sequence of VR 2385, and the reverse primer DP586 is located in ORF 4 (Table 4).

RT-PCR with primers IM755 and DP586 was performed using total intracellular RNAs isolated from cells infected with either of ISU 1894 or ISU 79. ISU 79 produces sg mRNA 4-1, but ISU 1894 does not (FIG. 5). A 30-second PCR extension time was applied to preferentially amplify the short fragments representing the 5'-terminal sequences of sg mRNAs 3, 4 and 4-1.

Figures 8A, 8B:
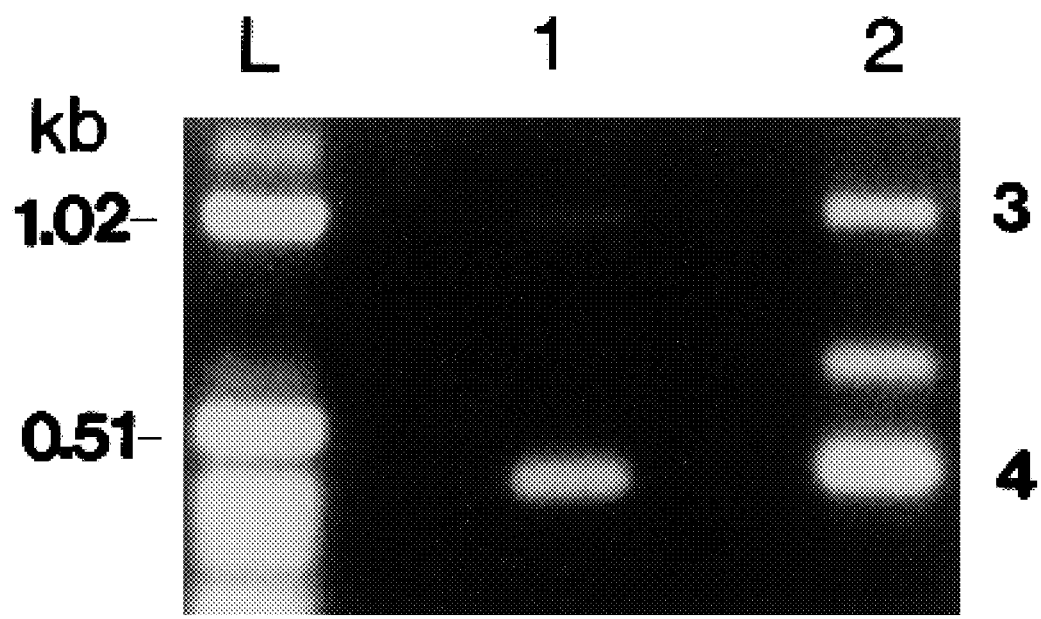
FIGS. 8A and 8B show RT-PCR amplification of the 5'-terminal sequences of the sg mRNAs 3 and 4 of ISU 1894 (lane 1) and sg mRNAs 3, 4 and 4-1 of ISU 79 (lane 2) (A) where lane L is a 1-kb marker; and the leader-mRNA junction sequences of sg mRNAs 3 and 4 of ISU 79 and ISU 1894 and of sg mRNA 4-1 of ISU 79 (B), where the locations of the leader-mRNA junction sequences in the genomes relative to the start codon of each ORF were indicated by minus (−) numbers of nucleotides upstream of the ORFs.

Analysis of the RT-PCR products showed that two fragments with sizes of about 1.1 kb and 0.45 kb were amplified from the total RNAs of ISU 1894 virus-infected cells (FIG. 8A). These two fragments represent 5'-portions of sg mRNAs 3 and 4, respectively. In addition to the two fragments observed in the isolate of ISU 1894, a third fragment of about 0.6 kb representing the 5'-portion of sg mRNA 4-1 was also amplified from total RNAs of cells infected with ISU 79 (FIG. 8A).

To determine the leader-mRNA junction sequences of sg mRNAs 3, 4 and 4-1, the RT-PCR products of ISU 79 and ISU 1894 were purified from an agarose gel using a GENECLEAN kit (Bio 101, Inc.), and sequenced directly with an automated DNA Sequencer (Applied Biosystems). The primers used for sequencing the 5'-end of the RT-PCR products (XM141 and XM077, Table 4) were designed on the basis of the genomic sequences of ISU 79 and ISU 1894 (FIG. 9). The leader-mRNA junction sequences (in which the leader joins the mRNA body during the synthesis of sg mRNAs) of sg mRNAs 3, 4, and 4-1 of the two U.S. PRRSV isolates were determined by comparing the sequences of the 5'-end of the sg mRNAs and the genomic RNA of the two isolates (FIG. 8B).

The leader-mRNA junction sequences of sg mRNAs 3 and 4 of ISU 1894 and ISU 79 were identical. For sg mRNA 3, the leader-junction sequence (GUAACC) is located 89 nucleotides upstream of ORF 3. For sg mRNA 4, UU<u>CACC</u> is located 10 nucleotides upstream of ORF 4 (FIG. 8B and FIG. 9). The leader-mRNA junction sequence of sg mRNA 4-1 of ISU 79 is UU<u>GACC</u>, located 236 nucleotides upstream of ORF 4 (FIGS. 8B and 9).

Sequence alignment of the genomic sequences of ISU 79 and ISU 1894 shows that a single nucleotide substitution, from T in ISU 1894 to C in ISU 79, leads to the acquisition of an additional leader-mRNA junction sequence, UU<u>GACC</u>, in ISU 79 (FIGS. 8B and 9). Therefore, an additional species of sg mRNA (4-1) is formed (FIG. 5). In addition to ORFs 4 to 7 contained within sg mRNA 4, sg mRNA 4-1 contains at the 5'-end an additional small ORF (ORF 4-1) with a coding capacity of 45 amino acids (FIG. 9). This small ORF stops just one nucleotide before the start codon of ORF 4.

Sequence analyses of ORFs 2 to 7 of two U.S. isolates reveal heterogeneity of the leader mRNA junction sequences. ORFs 2 to 5 of ISU 79 and ISU 1894 were cloned and sequenced (see Experiment 1 above). ISU 79 produces seven easily distinguishable sg mRNAs, whereas ISU 1894 produces six distinguishable sg mRNAs (FIGS. 5 and 7). At least three cDNA clones at any given region of ORFs 2 to 5 were sequenced for each virus isolate, using universal and reverse primers as well as virus-specific primers XM969, XM970, XM1006, XM078, and XM077 (Table 4). The sequences of ORFs 6 and 7 of ISU 1894 and ISU 79 are disclosed in U.S. application Ser. No. 08/301,435.

Sequence analysis showed that the ORFs 2 to 7 of ISU 79 and ISU 1894 overlap each other except for a 10-nucleotide noncoding region between ORF 4 and ORF 5. The same observation was previously made for VR 2385 (U.S. application Ser. No. 08/301,435). This is very unusual, since all members of the proposed Arteriviridae family, including LV, contain overlapping ORFs. However, the ORFs of coronaviruses are separated by intergenic noncoding sequences. Therefore, U.S. PRRSV appears to be somewhat similar to the coronaviruses in terms of the genomic organization in junction regions of ORFs 4 and 5.

ORF 2 of ISU 1894 was one amino acid longer than that of ISU 79 (FIG. 9). The stop codon of ORF 2, TAG, was changed to TGG in ISU 1894 immediately followed by a new stop codon (TGA) in ISU 1894 (FIG. 9). The sizes of other ORFs of ISU 79 and ISU 1894 were identical (FIG. 9). There were no deletions or insertions in ORFs 2 to 7 of these isolates. However, numerous substitutions are present throughout the entire sequence of ORFs 2 to 7 between ISU 79 and ISU 1894 (FIG. 9).

The numbers and locations of the determined or predicted leader-mRNA junction sequences varied between ISU 1894 and ISU 79 (FIG. 9). In addition to the regular leader-mRNA 4 junction sequence, TTCACC, 10 nucleotides upstream of ORF 4, there was an additional leader-mRNA 4-1 junction sequence (TTGACC) located 236 nucleotides upstream of ORF 4 in ISU 79 (FIG. 9). The leader-mRNA junction sequences of sg mRNAs 4 and 4-1 were separated by 226 nucleotides, which correlated with the estimated sizes of sg mRNAs 4 and 4-1 observed in Northern blot analysis (FIG. 5) and RT-PCR amplification (FIG. 8A).

The leader-mRNA 3 junction sequence is identical between ISU 1894 and ISU 79, GTAACC, located 89 nucleotides upstream of ORF 3. The predicted leader-mRNA junction sequences of sg mRNAs 2 and 6 of ISU 1894 and ISU 79 were also the same (FIG. 9).

However, the predicted leader-mRNA 5 junction sequences of ISU 1894 and ISU 79 are different (FIG. 9). There are 3 potential leader-mRNA 5 junction sequences for ISU 79 (GCAACC, GAGACC and TCGACC, located 55, 70 and 105 nucleotides upstream of ORF 5, respectively). Two potential leader-mRNA 5 junction sequences were also found in ISU 1894 (GAAACC and TCGACC, located 70 and 105 nucleotides upstream of ORF 5, respectively) (FIG. 9). The differences were due to the two-nucleotide substitutions in the predicted leader-mRNA 5 junction sequences of these isolates (FIG. 9).

In addition to the leader-mRNA 7 junction sequence 15 nucleotides upstream of ORF 7, an additional leader-mRNA 7 junction sequence was found (ATAACC), located 129 nucleotides upstream of ORF 7 in each of these two isolates (FIG. 9). However, the sg mRNA corresponding to this additional leader-mRNA 7 junction sequence was not clearly distinguishable from the abundant sg mRNA 7 which produced a widely-diffused band in the Northern blot (FIGS. 5, 6 and 7).

Variations in the numbers and locations of the leader-mRNA junction sequences between LV and the two U.S. isolates analyzed in this experiment were also found by comparing the leader-mRNA junction sequences of LV with those of the two U.S. isolates ISU 1894 and ISU 79. Taken together, these data indicate that the sg mRNAs of PRRSV are polymorphic, and the numbers and the exact sizes of the sg mRNAs depend on the particular PRRSV isolate analyzed. However, a nested set of six sg mRNAs most likely reflects the standard arterivirus genome organization and transcription.

TABLE 4

Synthetic oligonucleotides used in Experiment 2

| Olig Name | Sequence | | Location (nucleotides)[a] | Polarity[b] |
|---|---|---|---|---|
| IM729 | 5'-GACTGATGGTCTGGAAAG-3' | (SEQ ID NO: 78) | ORF1b, −507 to −490 upstream of ORF2 | + |
| IM782 | 5'-CTGTATCCGATTCAAACC-3' | (SEQ ID NO: 79) | ORF1b, −180 to −163 upstream of ORF2 | − |
| IM312 | 5'-AGGTTGGCTGGTGGTCTT-3' | (SEQ ID NO: 80) | ORF2, 131 to 148 downstream of ORF2 | + |
| IM313 | 5'-TCGCTCACTACCTGTTTC-3' | (SEQ ID NO: 81) | ORF2, 381 to 398 downstream of ORF2 | − |
| XM1022 | 5'-TGTGCCCGCCTTGCCTCA-3' | (SEQ ID NO: 82) | ORF3, 168 to 175 downstream of ORF3 | + |
| IM268 | 5'-AAACCAATTGCCCCCGTC-3' | (SEQ ID NO: 83) | ORF3, 520 to 537 downstream of ORF3 | − |
| XM1024 | 5'-TATATCACTGTCACAGCC-3' | (SEQ ID NO: 84) | ORF4, 232 to 249 downstream of ORF4 | + |
| XM1023 | 5'-CAAATTGCCAACAGAATG-3' | (SEQ ID NO: 85) | ORF4, 519 to 536 downstream of ORF4 | − |
| PP287 | 5'-CAACTTGACGCTATGTGACG-3' | (SEQ ID NO: 86) | ORF5, 129 to 148 downstream of ORF5 | + |
| PP286 | 5'-GCCGCGGAACCATCAAGCAC-3' | (SEQ ID NO: 87) | ORF5, 538 to 667 downstream of ORF5 | − |
| PP289 | 5'-GACTGCTAGGGCTTCTGCAC-3' | (SEQ ID NO: 88) | ORF6, 119 to 138 downstream of ORF6 | + |
| XM780 | 5'-CGTTGACCGTAGTGGAGC-3' | (SEQ ID NO: 89) | ORF6, 416 to 433 downstream of ORF6 | − |
| PP285 | 5'-CCCCATTTCCCTCTAGCGACTG-3' | (SEQ ID NO: 90) | ORF7, 157 to 178 downstream of ORF7 | + |
| PP284 | 5'-CGGCCGTGTGGTTCTCGCCAAT-3' | (SEQ ID NO: 91) | 3'-NCR, −27 to −6 upstream of poly (A) | − |
| JM260 | 5'-GGGGAATTCGGGATAGGGAATGTG-3' | (SEQ ID NO: 69) | ORF3, 338 to 356 downstream of ORF3 | + |
| JM259 | 5'-GGGGATCCTTTTGTGGAGCCGT-3' | (SEQ ID NO: 68) | ORF6, 34 to 52 downstream of ORF6 | − |
| XM993 | 5'-GGTGAATTCGTTTTATTTCCCTCCGGG-3' | (SEQ ID NO: 72) | ORF1b, −53 to −35 upstream of ORF2 | + |
| XM992 | 5'-GGGGGATCCTGTTGGTAATAG/AGTCTG-3' | (SEQ ID NO: 70–71) | ORF3, −50 to −34 upstream of ORF4 | − |
| XM970 | 5'-GGTTTCACCTAGAATGGC-3' | (SEQ ID NO: 74) | ORF2, 522 to 550 downstream of ORF2 | + |
| XM969 | 5'-GATAGAGTCTGCCCTTAG-3' | (SEQ ID NO: 73) | ORF5, 443 to 460 downstream of ORF6 | − |
| XM1006 | 5'-GCTTCTGAGATGAGTGA-3' | (SEQ ID NO: 75) | ORF4, 316 to 332 downstream of ORF4 | + |
| XM078 | 5'-CTGAGCAATTACAGAAG-3' | (SEQ ID NO: 77) | ORF2, 202 to 218 downstream of ORF2 | + |
| XM077 | 5'-CAACCAGGCGTAAACACT-3' | (SEQ ID NO: 76) | ORF3, 316 to 333 downstream of ORF3 | − |
| IM755 | 5'-GACTGCTTTACGGTCTCTC-3' | (SEQ ID NO: 92) | Leader, 3' end of the Leader sequence | + |
| DP586 | 5'-GATGCCTGACACATTGCC-3' | (SEQ ID NO: 93) | ORF4, 355 to 372 downstream of ORF4 | − |
| XM141 | 5'-CTGCAAGACTCGAACTGAA-3' | (SEQ ID NO: 94) | ORF4 78 to 97 downstream of ORF4 | − |

Obviously, numerous modifications and variations of the present invention are possible in light of the above teachings. It is therefore to be understood that within the scope of the appended claims, the invention may be practiced otherwise than as specifically described herein.

SEQUENCE LISTING (1) GENERAL INFORMATION:

(iii) NUMBER OF SEQUENCES: 95

(2) INFORMATION FOR SEQ ID NO:1:

(i) SEQUENCE CHARACTERISTICS:
       (A) LENGTH: 2352 base pairs
       (B) TYPE: nucleic acid
       (C) STRANDEDNESS: unknown
       (D) TOPOLOGY: unknown (ii) MOLECULE TYPE: cDNA (vi) ORIGINAL SOURCE:
       (A) ORGANISM: Porcine reproductive and respiratory virus
       (B) STRAIN: Iowa
       (C) INDIVIDUAL ISOLATE: VR2385

(xi) SEQUENCE DESCRIPTION: SEQ ID NO:1:

```
CCTGTCATTG AACCAACTTT AGGCCTGAAT TGAGATGAAA TGGGGTCTAT GCAAAGCCTT      60

TTTGACAAAA TTGGCCAACT TTTTGTGGAT GCTTTCACGG AGTTCTTGGT GTCCATTGTT     120

GATATCATTA TATTTTTGGC CATTTTGTTT GGCTTCACCA TCGCAGGTTG GCTGGTGGTC     180

TTTTGCATCA GATTGGTTTG CTCCGCGATA CTCCGTGCGC GCCCTGCCAT TCACTCTGAG     240

CAATTACAGA AGATCCTATG AGGCCTTTCT CTCTCAGTGC CAGGTGGACA TTCCCACCTG     300

GGGAACTAAA CATCCTTTGG GGATGCTTTG GCACCATAAG GTGTCAACCC TGATTGATGA     360

AATGGTGTCG CGTCGAATGT ACCGCATCAT GGAAAAAGCA GGACAGGCTG CCTGGAAACA     420

GGTAGTGAGC GAGGCTACGC TGTCTCGCAT TAGTAGTTTG GATGTGGTGG CTCATTTTCA     480

GCATCTTGCC GCCATTGAAG CCGAGACCTG TAAATATCTG GCCTCTCGGC TGCCCATGCT     540

ACACCACCTG CGCATGACAG GGTCAAATGT AACCATAGTG TATAATAGTA CTTTGAATCA     600

GGTGTTTGCT GTTTTCCCAA CCCCTGGTTC CCGGCCAAAG CTTCATGATT CCAGCAATG     660

GCTAATAGCT GTACATTCCT CTATATTTTC CTCTGTTGCA GCTTCTTGTA CTCTTTTTGT     720

TGTGCTGTGG TTGCGGGTTC CAATGCTACG TACTGTTTTT GGTTTCCGCT GGTTAGGGGC     780

AATTTTTCTT TCGAACTCAC GGTGAATTAC ACGGTGTGCC CGCCTTGCCT CACCCGGCAA     840

GCAGCCGCAG AGGCCTACGA ACCCGGCAGG TCCCTTTGGT GCAGGATAGG GCATGATCGA     900

TGTGGGAGG ACGATCATGA TGAACTAGGG TTTGTGGTGC CGTCTGGCCT CTCCAGCGAA     960

GGCCACTTGA CCAGTGCTTA CGCCTGGTTG GCGTCCCTGT CCTTCAGCTA TACGGCCCAG    1020

TTCCATCCCG AGATATTCGG GATAGGGAAT GTGAGTCGAG TCTATGTTGA CATCAAGCAC    1080

CAATTCATTT GCGCTGTTCA TGATGGGCAG AACACCACCT TGCCCCACCA TGACAACATT    1140

TCAGCCGTGC TTCAGACCTA TTACCAGCAT CAGGTCGACG GGGCAATTG GTTTCACCTA    1200

GAATGGGTGC GTCCCTTCTT TTCCTCTTGG TTGGTTTTAA ATGTCTCTTG GTTTCTCAGG    1260

CGTTCGCCTG CAAGCCATGT TTCAGTTCGA GTCTTTCAGA CATCAAGACC AACACCACCG    1320

CAGCGGCAGG CTTTGCTGTC CTCCAAGACA TCAGTTGCCT TAGGCATCGC AACTCGGCCT    1380

CTGAGGCGAT TCGCAAAGTC CCTCAGTGCC GCACGGCGAT AGGACACCC GTGTATATCA    1440

CTGTCACAGC CAATGTTACC GATGAGAATT ATTTGCATTC CTCTGATCTT CTCATGCTTT    1500

CTTCTTGCCT TTTCTATGCT TCTGAGATGA GTGAAAAGGG ATTTAAGGTG GTATTTGGCA    1560

ATGTGTCAGG CATCGTGGCA GTGTGCGTCA ACTTCACCAG TTACGTCCAA CATGTCAAGG    1620
```

-continued

```
AATTTACCCA ACGTTCCTTG GTAGTTGACC ATGTGCGGCT GCTCCATTTC ATGACGCCCG   1680
AGACCATGAG GTGGGCAACT GTTTTAGCCT GTCTTTTTAC CATTCTGTTG GCAATTTGAA   1740
TGTTTAAGTA TGTTGGGGAA ATGCTTGACC GCGGGCTGTT GCTCGCAATT GCTTTTTTTA   1800
TGGTGTATCG TGCCGTCTTG TTTTGTTGCG CTCGTCAGCG CCAACGGGAA CAGCGGCTCA   1860
AATTTACAGC TGATTTACAA CTTGACGCTA TGTGAGCTGA ATGGCACAGA TTGGCTAGCT   1920
AATAAATTTG ACTGGGCAGT GGAGTGTTTT GTCATTTTTC CTGTGTTGAC TCACATTGTC   1980
TCTTATGGTG CCCTCACTAC TAGCCATTTC CTTGACACAG TCGGTCTGGT CACTGTGTCT   2040
ACCGCTGGGT TTGTTCACGG GCGGTATGTT CTGAGTAGCA TGTACGCGGT CTGTGCCCTG   2100
GCTGCGTTGA TTTGCTTCGT CATTAGGCTT GCGAAGAATT GCATGTCCTG GCGCTACTCA   2160
TGTACCAGAT ATACCAACTT TCTTCTGGAC ACTAAGGGCA GACTCTATCG TTGGCGGTCG   2220
CCTGTCATCA TAGAGAAAAG GGGCAAAGTT GAGGTCGAAG GTCACCTGAT CGACCTCAAA   2280
AGAGTTGTGC TTGATGGTTC CGCGGCTACC CCTGTAACCA GAGTTTCAGC GGAACAATGG   2340
AGTCGTCCTT AG                                                       2352
```

(2) INFORMATION FOR SEQ ID NO:2:

(i) SEQUENCE CHARACTERISTICS:
(A) LENGTH: 2349 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory virus
(B) STRAIN: Iowa
(C) INDIVIDUAL ISOLATE: ISU3927

(xi) SEQUENCE DESCRIPTION: SEQ ID NO:2:

```
CCTATCATTG AACCAACTTT GGGTCTAGAC TGAAATGCAA TGGGGTCCAT GCAAAGCCTT     60
TTTGACAAGA TCGGTCAACT TTTTGTGGAT GCTTTCACGG AGTTCTTGGT GTCCATTGTT    120
GATATCATCA TATTTTTGGC CATTTTGTTT GGCTTCACCA TTGCCGGCTG GCTGGTGGTC    180
TTTTGCATCA GATTGGTTTG CTCCGCGATA CTCCGTGCGC GCCCTGCCAT TCACCCTGAG    240
CAATTACAGA AGATCCTATG AGGCCTTTCT TTCTCAGTGC CAGGTGGACA TTCCCGCCTG    300
GGGAACAAGA CATCCTTTAG GGATGCTTTG GCACCACAAG GTGTCAACCC TGATTGATGA    360
AATGGTGTCG CGTCGAATGT ACCGCATCAT GGAAAAAGCA GGACAGGCTG CCTGGAAACA    420
GGTGGTGAGT GAGGCTACGC TGTCTCGCAT TAGTGGTTTG GATGTGGTGG CCCATTTTCA    480
GCACCTTGCC GCCATTGAAG CCGAGACTTG TAAATATTTG GCCTCTCGGT TGCCCATGCT    540
ACACAACCTG CGTATTACAG GGTCAAATGT AACCATAGTG CATAATAGTA CTTTGAATCA    600
GGTGTTTGCT ATTTTCCCAA CCCCCGGTTC TCGGCCAAAG CTCCATGATT TTCAGCAATG    660
GCTAATAGCT GTACATTCCT CGATATCCTC CTCTGTTGCA GCTTCTTGTA CTCTTTTTGT    720
TGTGTTGTGG TTACGGATGC CAATGCTACG TTCTGTTTTT GGTTTCCGCT GGTTAGGGGC    780
AATTTTTCCT TCGAGCTCAT GGTGAATTAC ACGGTGTGCC CACCTTGCCT CACCCGGCAA    840
GCAGCCGCAC AGATCTACGA ACCCAACAGG TCTCTTTGGT GCAGGATCGG GAATGATCGA    900
TGTGGTGAGG ACGATCACGA CGAACTAGGA TTTACAGTAC CGCCTGGCCT CTCCAAAGAA    960
GTCCATTTGA CCAGTGTTTA CGCCTGGTTG GCGTTTCTGT CCTTCAGTAA CACGGCCCAG   1020
TTTCATCCCG AGATATTCGG AATAGGGAAT GTGAGTAAGG TCTATGTTGA CATCAATCAT   1080
```

-continued

CAACTCATTT GTGCTGTTCA TGACGGGCAG AACACCACCT TGCCTCGCCA TGACAACATT 1140

TCTGCCGTGT TTCAGACCTA TTACCAACAC CAAGTCGATG GTGGCAACTG GTTTCACCTA 1200

GAATGGCTGC GTCCCTTCTT TTCCTCTTGG TTGGTTTTGA ATGTCTCCTG GTTTCTCAGG 1260

CGTTCGCCTG CAAGCCATGT TTCAGTTCGA GTCTTTCAGA CATCAAGACC AACACCACCG 1320

CGGCAGCAAA TTTCGCTGTC CTCCAGGACA TCGGCTGCCT TAGGCATGGC AACTCGACCA 1380

CTGAGGCGTT TCGCAAAATC CCTCAGTGCC GCACGGCGAT AGGGACACCC GTGTATATCA 1440

CTATCACAGC CAATGTAACA GATGAGAACT ATTTGCATTC TTCTGATCTT CTCATGCTTT 1500

CCTCTTGCCT TTTCTACGCT TCTGAGATGA GTGAAAAGGG GTTTAAGGTG GTGTTTGGCA 1560

ATGTGTCAGG CACCGTGGCT GTGTGCATCA ATTTTACCAG CTATGTCCAA CACGTCAAGG 1620

AGTTTACCCA ACGCTCCTTA GTGGTCGACC ATGTGCGGCT GCTCCATTTC ATGACACCTG 1680

AAACTATGAG GTGGGCAACT GTTTTAGCCT GTCTTTTCGC CATTCTGTTG GCAATTTGAA 1740

TGTTTAAGTA TGTTGGGGAA ATGCTTGACC GCGGGCTGTT GCTCGCGATC GCTTTTTTTG 1800

TGGTGTATCG TGCCGTTCTG TCTTGCTGCG CTCGTCAGCG CCAACAACAG CAGCTCCCAT 1860

TTACAGTTGA TTTATAACCT GACGCTATGT GAGCTGAATG GCACAGACTG GCTGGCTAAT 1920

AAATTTGATT GGGCAGTGGA GAGTTTTGTC ATCTTTCCCG TGTTGACTCA CATTGTTTCC 1980

TATGGTGCAC TCACCACCAG CCATTTCCTT GACACAGTCG GTCTGGTTAC TGTGTCTACC 2040

GCCGGGTTTC ATCACGGGCG GTATGTTCTG AGTAGCATCT ACGCGGTCTG TGCCCTGGCT 2100

GCGTTTATTT GCTTCGTCAT TAGGTTTGCG AAGAACTGCA TGTCCTGGCG CTACTCTTGT 2160

ACCAGATATA CCAACTTCCT TCTGGACACT AAGGGCAGCC TCTATCGTTG GCGGTCACCT 2220

GTCATCATAG AGAAAGGGGG TAAGGTTGAG GTCGAAGGTC ATCTGATCGA CCTAAAAAAA 2280

GTTGTGCTTG ATGGTTCCGC GGCAACCCCT TTAACCAGAG TTTCAGCGGA ACAATGGGGT 2340

CGTCCCTAG 2349

(2) INFORMATION FOR SEQ ID NO:3:

(i) SEQUENCE CHARACTERISTICS:
(A) LENGTH: 2352 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory virus
(B) STRAIN: Iowa
(C) INDIVIDUAL ISOLATE: ISU55

(xi) SEQUENCE DESCRIPTION: SEQ ID NO:3:

CCTATCATTG AACCAACTTT AGGCCTGAAT TGAAATGAAA TGGGGTCTAT GCAAAGCCTT 60

TTTGACAAAA TTGGCCAACT TTTCGTGGAT GCTTTCACGG AGTTCTTGGT GTCCATTGTT 120

GATATCATTA TATTTTTGGC CATTTTGTTT GGCTTCACCA TCGCCGGTTG GCTGGTGGTC 180

TTTTGCATCA GATTGGTTTG CTCCGCGATA CTCCGTGCGC GCCCTGCCAT TCACTCTGAG 240

CAATTACAGA AGATCCTATG AGGCCTTTCT TTCTCAGTGC CAGGTGGACA TTCCCACCTG 300

GGGAATTAAA CATCCTTTGG GGATGCTTTG GCACCATAAG GTGTCAACCC TGATTGATGA 360

AATGGTGTCG CGTCGAATGT ACCGCATCAT GGAAAAAGCA GGACAGGCTG CCTGGAAACA 420

GGTGGTGAGC GAGGCTACGC TGTCTCGCAT TAGTAGTTTG GATGTGGTGG CTCACTTTCA 480

```
GCATCTTGCC GCCATTGAAG CCGAGACCTG TAAATATTTG GCCTCTCGGC TGCCCATGCT      540

ACACAACCTG CGCATGACAG GGTCAAATGT AACCATAGTG TATAATAGTA CTTTGAATCA      600

GGTGCTTGCT ATTTTCCCAA CCCCTGGTTC CCGGCCAAAG CTTCATGATT TTCAGCAATG      660

GCTAATAGCT GTACATTCCT CTATATTTTC CTCTGTTGCA GCTTCTTGTA CTCTTTTTGT      720

TGTGCTGTGG TTGCGGGTTC AATGCTACG TATTGCTTTT GGTTTCCGCT GGTTAGGGGC      780

AATTTTTCTT TCGAACTCAC AGTGAACTAC ACGGTGTGTC CACCTTGCCT CACCCGGCAA      840

GCAGCCACAG AGGCCTACGA ACCTGGCAGG TCTCTTTGGT GCAGGATAGG GTATGATCGC      900

TGTGGGAGG ACGATCATGA TGAACTAGGG TTTGTGGTGC CGTCTGGCCT CTCCAGCGAA      960

GGCCACTTGA CCAGTGTTTA CGCCTGGTTG GCGTTCCTGT CTTTCAGTTA CACAGCCCAG     1020

TTCCATCCTG AGATATTCGG GATAGGGAAT GTGAGTCAAG TTTATGTTGA CATCAGGCAT     1080

CAATTCATTT GCGCCGTTCA CGACGGGCAG AACGCCACTT TGCCTCGCCA TGACAATATT     1140

TCAGCCGTGT TCCAGACTTA TTACCAACAT CAAGTCGACG GCGGCAATTG GTTTCACCTA     1200

GAATGGCTGC GTCCCTTCTT TTCCTCTTGG TTGGTTTTAA ATGTCTCTTG GTTTCTCAGG     1260

CGTTCGCCTG CAAGCCATGT TTCAGTTCGA GTCTTGCAGA CATTAAGACC AACACCACCG     1320

CAGCGGCAGG CTTTGCTGTC CTCCAAGACA TCAGTTGCCT TAGGTATCGC AACTCGGCCT     1380

CTGAGGCGTT TCGCAAAATC CCTCAGTGTC GTACGGCGAT AGGGACACCC ATGTATATTA     1440

CTGTCACAGC CAATGTAACC GATGAGAATT ATTTGCATTC CTCTGACCTT CTCATGCTTT     1500

CTTCTTGCCT TTTCTACGCT TCTGAGATGA GTGAAAAGGG ATTTAAAGTG GTATTTGGCA     1560

ATGTGTCAGG CATCGTGGCT GTGTGCGTCA ACTTTACCAG CTACGTCCAA CATGTCAAGG     1620

AATTTACCCA ACGCTCCTTG GTAGTCGACC ATGTGCGGCT GCTCCATTTC ATGACACCTG     1680

AGACCATGAG GTGGGCAACT GTTTTAGCCT GTCTTTTTGC CATTCTGTTG GCCATTTGAA     1740

TGTTTAAGTA TGTTGGGGAA ATGCTTGACC GCGGGCTATT GCTCGTCATT GCTTTTTTTG     1800

TGGTGTATCG TGCCGTCTTG GTTTGTTGCG CTCGCCAGCG CCAACAGCAG CAACAGCTCT     1860

CATTTACAGT TGATTTATAA CTTGACGCTA TGTGAGCTGA ATGGCACAGA TTGGTTAGCT     1920

GGTGAATTTG ACTGGGCAGT GGAGTGTTTT GTCATTTTTC CTGTGTTGAC TCACATTGTC     1980

TCCTATGGTG CCCTCACCAC CAGCCATTTC CTTGACACAG TCGGTCTGGT CACTGTGTCT     2040

ACCGCCGGCT TTTCCCACGG GCGGTATGTT CTGAGTAGCA TCTACGCGGT CTGTGCCCTG     2100

GCTGCGTTGA TTTGCTTCGT CATTAGGTTT ACGAAGAATT GCATGTCCTG CGCTACTCA     2160

TGTACCAGAT ATACCAACTT TCTTCTGGAC ACTAAGGGCA GACTCTATCG TTGGCGGTCG     2220

CCTGTCATCA TAGAGAAAAG GGGTAAAGTT GAGGTCGAAG GTCATCTGAT CGACCTCAAG     2280

AGAGTTGTGC TTGATGGTTC CGCGGCAACC CCTATAACCA AAGTTTCAGC GGAGCAATGG     2340

GGTCGTCCTT AG                                                         2352

(2) INFORMATION FOR SEQ ID NO:4:

(i) SEQUENCE CHARACTERISTICS:
        (A) LENGTH: 2351 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Porcine reproductive and respiratory virus
        (B) STRAIN: Iowa
        (C) INDIVIDUAL ISOLATE: ISU22
```

(xi) SEQUENCE DESCRIPTION: SEQ ID NO:4:

```
CCTGTCATTG AACCAACTTT AGGCCTGAAT TGAAATGAAA TGGGGGCCAT GCAAAGCCTT      60

TTTGACAAAA TTGGCCAACT TTTTGTGGAT GCTTTCACGG AGTTCTTGGT GTCCATTGTT     120

GATATCATTA TATTTTTGGC CATTTTGTTT GGCTTCACCA TCGCCGGTTG GCTGGTGGTC     180

TTTTGCATCA GATTGGTTTG CTCCGCGATA CTCCGTGCGC GCCCTGCCAT TCACTCTGAG     240

CAATTACAGA AGATCTTATG AGGCCTTTCT TTCCCAGTGC CAAGTGGACA TTCCCACCTG     300

GGGAACTAAA CATCCTTTGG GGATGTTGTG GCACCATAAG GTGTCAACCC TGATTGATGA     360

AATGGTGTCG CGTCGAATGT ACCGCATCAT GGAAAAAGCA GGGCAGGCTG CCTGGAAACA     420

GGTGGTGAGC GAGGCTACGC TGTCTCGCAT TAGTAGTTTG GATGTGGTGG CTCATTTTCA     480

GCATCTTGCT GCCATTGAAG CCGAGACCTG TAAATATTTG GCCTCCCGGC TGCCCATGCT     540

ACACAACCTG CGCATGACAG GGTCAAATGT AACCATAGTG TATAATAGTA CTTTGAATCA     600

GGTGTTTGCT ATTTTCCCAA CCCCTGGTTC CCGGCCAAAG CTTCATGATT TCAGCAATG     660

GTTAATAGCT GTACATTCCT CCATATTTTC CTCTGTTGCA GCTTCCTGTA CTCTTTTTGT     720

TGTGCTGTGG TTGCGGGTTC AATACTACG TTCTGTTTTT GGTTTCCGCT GGTTAGGGGC     780

AATTTTTCTT TCGAGCTCAC GGTGAATTAC ACGGTGTGTC CACCTTGCCT CACCCGGCAA     840

GCAGCCGCAG AGATCTACGA ACCCGGTAGG TCTCTTTGGT GCAGGATAGG GTATGACCGA     900

TGTGGGAGG ACGATCATGA CGAGCTAGGG TTTATGGTAC CACCTGGCTT CTCCAGCGAA     960

GGCCACTTGA CTAGTGTTTA CGCCTGGTTG GCGTTTTTGT CCTTCAGCTA CACGGCCCAG    1020

TTCCATCCCG AGATATTCGG GATAGGGAAC GTGAGTCGAG TTTATGTTGA CATCAAACAT    1080

CAACTCATCT GCGCCGAACA TGACGGGCAA AACACCACCT TGCCTCGTCA TGACAACATT    1140

TCAGCCGTGT TTCAGACCTA TTACCAACAT CAAGTCGACG GTGGCAATTG GTTTCACCTA    1200

GAATGGCTTC GTCCCTTCTT TTCCTCATGG TTGGTTTTAA ATGTCTCTTG GTTTCTCAGG    1260

CGTTCGCCTG CAAACCATGT TTCAGTTCGA GTCTTGCAGA TATTAAGACC AACACCACCG    1320

CAGCGGCAAG CTTTGCTGTC CTCCAAGACA TCGGTTGCCT TAGGCATCGC GACTCGGCCT    1380

CTGAGGCGAT TCGCAAAATC CCTCAGTGCC GTACGGCGAT AGGGACACCC GTGTATATTA    1440

CCATCACAGC CAATGTGAAC GATGAGAATT ATTTACATTC TTCTGATCTC CTCATGCTTT    1500

CTTCTTGCCT TTTCTATGCT TCTGAGATGA GTGAAAAGGG GTTTAAGGTG GTATTTGGCA    1560

ATGTGTCAGG CATCGTGGCT GTGTGTGTCA ATTTTACCAG CTATGTCCAA CATGTCAGGG    1620

AGTTTACCCA ACGCTCCTTG GTGGTCGACC ATGTGCGGTT GCTCCATTTC ATGACACCTG    1680

AGACCATGAG GTGGGCAACT GTTTTAGCCT GTCTTTTTGC CATTCTGTTG GCAATTTGAA    1740

TGTTTAAGCA TGTTGGGGAA ATGCTTGACC GCGGGCTGTT GCTCGCGATT GCTTTCTTTG    1800

TGGTTTATCG TGCCGTTCTG TTTTGCTGTG CTCGCCAGCG CCAGCAACAG CAGCAGCTCC    1860

CATCTACAGT TGATTTATAA CTTGACGCTA TGTGAGCTGA ATGGCACAGA TTGGTTAGCT    1920

AATAAATTTG ATTGGGCAGT GGAGAGTTTT GTCATCTTTC CCGTTTTGAC TCACATTGTC    1980

TCCTATGGTG CCCTCACTAC CAGCCATTTC CTTGACACAG TCGCTTTAGT CACTGTGTCT    2040

ACCGCCGGGT TTGTTCACGG GCGGTATGTC CTGAGTAGCA TCTACGCGGT CTGTGCCCTG    2100

GCTGCGTTGA CTTGCTTCAT CATCAGGTTT GCAAAGAATT GCATGTCCTG GCGCTACTCG    2160

TGTACCAGAT ATACCAACTT TCTCCTGGAC ACTAAGGGCA GACTCTATCG TTGGCGGTCG    2220

CCTGTCATCA TAGAGAAAAG GGGCAAAGTT GAGGTCGAAG GTCACTGATC GACCTCAAAA    2280
```

| GAGTTGTGCT TGATGGTTCC GTGGCAACCC CTATAACCAG AGATTCAGCG GAACAATGGG | 2340 |
| GTCGTCCTTA G | 2351 |

(2) INFORMATION FOR SEQ ID NO:5:

(i) SEQUENCE CHARACTERISTICS:
        (A) LENGTH: 2352 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Porcine reproductive and respiratory virus
        (C) INDIVIDUAL ISOLATE: VR2332

(xi) SEQUENCE DESCRIPTION: SEQ ID NO:5:

| CCTGTCATTG AACCAACTTT AGGCCTGAAT TGAAATGAAA TGGGGTCCAT GCAAAGCCTT | 60 |
| TTTGACAAAA TTGGCCAACT TTTTGTGGAT GCTTTCACGG AGTTCTTGGT GTCCATTGTT | 120 |
| GATATCATTA TATTCTTGGC CATTTTGTTT GGCTTCACCA TCGCCGGTTG GCTGGTGGTC | 180 |
| TTTTGCATCA GATTGGTTTG CTCCGCGATA CTCCGTACGC GCCCTGCCAT TCACTCTGAG | 240 |
| CAATTACAGA AGATCTTATG AGGCCTTTCT TTCCCAGTGC CAAGTGGACA TTCCCACCTG | 300 |
| GGGAACTAAA CATCCTTTGG GGATGTTTTG GCACCATAAG GTGTCAACCC TGATTGATGA | 360 |
| GATGGTGTCG CGTCGAATGT ACCGCATCAT GGAAAAAGCA GGACAGGCTG CCTGGAAACA | 420 |
| GGTGGTGAGC GAGGCTACGC TGTCTCGCAT TAGTAGTTTG GATGTGGTGG CTCATTTTCA | 480 |
| GCATCTTGCC GCCATCGAAG CCGAGACCTG TAAATATTTG GCCTCCCGGC TGCCCATGCT | 540 |
| ACACAACCTG CGCATGACAG GGTCAAATGT AACCATAGTG TATAATAGTA CTTTGAATCG | 600 |
| GGTGTTTGCT ATTTTCCCAA CCCCTGGTTC CCGGCCAAAG CTTCATGACT TTCAGCAATG | 660 |
| GCTAATAGCT GTGCATTCCT CCATATTTTC CTCTGTTGCA GCTTCTTGTA CTCTCTTTGT | 720 |
| TGTGCTGTGG TTGCGGGTTC CAATACTACG TACTGTTTTT GGTTTCCGCT GGTTAGGGGC | 780 |
| AATTTTTCTT TCGAACTCAT AGTGAATTAC ACGGTGTGCC CACCTTGCCT CACCCGGCAA | 840 |
| GCAGCCGCAG AGGCCTACGA ACCCGGTAGG TCTCTTTGGT GCAGGATAGG GTACGATCGA | 900 |
| TGTGGAGAGG ACGACCATGA CGAGCTAGGG TTTATGATAC CGTCTGGCCT CTCCAGCGAA | 960 |
| GGCCACTTGA CCAGTGTTTA CGCCTGGTTG GCGTTCTTGT CCTTCAGCTA CACGGCCCAG | 1020 |
| TTCCACCCCG AGATATTCGG GATAGGGAAT GTGAGTCGAG TTTATGTTGA CATCAAACAT | 1080 |
| CAACTCATCT GCGCCGAACA TGACGGGCAG AACACCACCT TGCCTCGTCA TGACAACATT | 1140 |
| TCGGCCGTGT TTCAGACCTA TTACCAACAT CAAGTCGACG GCGGCAATTG GTTTCACCTA | 1200 |
| GAATGGCTGC GTCCCTTCTT TTCCTCATGG TTGGTTTTAA ATGTCTCTTG GTTTCTCAGG | 1260 |
| CGTTCGCCTG CAAACCATGT TTCAGTTCGA GTCTTGCAGA CATTAAGACC AACACCACCG | 1320 |
| CAGCGGCAAG CTTTGCTGTC CTCCAAGACA TCAGTTGCCT TAGGCATCGC AACTCGGCCT | 1380 |
| CTGAGGCGAT TCGCAAAATC CCTCAGTGCC GTACGGCGAT AGGGACACCT ATGTATATTA | 1440 |
| CCATCACAGC CAATGTGACA GATGAAAATT ATTTACATTC TTCTGATCTC CTCATGCTCT | 1500 |
| CTTCTTGCCT TTTCTATGCT TCTGAGATGA GTGAAAAGGG ATTTGAGGTG GTTTTTGGCA | 1560 |
| ATGTGTCAGG CATCGTGGCT GTGTGTGTCA ATTTTACCAG CTACGTTCAA CATGTCAGGG | 1620 |
| AGTTTACCCA ACGCTCCTTG ATGGTCGACC ATGTGCGGCT GCTCCATTTC ATGACACCTG | 1680 |
| AGACCATGAG GTGGGCAACC GTTTTAGCCT GTCTTTTTGC TATTCTGTTG GCAATTTGAA | 1740 |

-continued

```
TGTTTAAGTA TGTTGGGGAA ATGCTTGACC GTGGGCTGTT GCTCGCGATT GCTTTCTTTG   1800

TGGTGTATCG TGCCGTTCTG TTTTACTGTG CTCGCCGACG CCCACAGCAA CAGCAGCTCT   1860

CATCTGCAAT TGATTTACAA CTTGACGCTA TGTGAGCTGA ATGGCACAGA TTGGCTAGCT   1920

GATAGATTTG ATTGGGCAGT GGAGAGCTTT GTCATCTTTC CTGTTTTGAC TCACATTGTC   1980

TCCTATGGCG CCCTCACCAC CAGCCATTTC CTTGACACAA TTGCTTTAGT CACTGTGTCT   2040

ACCGCCGGGT TTGTTCACGG GCGGTATGTC CTAAGTAGCA TCTACGCGGT CTGTGCCCTG   2100

GCTGCGTTGA CTTGCTTCGT CATTAGGTTT GTGAAGAATT GCATGTCCTG GCGCTACTCA   2160

TGTACTAGAT ATACCAACTT TCTTCTGGAT ACTAAGGGCA GACTCTATCG TTGGCGGTCG   2220

CCTGTCATCA TAGAGAAGAG GGGCAAAGTT GAGGTCGAAG GTCATCTGAT CGATCTCAAA   2280

AGAGTTGTGC TTGATGGTTC CGTGGCAACC CCTATAACCA GAGTTTCAGC GGAACAATGG   2340

GGTCGTCCTT AG                                                      2352
```

(2) INFORMATION FOR SEQ ID NO:6:

(i) SEQUENCE CHARACTERISTICS:
        (A) LENGTH: 2352 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Porcine reproductive and respiratory virus
        (B) STRAIN: Iowa
        (C) INDIVIDUAL ISOLATE: ISU1894

(xi) SEQUENCE DESCRIPTION: SEQ ID NO:6:

```
CCTGTCATTG AACCAACTTT AGGCCTGAAT TGAGATGAAA TGGGGTCTAT GCAAAGCCTT     60

TTTGACAAAA TTGGCCAACT TTTTGTGGAT GCTTTCACGG AGTTCTTGGT GTCCATTGTT    120

GATATCATTA TATTTTTGGC CATTTTGTTT GGCTTCACCA TCGCAGGTTG GCTGGTGGTC    180

TTTTGCATCA GATTGGTTTG CTCCGCGATA CTCCGTGCGC GCCCTGCCAT TCACTCTGAG    240

CAATTACAGA AGATCCTATG AGGCCTTTCT CTCTCAGTGC CAGGTGGACA TTCCCACCTG    300

GGGAACTAAA CATCCTTTGG GGATGCTTTG CACCATAAG GTGTCAACCC TGATTGATGA     360

AATGGTGTCG CGTCGAATGT ACCGCATCAT GGAAAAAGCA GGACAGGCTG CCTGGAAACA    420

GGTAGTGAGC GAGGCTACGC TGTCTCGCAT TAGTAGTTTG GATGTGGTGG CTCATTTTCA    480

GCATCTTGCC GCCATTGAAG CCGAGACCTG TAAATATCTG GCCTCTCGGC TGCCCATGCT    540

ACACCACCTG CGCATGACAG GGTCAAATGT AACCATAGTG TATAATAGTA CTTTGAATCA    600

GGTGTTTGCT GTTTTCCCAA CCCCTGGTTC CCGGCCAAAG CTTCATGATT CCAGCAATG    660

GCTAATAGCT GTACATTCCT CTATATTTTC CTCTGTTGCA GCTTCTTGTA CTCTTTTTGT    720

TGTGCTGTGG TTGCGGGTTC CAATGCTACG TACTGTTTTT GGTTTCCGCT GGTTAGGGGC    780

AATTTTTCTT TCGAACTCAC GGTGAATTAC ACGGTGTGCC CGCCTTGCCT CACCCGGCAA    840

GCAGCCGCAG AGGCCTACGA ACCCGGCAGG TCCCTTTGGT GCAGGATAGG GCATGATCGA    900

TGTGGGAGG ACGATCATGA TGAACTAGGG TTTTGTGGTGC CGTCTGGCCT CTCCAGCGAA    960

GGCCACTTGA CCAGTGCTTA CGCCTGGTTG GCGTCCCTGT CCTTCAGCTA TACGGCCCAG   1020

TTCCATCCCG AGATATTCGG GATAGGGAAT GTGAGTCGAG TCTATGTTGA CATCAAGCAC   1080

CAATTCATTT GCGCTGTTCA TGATGGGCAG AACACCACCT TGCCCCACCA TGACAACATT   1140

TCAGCCGTGC TTCAGACCTA TTACCAGCAT CAGGTCGACG GGGCAATTG GTTTCACCTA   1200
```

-continued

```
GAATGGGTGC GTCCCTTCTT TTCCTCTTGG TTGGTTTTAA ATGTCTCTTG GTTTCTCAGG   1260

CGTTCGCCTG CAAGCCATGT TTCAGTTCGA GTCTTTCAGA CATCAAGACC AACACCACCG   1320

CAGCGGCAGG CTTTGCTGTC CTCCAAGACA TCAGTTGCCT TAGGCATCGC AACTCGGCCT   1380

CTGAGGCGAT TCGCAAAGTC CCTCAGTGCC GCACGGCGAT AGGGACACCC GTGTATATCA   1440

CTGTCACAGC CAATGTTACC GATGAGAATT ATTTGCATTC CTCTGATCTT CTCATGCTTT   1500

CTTCTTGCCT TTTCTATGCT TCTGAGATGA GTGAAAAGGG ATTTAAGGTG GTATTTGGCA   1560

ATGTGTCAGG CATCGTGGCA GTGTGCGTCA ACTTCACCAG TTACGTCCAA CATGTCAAGG   1620

AATTTACCCA ACGTTCCTTG GTAGTTGACC ATGTGCGGCT GCTCCATTTC ATGACGCCCG   1680

AGACCATGAG GTGGGCAACT GTTTTAGCCT GTCTTTTTAC CATTCTGTTG GCAATTTGAA   1740

TGTTTAAGTA TGTTGGGGAA ATGCTTGACC GCGGGCTGTT GCTCGCAATT GCTTTTTTTA   1800

TGGTGTATCG TGCCGTCTTG TTTTGTTGCG CTCGTCAGCG CCAACGGGAA CAGCGGCTCA   1860

AATTTACAGC TGATTTACAA CTTGACGCTA TGTGAGCTGA ATGGCACAGA TTGGCTAGCT   1920

AATAAATTTG ACTGGGCAGT GGAGTGTTTT GTCATTTTTC CTGTGTTGAC TCACATTGTC   1980

TCTTATGGTG CCCTCACTAC TAGCCATTTC CTTGACACAG TCGGTCTGGT CACTGTGTCT   2040

ACCGCTGGGT TTGTTCACGG GCGGTATGTT CTGAGTAGCA TGTACGCGGT CTGTGCCCTG   2100

GCTGCGTTGA TTTGCTTCGT CATTAGGCTT GCGAAGAATT GCATGTCCTG GCGCTACTCA   2160

TGTACCAGAT ATACCAACTT TCTTCTGGAC ACTAAGGGCA GACTCTATCG TTGGCGGTCG   2220

CCTGTCATCA TAGAGAAAAG GGGCAAAGTT GAGGTCGAAG GTCACCTGAT CGACCTCAAA   2280

AGAGTTGTGC TTGATGGTTC CGCGGCTACC CCTGTAACCA GAGTTTCAGC GGAACAATGG   2340

AGTCGTCCTT AG                                                       2352
```

(2) INFORMATION FOR SEQ ID NO:7:

(i) SEQUENCE CHARACTERISTICS:
(A) LENGTH: 2352 base pairs
(B) TYPE: nucleic acid
(C) STRANDEDNESS: unknown
(D) TOPOLOGY: unknown (ii) MOLECULE TYPE: cDNA (vi) ORIGINAL SOURCE:
(A) ORGANISM: Porcine reproductive and respiratory virus
(B) STRAIN: Iowa
(C) INDIVIDUAL ISOLATE: ISU79

(xi) SEQUENCE DESCRIPTION: SEQ ID NO:7:

```
CCCGTCATTG AACCAACTTT AGGCCTGAAT TGAAATGAAA TGGGGTCCGT GCAAAGCCTT     60

TTTGACAAAA TTGGCCAACT TTTTGTGGAT GCTTTCACGG AGTTCCTGGT GTCCATTGTT    120

GATATCATCA TATTTTTGGC CATTTTGTTT GGCTTCACCA TCGCCGGTTG GCTGGTGGTC    180

TTTTGCATCA GATTGGTTTG CTCCGCGATA CTCCGTACGC GCCCTGCCAT TCACTCTGAG    240

CAATTACAGA AGATCTTATG AGGCCTTTTT ATCCCAGTGC CAAGTGGACA TTCCCACCTG    300

GGGAACTAAA CATCCTTTGG GGATGTTTTG GCACCATAAG GTGTCAACCC TGATTGATGA    360

AATGGTGTCG CGTCGCATGT ACCGCATCAT GGAAAAAGCA GGGCAGGCTG CCTGGAAACA    420

GGTGGTGAGC GAGGCTACGC TGTCCCGCAT TAGTAGTTTG GATGTGGTGG CTCATTTTCA    480

GCATCTTGCC GCCATTGAAG CCGAGACTTG TAAATATTTG GCCTCCCGGC TGCCCATGCT    540

ACATAACCTG CGCATAACAG GGTCAAATGT AACCATAGTG TATAATAGTA CTTCGGAGCA    600
```

-continued

```
GGTGTTTGCT ATTTTCCCAA CCCCTGGTTC CCGGCCAAAG CTTCATGATT TTCAGCAATG    660
GTTAATAGCT GTACATTCCT CCATATTTTC CTCTGTTGCA GCTTCTTGTA CTCTTTTTGT    720
TGTGCTGTGG CTGCGGGTTC CAATGCTACG TACTGTTTTT GGTTTCCGCT GGTTAGGGGG    780
AATTTTTCCT TCGAACTCAT GGTGAATTAC ACGGTGTGTC CACCTTGCCT CACCCGGCAA    840
GCAGCCGCAG AGGTCTACGA ACCCGGTAGG TCTCTTTGGT GCAGGATAGG GTATGACCGA    900
TGTGGGAGG ACGATCATGA CGAGCTAGGG TTTATGATAC CGCCTGGCCT CTCCAGCGAA     960
GGCCACTTGA CTAGTGTTTA CGCCTGGTTG GCGTTTTTGT CCTTCAGCTA CACGGCCCAG   1020
TTCCATCCCG AGATATTCGG GATAGGGAAT GTGAGTCGAG TTTATGTTGA CATCAAACAT   1080
CAACTCATTT GCGCCGAACA TGACGGACAG AACGCCACCT TGCCTCGTCA TGACAATATT   1140
TCAGCCGTGT TCAGACCTA TTACCAACAT CAAGTCGATG GCGGCAATTG GTTTCACCTA    1200
GAATGGCTTC GTCCCTTCTT TTCCTCATGG TTGGTTTTAA ATGTCTCTTG GTATCTCAGG   1260
CGTTCGCCTG CAAACCATGC TTCAGTTCGA GTCTTGCAGA TATTAAGACC AACACTACCG   1320
CAGCGGCAAG CTTTGCTGTC CTCCAAGACA TCAGTTGCCT TAGGCATCGC AACTCGGCCT   1380
CTGAGGCGAT TCGCAAAATC CCTCAGTGCC GTACGGCGAT AGGGACACCC GTGTATATTA   1440
CCATCACAGC CAATGTGACA GATGAGAATT ATTTACATTC TTCTGATCTC CTCATGCTTT   1500
CTTCTTGCCT TTTCTACGCT TCTGAGATGA GTGAAAAAGG ATTCAAGGTG GTATTTGGCA   1560
ATGTGTCAGG CATCGTGGCT GTGTGTGTCA ATTTTACCAG CTACGTCCAA CATGTCAGGG   1620
AGTTTACCCA ACGCTCCCTG GTGGTCGACC ATGTGCGGTT GCTCCATTTC ATGACACCTG   1680
AAACCATGAG GTGGGCAACT GTTTTAGCCT GTCTTTTTGC CATTCTGCTG GCAATTTGAA   1740
TGTTTAAGTA TGTTGGGGAA ATGCTTGACC GCGGGCTGTT GCTCGCGATT GCTTTCTTTG   1800
TGGTGTATCG TGCCGTTCTG TTTTGCTGTG CTCGCCAACG CCAGCGCCAA CAGCAGCTCC   1860
CATCTACAGC TGATTTACAA CTTGACGCTA TGTGAGCTGA ATGGCACAGA TTGGCTAGCT   1920
GATAAATTTG ATTGGGCAGT GGAGAGTTTT GTCATCTTTC CCGTTTTGAC TCACATTGTC   1980
TCCTATGGTG CCCTCACTAC TAGCCATCTC CTTGACACAG TCGCCTTAGT CACTGTGTCT   2040
ACCGCCGGGT TTGTTCACGG GCGGTATGTC CTAAGTAGCA TCTACGCGGT CTGTGCCCTG   2100
GCTGCGTTAG CTTGCTTCGT CATTAGGTTT GCAAAGAATT GCATGTCCTG GCGCTATTCG   2160
TGTACCAGAT ATACCAACTT TCTTCTGGAC ACTAAGGGCA GACTCTATCG TTGGCATTCG   2220
CCTGTCATCA TAGAGAAAAG GGGCAAAGTT GAGGTCGAAG GTCATCTGAT CGACCTCAAA   2280
AGAGTTGTGC TTGACGGTTC CGTGGCAACC CCTATAACCA GAGTTTCAGC GGAACAATGG   2340
GGTCGTCCTT AG                                                      2352
```

(2) INFORMATION FOR SEQ ID NO:8:

(i) SEQUENCE CHARACTERISTICS:
        (A) LENGTH: 256 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: VR2385

(xi) SEQUENCE DESCRIPTION: SEQ ID NO:8:

Met Lys Trp Gly Leu Cys Lys Ala Phe Leu Thr Lys Leu Ala Asn Phe

```
 1               5                    10                   15
Leu Trp Met Leu Ser Arg Ser Ser Trp Cys Pro Leu Leu Ile Ser Leu
            20                  25                  30

Tyr Phe Trp Pro Phe Cys Leu Ala Ser Pro Ser Gln Val Gly Trp Trp
            35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95

Met Leu Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
            115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Met Leu Arg Met Thr Gly
                165                 170                 175

Ser Asn Val Thr Ile Val Tyr Asn Ser Thr Leu Asn Gln Val Phe Ala
            180                 185                 190

Val Phe Pro Thr Pro Gly Ser Arg Pro Lys Leu His Asp Phe Gln Gln
            195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Met Leu Arg Thr
225                 230                 235                 240

Val Phe Gly Phe Arg Trp Leu Gly Ala Ile Phe Leu Ser Asn Ser Arg
                245                 250                 255

(2) INFORMATION FOR SEQ ID NO:9:

(i) SEQUENCE CHARACTERISTICS:
        (A) LENGTH: 256 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (

```
Gln Cys Gln Val Asp Ile Pro Thr Trp Gly Thr Lys His Pro Leu Gly
                85                  90                  95

Met Leu Trp His His Lys Val Ser Thr Leu Ile Asp Glu Met Val Ser
               100                 105                 110

Arg Arg Met Tyr Arg Ile Met Glu Lys Ala Gly Gln Ala Ala Trp Lys
               115                 120                 125

Gln Val Val Ser Glu Ala Thr Leu Ser Arg Ile Ser Ser Leu Asp Val
           130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
               165                 170                 175

Ser Asn Val Thr Ile Val Tyr Asn Ser Thr Leu Asn Gln Val Phe Ala
               180                 185                 190

Ile Phe Pro Thr Pro Gly Ser Arg Pro Lys Leu His Asp Phe Gln Gln
               195                 200                 205

Trp Leu Ile Ala Val His Ser Ser Ile Phe Ser Ser Val Ala Ala Ser
           210                 215                 220

Cys Thr Leu Phe Val Val Leu Trp Leu Arg Val Pro Ile Leu Arg Ser
225                 230                 235                 240

Val Phe Gly Phe Arg Trp Leu Gly Ala Ile Phe Leu Ser Ser Ser Arg
               245                 250                 255

(2) INFORMATION FOR SEQ ID NO:10:

(i) SEQUENCE CHARACTERISTICS:
        (A) LENGTH: 255 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU79

(xi) SEQUENCE DESCRIPTION: SEQ ID NO:10:

Met Lys Trp Gly Pro Cys Lys Ala Phe Leu Thr Lys Leu Ala Asn Phe
1               5                   10                  15

Leu Trp Met Leu Ser Arg Ser Ser Trp Cys Pro Leu Leu Ile Ser Leu
                20                  25                  30

Ser Phe Trp Pro Phe Cys Leu Ala Ser Pro Ser Pro Val Gly Trp Trp
            35                  40                  45

Ser Phe Ala Ser Asp Trp Phe Ala Pro Arg Tyr Ser Val Arg Ala Leu
        50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95

Met Phe Trp His His Lys Val Ser Thr Leu Ile Asp Glu Met Val Ser
               100                 105                 110

Arg Arg Met Tyr Arg Ile Met Glu Lys Ala Gly Gln Ala Ala Trp Lys
               115                 120                 125

Gln Val Val Ser Glu Ala Thr Leu Ser Arg Ile Ser Ser Leu Asp Val
           130                 135                 140
```

```
Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Met Thr Gly
                165                 170                 175

Ser Asn Val Thr Ile Val Tyr Asn Ser Thr Leu Asn Arg Val Phe Ala
                180                 185                 190

Ile Phe Pro Thr Pro Gly Ser Arg Pro Lys Leu His Asp Phe Gln Gln
                195                 200                 205

Trp Leu Ile Ala Val His Ser Ser Ile Phe Ser Ser Val Ala Ala Ser
            210                 215                 220

Cys Thr Leu Phe Val Val Leu Trp Leu Arg Val Pro Ile Leu Arg Thr
225                 230                 235                 240

Val Phe Gly Phe Arg Trp Leu Gly Ala Ile Phe Leu Ser Asn Ser
                245                 250                 255
```

(2) INFORMATION FOR SEQ ID NO:11:

(i) SEQUENCE CHARACTERISTICS:
        (A) LENGTH: 256 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU55

(xi) SEQUENCE DESCRIPTION: SEQ ID NO:11:

```
Met Lys Trp Gly Leu Cys Lys Ala Phe Leu Thr Lys Leu Ala Asn Phe
1               5                   10                  15

Ser Trp Met Leu Ser Arg Ser Ser Trp Cys Pro Leu Leu Ile Ser Leu
                20                  25                  30

Tyr Phe Trp Pro Phe Cys Leu Ala Ser Pro Ser Pro Val Gly Trp Trp
                35                  40                  45

Ser Phe Ala

```
            210                 215                 220
Cys Thr Leu Phe Val Val Leu Trp Leu Arg Val Pro Met Leu Arg Ile
225                 230                 235                 240

Ala Phe Gly Phe Arg Trp Leu Gly Ala Ile Phe Leu Ser Asn Ser Gln
                245                 250                 255
```

(2) INFORMATION FOR SEQ ID NO:12:

(i) SEQUENCE CHARACTERISTICS:
        (A) LENGTH: 256 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU1894

(xi) SEQUENCE DESCRIPTION: SEQ ID NO:12:

```
Met Lys Trp Gly Pro Cys Lys Ala Phe Leu Thr Lys Leu Ala Asn Phe
1               5                   10                  15

Leu Trp Met Leu Ser Arg Ser Ser Trp Cys Pro Leu Leu Ile Ser Ser
            20                  25                  30

Tyr Phe Trp Pro Phe Cys Leu Ala Ser Pro Ser Pro Val Gly Trp Trp
        35                  40                  45

Ser Phe Ala Ser Asp Trp Phe Ala Pro Arg Tyr Ser Val Arg Ala Leu
    50                  55                  60

Pro Phe Thr Leu Ser Asn Tyr Arg Arg Ser Tyr Glu Ala Phe Leu Ser
65                  70                  75                  80

Gln Cys Gln Val Asp Ile Pro Thr Trp Gly Thr Lys His Pro Leu Gly
                85                  90                  95

Met Phe Trp His His Lys Val Ser Thr Leu Ile Asp Glu Met Val Ser
            100                 105                 110

Arg Arg Met Tyr Arg Ile Met Glu Lys Ala Gly Gln Ala Ala Trp Lys
        115                 120                 125

Gln Val Val Ser Glu Ala Thr Leu Ser Arg Ile Ser Ser Leu Asp Val
    130                 135                 140

Val Ala His Phe Gln His Leu Ala Ala Ile Glu Ala Glu Thr Cys Lys
145                 150                 155                 160

Tyr Leu Ala Ser Arg Leu Pro Met Leu His Asn Leu Arg Ile Thr Gly
                165                 170                 175

Ser Asn Val Thr Ile Val Tyr Asn Ser Thr Ser Glu Gln Val Phe Ala
            180                 185                 190

Ile Phe Pro Thr Pro Gly Ser Arg Pro Lys Leu His Asp Phe Gln Gln
        195                 200                 205

Trp Leu Ile Ala Val His Ser Ser Ile Phe Ser Ser Val Ala Ala Ser
    210                 215                 220

Cys Thr Leu Phe Val Val Leu Trp Leu Arg Val Pro Met Leu Arg Thr
225                 230                 235                 240

Val Phe Gly Phe Arg Trp Leu Gly Gly Ile Phe Pro Ser Asn Ser Trp
                245                 250                 255
```

(2) INFORMATION FOR SEQ ID NO:13:

(i) SEQUENCE CHARACTERISTICS:
(A) LENGTH: 256 amino acids

```
              (B) TYPE: amino acid
              (C) STRANDEDNESS:
              (D) TOPOLOGY: linear (ii) MOLECULE TYPE: protein (vi) ORIGINAL SOURCE:
              (A) ORGANISM: Porcine reproductive and respiratory virus
              (B) STRAIN: Iowa
              (C) INDIVIDUAL ISOLATE: ISU3927

(xi) SEQUENCE DESCRIPTION: SEQ ID NO:13:

Met Gln Trp Gly Pro Cys Lys Ala Phe Leu Thr Arg Ser Val Asn Phe
1               5                   10                  15

Leu Trp Met Leu Ser Arg Ser Ser Trp Cys Pro Leu Leu Ile Ser Ser
            20                  25                  30

Tyr Phe Trp Pro Phe Cys Leu Ala Ser Pro Leu Pro Ala Gly Trp Trp
        35                  40                  45

Ser Phe Ala Ser Asp Trp Phe Ala Pro Arg Tyr Ser Val Arg Ala Leu
    50                  55                  60

Pro Phe Thr Le

```
1               5                   10                  15
Leu Trp Met Leu Ser Arg Ser Ser Trp Cys Pro Leu Leu Ile Ser Leu
                20                  25                  30
Tyr Phe Trp Pro Phe Cys Leu Ala Ser Pro Ser Pro Val Gly Trp Trp
                35                  40                  45
Ser Phe Ala Ser Asp Trp Phe Ala Pro Arg Tyr Ser Val Arg Ala Leu
    50                  55                  60
Pro Phe Thr Leu Ser Asn Tyr Arg Arg Ser Tyr Glu Ala Phe Leu Ser
65                  70                  75                  80
Gln Cys Gln Val Asp Ile Pro Thr Trp Thr Lys His Pro Leu Gly
                85                  90                  95
Met Leu Trp His His Lys Val Ser Thr Leu Ile Asp Glu Met Val Ser
                100                 105                 110
Arg Arg Met Tyr Arg Ile Met Glu Lys Ala Gly Gln Ala Ala Trp Lys
                115                 120                 125
Gln Val Val Ser Glu Ala Thr Leu Ser Arg Ile Ser Ser Leu Asp Val
    130                 135                 140
Val Ala His Phe Gln His Leu Ala Ala Ile Glu Ala Glu Thr Cys Lys
145                 150                 155                 160
Tyr Leu Ala Ser Arg Leu Pro Met Leu His Asn Leu Arg Met Thr Gly
                165                 170                 175
Ser Asn Val Thr Ile Val Tyr Asn Ser Thr Leu Asn Gln Val Phe Ala
                180                 185                 190
Ile Phe Pro Thr Pro Gly Ser Arg Pro Lys Leu His Asp Phe Gln Gln
        195                 200                 205
Trp Leu Ile Ala Val His Ser Ser Ile Phe Ser Ser Val Ala Ala Ser
        210                 215                 220
Cys Thr Leu Phe Val Val Leu Trp Leu Arg Val Pro Ile Leu Arg Thr
225                 230                 235                 240
Val Phe Gly Phe Arg Trp Leu Gly Ala Ile Phe Leu Ser Asn Ser Gln
                245                 250                 255

(2) INFORMATION FOR SEQ ID NO:15:

(i) SEQUENCE CHARACTERISTICS:
        (A) LENGTH: 249 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (C) INDIVIDUAL ISOLATE: Lelystad virus (xi) SEQUENCE DESCRIPTION: SEQ ID NO:15:

Met Gln Trp Gly His Cys Gly Val Lys Ser Ala Ser Cys Ser Trp Thr
1               5                   10                  15
Pro Ser Leu Ser Ser Leu Leu Val Trp Leu Ile Leu Pro Phe Ser Leu
                20                  25                  30
Pro Tyr Cys Leu Gly Ser Pro Ser Gln Asp Gly Tyr Trp Ser Phe Phe
                35                  40                  45
Ser Glu Trp Phe Ala Pro Arg Phe Ser Val Arg Ala Leu Pro Phe Thr
    50                  55                  60
Leu Pro Asn Tyr Arg Arg Ser Tyr Glu Gly Leu Leu Pro Asn Cys Arg
65                  70                  75                  80
```

```
Pro Asp Val Pro Gln Phe Ala Val Lys His Pro Leu Gly Met Phe Trp
                85                  90                  95

His Met Arg Val Ser His Leu Ile Asp Glu Met Val Ser Arg Arg Ile
            100                 105                 110

Tyr Gln Thr Met Glu His Ser Gly Gln Ala Ala Trp Lys Gln Val Val
        115                 120                 125

Gly Glu Ala Thr Leu Thr Lys Leu Ser Gly Leu Asp Ile Val Thr His
    130                 135                 140

Phe Gln His Leu Ala Ala Val Glu Ala Asp Ser Cys Arg Phe Leu Ser
145                 150                 155                 160

Ser Arg Leu Val Met Leu Lys Asn Leu Ala Val Gly Asn Val Ser Leu
                165                 170                 175

Gln Tyr Asn Thr Thr Leu Asp Arg Val Glu Leu Ile Phe Pro Thr Pro
            180                 185                 190

Gly Thr Arg Pro Lys Leu Thr Asp Phe Arg Gln Trp Leu Ile Ser Val
        195                 200                 205

His Ala Ser Ile Phe Ser Ser Val Ala Ser Ser Val Thr Leu Phe Ile
    210                 215                 220

Val Leu Trp Leu Arg Ile Pro Ala Leu Arg Tyr Val Phe Gly Phe His
225                 230                 235                 240

Trp Pro Thr Ala Thr His His Ser Ser
                245

(2) INFORMATION FOR SEQ ID NO:16:

(i) SEQUENCE CHARACTERISTICS:
        (A) LENGTH: 254 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: VR2385

(xi) SEQUENCE DESCRIPTION: SEQ ID NO:16:

Met Ala Asn Ser Cys Thr Phe Leu Tyr Ile Phe Leu Cys Cys Ser Phe
1               5                   10                  15

Leu Tyr Ser Phe Cys Cys Ala Val Val Ala Gly Ser Asn Ala Thr Tyr
                20                  25                  30

Cys Phe Trp Phe Pro Leu Val Arg Gly Asn Phe Ser Phe Glu Leu Thr
            35                  40                  45

Val Asn Tyr Thr Val Cys Pro Pro Cys Leu Thr Arg Gln Ala Ala Ala
    50                  55                  60

Glu Ala Tyr Glu Pro Gly Arg Ser Leu Trp Cys Arg Ile Gly His Asp
65                  70                  75                  80

Arg Cys Gly Glu Asp Asp His Asp Glu Leu Gly Phe Val Val Pro Ser
                85                  90                  95

Gly Leu Ser Ser Glu Gly His Leu Thr Ser Ala Tyr Ala Trp Leu Ala
            100                 105                 110

Ser Leu Ser Phe Ser Tyr Thr Thr Gln Phe His Pro Glu Ile Phe Gly
        115                 120                 125

Ile Gly Asn Val Ser Arg Val Tyr Val Asp Ile Lys His Gln Phe Ile
    130                 135                 140

Cys Ala Val His Asp Gly Gln Asn Thr Thr Leu Pro His His Asp Asn
```

```
                         145                 150                 155                 160
Ile Ser Ala Val Leu Gln Thr Tyr Tyr Gln His Gln Val Asp Gly Gly
                    165                 170                 175

Asn Trp Phe His Leu Glu Trp Val Arg Pro Phe Phe Ser Ser Trp Leu
                180                 185                 190

Val Leu Asn Val Ser Trp Phe Leu Arg Arg Ser Pro Ala Ser His Val
            195                 200                 205

Ser Val Arg Val Phe Gln Thr Ser Arg Pro Thr Pro Gln Arg Gln
        210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Ala Arg Arg
                245                 250
```

(2) INFORMATION FOR SEQ ID NO:17:

(i) SEQUENCE CHARACTERISTICS:
  (A) LENGTH: 254 amino acids
  (B) TYPE: amino acid
  (C) STRANDEDNESS:
  (D) TOPOLOGY: linear (ii) MOLECULE TYPE: protein (vi) ORIGINAL SOURCE:
  (A) ORGANISM: Porcine reproductive and respiratory virus
  (B) STRAIN: Iowa
  (C) INDIVIDUAL ISOLATE: ISU55

(xi) SEQUENCE DESCRIPTION: SEQ ID NO:17:

```
Met Ala Asn Ser Cys Thr Phe Leu Tyr Ile Phe Leu Cys Cys Ser Phe
1               5                   10                  15

Leu Tyr Ser Phe Cys Cys Ala Val Val Ala Gly Ser Asn Ala Thr Tyr
            20                  25                  30

Cys Phe Trp Phe Pro Leu Val Arg Gly Asn Phe Ser Phe Glu Leu Thr
        35                  40                  45

Val Asn Tyr Thr Val Cys Pro Pro Cys Leu Thr Arg Gln Ala Ala Thr
    50                  55                  60

Glu Ala Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Val Val Pro Ser
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Gln Val Tyr Val Asp Ile Arg His Gln Phe Ile
    130                 135                 140

Cys Ala Val His Asp Gly Gln Asn Ala Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Ser His Val
        195                 200                 205

Ser Val Arg Val Leu Gln Thr Leu Arg Pro Thr Pro Pro Gln Arg Gln
    210                 215                 220
```

```
Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Val Val Arg Arg
                245                 250
```

(2) INFORMATION FOR SEQ ID NO:18:

(i) SEQUENCE CHARACTERISTICS:
        (A) LENGTH: 254 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU79

(xi) SEQUENCE DESCRIPTION: SEQ ID NO:18:

```
Met Ala Asn Ser Cys Ala Phe Leu His Ile Phe Leu Cys Cys Ser Phe
1               5                   10                  15

Leu Tyr Ser Leu Cys Cys Ala Val Val Ala Gly Ser Asn Thr Thr Tyr
                20                  25                  30

Cys Phe Trp Phe Pro Leu Val Arg Gly Asn Phe Ser Phe Glu Leu Ile
            35                  40                  45

Val Asn Tyr Thr Val Cys Pro Pro Cys Leu Thr Arg Gln Ala Ala
    50                  55                  60

Glu Ala Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Ile Pro Ser
                85                  90                  95

Gly Leu Ser Ser Glu Gly His Leu Thr Ser Val Tyr Ala Trp Leu Ala
                100                 105                 110

Phe Leu Ser Phe Ser Tyr Thr Ala Gln Phe His Pro Glu Ile Phe Gly
                115                 120                 125

Ile Gly Asn Val Ser Arg Val Tyr Val Asp Ile Lys His Gln Leu Ile
130                 135                 140

Cys Ala Glu His Asp Gly Gln Asn Thr Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
                180                 185                 190

Val Leu Asn Val Ser Trp Phe Leu Arg Arg Ser Pro Ala Asn His Val
                195                 200                 205

Ser Val Arg Val Leu Gln Thr Leu Arg Pro Thr Pro Pro Gln Arg Gln
                210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250
```

(2) INFORMATION FOR SEQ ID NO:19:

(i) SEQUENCE CHARACTERISTICS:
        (A) LENGTH: 254 amino acids
        (B) TYPE: amino acid (C) STRANDEDNESS:
            (D) TOPOLOGY: linear (ii) MOLECULE TYPE: protein (vi) ORIGINAL SOURCE:
            (A) ORGANISM: Porcine reproductive and respiratory virus
            (B) STRAIN: Iowa
            (C) INDIVIDUAL ISOLATE: ISU1894

(xi) SEQUENCE DESCRIPTION: SEQ ID NO:19:

```
Met Val Asn Ser Cys Thr Phe Leu His Ile Phe Leu Cys Cys Ser Phe
1               5                   10                  15

Leu Tyr Ser Phe Cys Cys Ala Val Ala Ala Gly Ser Asn Ala Thr Tyr
            20                  25                  30

Cys Phe Trp Phe Pro Leu Val Arg Gly Asn Phe Ser Phe Glu Leu Met
        35                  40                  45

Val Asn Tyr Thr Val Cys Pro Pro Cys Leu Thr Arg Gln Ala Ala Ala
    50                  55                  60

Glu Val Tyr Glu Pro Gly Arg Ser Leu Trp Cys Arg Ile Gly Tyr Asp
65                  70                  75                  80

Arg Cys Gly Glu Asp Asp His Asp Glu Leu Gly Phe Met Ile Pro Pro
                85                  90                  95

Gly Leu Ser Ser Glu Gly His Leu Thr Ser Val Tyr Ala Trp Leu Ala
            100                 105                 110

Phe Leu Ser Phe Ser Tyr Thr Ala Gln Phe His Pro Glu Ile Phe Gly
        115                 120                 125

Ile Gly Asn Val Ser Arg Val Tyr Val Asp Ile Lys His Gln Leu Ile
    130                 135                 140

Cys Ala Glu His Asp Gly Gln Asn Ala Thr Leu Pro Arg His Asp Asn
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Tyr Leu Arg Arg Ser Pro Ala Asn His Ala
        195                 200                 205

Ser Val Arg Val Leu Gln Ile Leu Arg Pro Thr Leu Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250
```

(2) INFORMATION FOR SEQ ID NO:20:

(i) SEQUENCE CHARACTERISTICS:
(A) LENGTH: 254 amino acids
(B) TYPE: amino acid
(C) STRANDEDNESS:
(D) TOPOLOGY: linear (ii) MOLECULE TYPE: protein (vi) ORIGINAL SOURCE:
(A) ORGANISM: Porcine reproductive and respiratory virus
(B) STRAIN: Iowa
(C) INDIVIDUAL ISOLATE: ISU22

(xi) SEQUENCE DESCRIPTION: SEQ ID NO:20:

```
Met Val Asn Ser Cys Thr Phe Leu His Ile Phe Leu Cys Cys Ser Phe
```

```
  1               5                  10                 15
Leu Tyr Ser Phe Cys Cys Ala Val Val Ala Gly Ser Asn Thr Thr Phe
                20                 25                 30

Cys Phe Trp Phe Pro Leu Val Arg Gly Asn Phe Ser Phe Glu Leu Thr
                35                 40                 45

Val Asn Tyr Thr Val Cys Pro Pro Cys Leu Thr Arg Gln Ala Ala Ala
            50                 55                 60

Glu Ile Tyr Glu Pro Gly Arg Ser Leu Trp Cys Arg Ile Gly Tyr Asp
65                  70                 75                 80

Arg Cys Gly Glu Asp Asp His Asp Glu Leu Gly Phe Met Val Pro Pro
                85                 90                 95

Gly Phe Ser Ser Glu Gly His Leu Thr Ser Val Tyr Ala Trp Leu Ala
                100                105                110

Phe Leu Ser Phe Ser Tyr Thr Ala Gln Phe His Pro Glu Ile Phe Gly
                115                120                125

Ile Gly Asn Val Ser Arg Val Tyr Val Asp Ile Lys His Gln Leu Ile
                130                135                140

Cys Ala Glu His Asp Gly Gln Asn Thr Thr Leu Pro Arg His Asp Asn
145                 150                155                160

Ile Ser Ala Val Phe Gln Thr Tyr Tyr Gln His Gln Val Asp Gly Gly
                165                170                175

Asn Trp Phe His Leu Glu Trp Leu Arg Pro Phe Phe Ser Ser Trp Leu
                180                185                190

Val Leu Asn Val Ser Trp Phe Leu Arg Arg Ser Pro Ala Asn His Val
                195                200                205

Ser Val Arg Val Leu Gln Ile Leu Arg Pro Thr Pro Pro Gln Arg Gln
                210                215                220

Ala Leu Leu Ser Ser Lys Thr Ser Val Ala Leu Gly Ile Ala Thr Arg
225                 230                235                240

Pro Leu Arg Arg Phe Ala Lys Ser Leu Ser Ala Val Arg Arg
                245                250

(2) INFORMATION FOR SEQ ID NO:21:

(i) SEQUENCE CHARACTERISTICS:
        (A) LENGTH: 254 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU1894

(xi) SEQUENCE DESCRIPTION: SEQ ID NO:21:

Met Ala Asn Ser Cys Thr Phe Leu His Ile Leu Leu Cys Cys Ser Phe
1                   5                  10                 15

Leu Tyr Ser Phe Cys Cys Val Val Thr Asp Ala Asn Ala Thr Phe
                20                 25                 30

Cys Phe Trp Phe Pro Leu Val Arg Gly Asn Phe Ser Phe Glu Leu Met
                35                 40                 45

Val Asn Tyr Thr Val Cys Pro Pro Cys Leu Thr Arg Gln Ala Ala Ala
            50                 55                 60

Gln Ile Tyr Glu Pro Asn Arg Ser Leu Trp Cys Arg Ile Gly Asn Asp
65                  70                 75                 80
```

-continued

```
Arg Cys Gly Glu Asp Asp His Asp Glu Leu Gly Phe Thr Val Pro Pro
                85                  90                  95
Gly Leu Ser Lys Glu Val His Leu Thr Ser Val Tyr Ala Trp Leu Ala
            100                 105                 110
Phe Leu Ser Phe Ser Tyr Thr Ala Gln Phe His Pro Glu Ile Phe Gly
            115                 120                 125
Ile Gly Asn Val Ser Lys Val Tyr Val Asp Ile Asn His Gln Leu Ile
            130                 135                 140
Cys Ala Val His Asp Gly Gln Asn Thr Thr Leu Pro Arg His Asp Asn
145                 150                 155                 160
Ile Ser Ala Val Phe Gln Thr Tyr Tyr Gln His Gln Val Asp Gly Gly
                165                 170                 175
Asn Trp Phe His Leu Glu Trp Leu Arg Pro Phe Phe Ser Ser Trp Leu
                180                 185                 190
Val Leu Asn Val Ser Trp Phe Leu Arg Arg Ser Pro Ala Ser His Val
                195                 200                 205
Ser Val Arg Val Phe Gln Thr Ser Arg Pro Thr Pro Arg Gln Gln
            210                 215                 220
Ile Ser Leu Ser Ser Arg Thr Ser Ala Ala Leu Gly Met Ala Thr Arg
225                 230                 235                 240
Pro Leu Arg Arg Phe Ala Lys Ser Leu Ser Ala Ala Arg Arg
                245                 250
```

(2) INFORMATION FOR SEQ ID NO:22:

(i) SEQUENCE CHARACTERISTICS:
        (A) LENGTH: 254 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (C) INDIVIDUAL ISOLATE: VR2332

(xi) SEQUENCE DESCRIPTION: SEQ ID NO:22:

```
Met Val Asn Ser Cys Thr Phe Leu His Ile Phe Leu Cys Cys Ser Phe
1               5                   10                  15
Leu Tyr Ser Phe Cys Cys Ala Val Val Ala Gly Ser Asn Thr Thr Tyr
            20                  25                  30
Cys Phe Trp Phe Pro Leu Val Arg Gly Asn Phe Ser Phe Glu Leu Thr
            35                  40                  45
Val Asn Tyr Thr Val Cys Pro Pro Cys Leu Thr Arg Gln Ala Ala Thr
50              55                  60
Glu Ile Tyr Glu Pro Gly Arg Ser Leu Trp Cys Arg Ile Gly Tyr Asp
65                  70                  75                  80
Arg Cys Gly Glu Asp Asp His Asp Glu Leu Gly Phe Met Ile Pro Pro
                85                  90                  95
Gly Leu Ser Ser Glu Gly His Leu Thr Gly Val Tyr Ala Trp Leu Ala
            100                 105                 110
Phe Leu Ser Phe Ser Tyr Thr Ala Gln Phe His Pro Glu Ile Phe Gly
            115                 120                 125
Ile Gly Asn Val Ser Arg Val Tyr Val Asp Ile Lys His Gln Leu Ile
            130                 135                 140
Cys Ala Glu His Asp Gly Gln Asn Thr Thr Leu Pro Arg His Asp Asn
```

-continued

```
145                 150                 155                 160

Ile Ser Ala Val Phe Gln Thr Tyr Tyr Gln His Gln Val Asp Gly Gly
                165                 170                 175

Asn Trp Phe His Leu Glu Trp Leu Arg Pro Phe Phe Ser Ser Trp Leu
            180                 185                 190

Val Leu Asn Val Ser Trp Phe Leu Arg Arg Ser Pro Ala Asn His Val
        195                 200                 205

Ser Val Arg Val Leu Gln Ile Leu Arg Pro Thr Pro Pro Gln Arg Gln
    210                 215                 220

Ala Leu Leu Ser Ser Lys Thr Ser Val Ala Leu Gly Ile Ala Thr Arg
225                 230                 235                 240

Pro Leu Arg Arg Phe Ala Lys Ser Leu Ser Ala Val Arg Arg
                245                 250

(2) INFORMATION FOR SEQ ID NO:23:

(i) SEQUENCE CHARACTERISTICS:
          (A) LENGTH: 265 amino acids
          (B) TYPE: amino acid
          (C) STRANDEDNESS:
          (D) TOPOLOGY: linear (ii) MOLECULE TYPE: protein (vi) ORIGINAL SOURCE:
          (A) ORGANISM: Porcine reproductive and respiratory virus
          (C) INDIVIDUAL ISOLATE: Lelystad virus (xi) SEQUENCE DESCRIPTION: SEQ ID NO:23:

Met Ala His Gln Cys Ala Arg Phe His Phe Phe Leu Cys Gly Phe Ile
1               5                   10                  15

Cys Tyr Leu Val His Ser Ala Leu Ala Ser Asn Ser Ser Ser Thr Leu
            20                  25                  30

Cys Phe Trp Phe Pro Leu Ala His Gly Asn Thr Ser Phe Glu Leu Thr
        35                  40                  45

Ile Asn Tyr Thr Ile Cys Met Pro Cys Ser Thr Ser Gln Ala Ala Arg
    50                  55                  60

Gln Arg Leu Glu Pro Gly Arg Asn Met Trp Cys Lys Ile Gly His Asp
65                  70                  75                  80

Arg Cys Glu Glu Arg Asp His Asp Glu Leu Leu Met Ser Ile Pro Ser
                85                  90                  95

Gly Tyr Asp Asn Leu Lys Leu Glu Gly Tyr Tyr Ala Trp Leu Ala Phe
            100                 105                 110

Leu Ser Phe Ser Tyr Ala Ala Gln Phe His Pro Glu Leu Phe Gly Ile
        115                 120                 125

Gly Asn Val Ser Arg Val Phe Val Asp Lys Arg His Gln Phe Ile Cys
    130                 135                 140

Ala Glu His Asp Gly His Asn Ser Thr Val Ser Thr Gly His Asn Ile
145                 150                 155                 160

Ser Ala Leu Tyr Ala Ala Tyr Tyr His His Gln Ile Asp Gly Gly Asn
                165                 170                 175

Trp Phe His Leu Glu Trp Leu Arg Pro Leu Phe Ser Ser Trp Leu Val
            180                 185                 190

Leu Asn Ile Ser Trp Phe Leu Arg Arg Ser Pro Val Ser Pro Val Ser
        195                 200                 205

Arg Arg Ile Tyr Gln Ile Leu Arg Pro Thr Arg Pro Arg Leu Pro Val
    210                 215                 220
```

```
Ser Trp Ser Phe Arg Thr Ser Ile Val Ser Asp Leu Thr Gly Ser Gln
225                 230                 235                 240

Gln Arg Lys Arg Lys Phe Pro Ser Glu Ser Arg Pro Asn Val Val Lys
            245                 250                 255

Pro Ser Val Leu Pro Ser Thr Ser Arg
            260                 265
```

(2) INFORMATION FOR SEQ ID NO:24:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: VR2385

(xi) SEQUENCE DESCRIPTION: SEQ ID NO:24:

```
Met Gly Ala Ser Leu Leu Phe Leu Leu Val Gly Phe Lys Cys Leu Leu
1               5                   10                  15

Val Ser Gln Ala Phe Ala Cys Lys Pro Cys Phe Ser Ser Ser Leu Ser
            20                  25                  30

Asp Ile Lys Thr Asn Thr Thr Ala Ala Ala Gly Phe Ala Val Leu Gln
            35                  40                  45

Asp Ile Ser Cys Leu Arg His Arg Asn Ser Ala Ser Glu Ala Ile Arg
50                  55                  60

Lys Val Pro Gln Cys Arg Thr Ala Ile Gly Thr Pro Val Tyr Ile Thr
65                  70                  75                  80

Val Thr Ala Asn Val Thr Asp Glu Asn Tyr Leu His Ser Ser Asp Leu
            85                  90                  95

Leu Met Leu Ser Ser Cys Leu Phe Tyr Ala Ser Glu Met Ser Glu Lys
            100                 105                 110

Gly Phe Lys Val Val Phe Gly Asn Val Ser Gly Ile Val Ala Val Cys
            115                 120                 125

Val Asn Phe Thr Ser Tyr Val Gln His Val Lys Glu Phe Thr Gln Arg
            130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Thr Ile Leu Leu
            165                 170                 175

Ala Ile
```

(2) INFORMATION FOR SEQ ID NO:25:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (C) INDIVIDUAL ISOLATE: VR2332

(xi) SEQUENCE DESCRIPTION: SEQ ID NO:25:

```
Met Ala Ser Ser Leu Leu Phe Leu Val Val Gly Phe Lys Cys Leu Leu
1               5                   10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ser Phe Ala Val Leu Gln
        35                  40                  45

Asp Ile Ser Cys Leu Arg His Arg Asp Ser Ala Ser Glu Ala Ile Arg
50                  55                  60

Lys Ile Pro Gln Cys Arg Thr Ala Ile Gly Thr Pro Val Tyr Val Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
            115                 120                 125

Val Asn Phe Thr Ser Tyr Val Gln His Val Lys Glu Phe Thr Gln Arg
130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile (2) INFORMATION FOR SEQ ID NO:26:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU55

(xi) SEQUENCE DESCRIPTION: SEQ ID NO:26:

Met Ala Ala Ser Leu Leu Phe Leu Leu Val Gly Phe Lys Cys Leu Leu
1               5                   10                  15

Val Ser Gln Ala Phe Ala Cys Lys Pro Cys Phe Ser Ser Ser Leu Ala
            20                  25                  30

Asp Ile Lys Thr Asn Thr Thr Ala Ala Ala Gly Phe Ala Val Leu Gln
        35                  40                  45

Asp Ile Ser Cys Leu Arg Tyr Arg Asn Ser Ala Ser Glu Ala Phe Arg
50                  55                  60

Lys Ile Pro Gln Cys Arg Thr Ala Ile Gly Thr Pro Met Tyr Ile Thr
65                  70                  75                  80

Val Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
            115                 120                 125

Val Asn Phe Thr Ser Tyr Val Gln His Val Lys Glu Phe Thr Gln Arg
130                 135                 140
```

```
Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile (2) INFORMATION FOR SEQ ID NO:27:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU1894

(xi) SEQUENCE DESCRIPTION: SEQ ID NO:27:

Met Ala Ser Ser Leu Leu Phe Leu Met Val Gly Phe Lys Cys Leu Leu
1               5                   10                  15

Val Ser Gln Ala Phe Ala Cys Lys Pro Cys Phe Ser Ser Ser Leu Ala
                20                  25                  30

Asp Ile Lys Thr Asn Thr Thr Ala Ala Ala Ser Phe Ala Val Leu Gln
                35                  40                  45

Asp Ile Ser Cys Leu Arg His Arg Asn Ser Ala Ser Glu Ala Ile Arg
            50                  55                  60

Lys Ile Pro Gln Cys Arg Thr Ala Ile Gly Thr Pro Val Tyr Ile Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
            115                 120                 125

Val Asn Phe Thr Ser Tyr Val Gln His Val Arg Glu Phe Thr Gln Arg
    130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile (2) INFORMATION FOR SEQ ID NO:28:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU22

(xi) SEQUENCE DESCRIPTION: SEQ ID NO:28:
```

```
Met Ala Ser Ser Leu Leu Phe Leu Met Val Gly Phe Lys Cys Leu Leu
 1               5                  10                  15

Val Ser Gln Ala Phe Ala Cys Lys Pro Cys Phe Ser Ser Ser Leu Ala
                20                  25                  30

Asp Ile Lys Thr Asn Thr Thr Ala Ala Ala Ser Phe Ala Val Leu Gln
                35                  40                  45

Asp Ile Gly Cys Leu Arg His Arg Asp Ser Ala Ser Glu Ala Ile Arg
        50                  55                  60

Lys Ile Pro Gln Cys Arg Thr Ala Ile Gly Thr Pro Val Tyr Ile Thr
 65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Ile Val Ala Val Cys
                115                 120                 125

Val Asn Phe Thr Ser Tyr Val Gln His Val Arg Glu Phe Thr Gln Arg
        130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

(2) INFORMATION FOR SEQ ID NO:29:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU79

(xi) SEQUENCE DESCRIPTION: SEQ ID NO:29:

```
Met Ala Ala Ser Leu Leu Phe Leu Met Val Gly Phe Lys Cys Leu Leu
 1               5                  10                  15

Val Ser Gln Ala Phe Ala Cys Lys Pro Cys Phe Ser Ser Ser Leu Ala
                20                  25                  30

Asp Ile Lys Thr Asn Thr Thr Ala Ala Ala Ser Phe Ala Val Leu Gln
                35                  40                  45

Asp Ile Ser Cys Leu Arg His Arg Asn Ser Ala Ser Glu Ala Ile Arg
        50                  55                  60

Lys Ile Pro Gln Cys Arg Thr Ala Ile Gly Thr Pro Met Tyr Ile Thr
 65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Glu Val Val Phe Gly Asn Val Ser Gly Ile Val Ala Val Cys
                115                 120                 125

Val Asn Phe Thr Ser Tyr Val Gln His Val Arg Glu Phe Thr Gln Arg
```

```
              130                 135                 140
Ser Leu Met Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

(2) INFORMATION FOR SEQ ID NO:30:

(i) SEQUENCE CHARACTERISTICS:
        (A) LENGTH: 178 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU3927

(xi) SEQUENCE DESCRIPTION: SEQ ID NO:30:

```
Met Ala Ala Ser Leu Leu Phe Leu Leu Val Gly Phe Glu Cys Leu Leu
1               5                   10                  15

Val Ser Gln Ala Phe Ala Cys Lys Pro Cys Phe Ser Ser Ser Leu Ser
                20                  25                  30

Asp Ile Lys Thr Asn Thr Thr Ala Ala Ala Asn Phe Ala Val Leu Gln
                35                  40                  45

Asp Ile Gly Cys Leu Arg His Gly Asn Ser Thr Thr Glu Ala Phe Arg
50                  55                  60

Lys Ile Pro Gln Cys Arg Thr Ala Ile Gly Thr Pro Val Tyr Ile Thr
65                  70                  75                  80

Ile Thr Ala Asn Val Thr Asp Glu Asn Tyr Leu His Ser Ser Asp Leu
                85                  90                  95

Leu Met Leu Ser Ser Cys Leu Phe Tyr Ala Ser Glu Met Ser Glu Lys
                100                 105                 110

Gly Phe Lys Val Val Phe Gly Asn Val Ser Gly Thr Val Ala Val Cys
                115                 120                 125

Ile Asn Phe Thr Ser Tyr Val Gln His Val Lys Glu Phe Thr Gln Arg
                130                 135                 140

Ser Leu Val Val Asp His Val Arg Leu Leu His Phe Met Thr Pro Glu
145                 150                 155                 160

Thr Met Arg Trp Ala Thr Val Leu Ala Cys Leu Phe Ala Ile Leu Leu
                165                 170                 175

Ala Ile
```

(2) INFORMATION FOR SEQ ID NO:31:

(i) SEQUENCE CHARACTERISTICS:
        (A) LENGTH: 183 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (C) INDIVIDUAL ISOLATE: Lelystad virus (xi) SEQUENCE DESCRIPTION: SEQ ID NO:31:

```
Met Ala Ala Ala Thr Leu Phe Phe Leu Ala Gly Ala Gln His Ile Met
1               5                   10                  15

Val Ser Glu Ala Phe Ala Cys Lys Pro Cys Phe Ser Thr His Leu Ser
            20                  25                  30

Asp Ile Glu Thr Asn Thr Thr Ala Ala Gly Phe Met Val Leu Gln
        35                  40                  45

Asp Ile Asn Cys Phe Arg Pro His Gly Val Ser Ala Ala Gln Glu Lys
        50                  55                  60

Ile Ser Phe Gly Lys Ser Ser Gln Cys Arg Glu Ala Val Gly Thr Pro
65                  70                  75                  80

Gln Tyr Ile Thr Ile Thr Ala Asn Val Thr Asp Glu Ser Tyr Leu Tyr
                85                  90                  95

Asn Ala Asp Leu Leu Met Leu Ser Ala Cys Leu Phe Tyr Ala Ser Glu
            100                 105                 110

Met Ser Glu Lys Gly Phe Lys Val Ile Phe Gly Asn Val Ser Gly Val
            115                 120                 125

Val Ser Ala Cys Val Asn Phe Thr Asp Tyr Val Ala His Val Thr Gln
            130                 135                 140

His Thr Gln Gln His His Leu Val Ile Asp His Ile Arg Leu Leu His
145                 150                 155                 160

Phe Leu Thr Pro Ser Ala Met Arg Trp Ala Thr Thr Ile Ala Cys Leu
                165                 170                 175

Phe Ala Ile Leu Leu Ala Ile
                180
```

(2) INFORMATION FOR SEQ ID NO:32:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: VR2385

(xi) SEQUENCE DESCRIPTION: SEQ ID NO:32:

```
Met Leu Gly Lys Cys Leu Thr Ala Gly Cys Cys Ser Gln Leu Leu Phe
1               5                   10                  15

Leu Trp Cys Ile Val Pro Ser Cys Phe Val Ala Leu Val Ser Ala Asn
            20                  25                  30

Gly Asn Ser Gly Ser Asn Leu Gln Leu Ile Tyr Asn Leu Thr Leu Cys
        35                  40                  45

Glu Leu Asn Gly Thr Asp Trp Leu Ala Asn Lys Phe Asp Trp Ala Val
        50                  55                  60

Glu Cys Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Val His Gly Arg Tyr Val Leu Ser Ser Met Tyr
            100                 105                 110

Ala Val Cys Ala Leu Ala Ala Leu Ile Cys Phe Val Ile Arg Leu Ala
            115                 120                 125
```

```
Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Ala Ala Thr Pro Val Thr Arg Val
            180                 185                 190

Ser Ala Glu Gln Trp Arg Pro
            195
```

(2) INFORMATION FOR SEQ ID NO:33:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (C) INDIVIDUAL ISOLATE: VR2332

(xi) SEQUENCE DESCRIPTION: SEQ ID NO:33:

```
Met Leu Glu Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
            20                  25                  30

Asn Asp Ser Ser Ser His Leu Gln Leu Ile Tyr Asn Leu Thr Leu Cys
            35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Ala
            115                 120                 125

Lys Asn Cys Met Ser Trp Arg Tyr Ala Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Gly Arg Pro
            195
```

(2) INFORMATION FOR SEQ ID NO:34:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU55

(xi) SEQUENCE DESCRIPTION: SEQ ID NO:34:

Met Leu Gly Lys Cys Leu Thr Ala Gly Tyr Cys Ser Ser Leu Leu Phe
1               5                   10                  15

Leu Trp Cys Ile Val Pro Ser Trp Phe Val Ala Leu Ala Ser Ala Asn
                20                  25                  30

Ser Ser Asn Ser Ser His Leu Gln Leu Ile Tyr Asn Leu Thr Leu Cys
            35                  40                  45

Glu Leu Asn Gly Thr Asp Trp Leu Ala Gly Glu Phe Asp Trp Ala Val
        50                  55                  60

Glu Cys Phe Val Ile Phe Pro Val Leu Thr His Ile Val Ser Tyr Gly
65                  70                  75                  80

Ala Leu Thr Thr Ser His Phe Leu Asp Thr Val Gly Leu Val Thr Val
                85                  90                  95

Ser Thr Ala Gly Phe Ser His Gly Arg Tyr Val Leu Ser Ser Ile Tyr
            100                 105                 110

Ala Val Cys Ala Leu Ala Ala Leu Ile Cys Phe Val Ile Arg Phe Thr
        115                 120                 125

Lys Asn Cys Met Ser Trp Arg Tyr Ser Cys Thr Arg Tyr Thr Asn Phe
        130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Ala Ala Thr Pro Ile Thr Lys Val
                180                 185                 190

Ser Ala Glu Gln Gly Arg Pro
            195

(2) INFORMATION FOR SEQ ID NO:35:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU1894

(xi) SEQUENCE DESCRIPTION: SEQ ID NO:35:

Met Leu Gly Lys Cys Leu Thr Ala Gly Cys Cys Ser Arg Leu Leu Ser
1               5                   10                  15

Leu Trp Cys Ile Val Pro Phe Cys Phe Ala Val Leu Ala Asn Ala Ser
                20                  25                  30

Ala Asn Ser Ser Ser His Leu Gln Leu Ile Tyr Asn Leu Thr Leu Cys
            35                  40                  45

Glu Leu Asn Gly Thr Asp Trp Leu Ala Asp Lys Phe Asp Trp Ala Val
        50                  55                  60

```
Glu Ser Phe Val Ile Phe Pro Val Leu Thr His Ile Val Ser Tyr Gly
 65                  70                  75                  80

Ala Leu Thr Thr Ser His Leu Leu Asp Thr Val Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Ala Cys Phe Val Ile Arg Phe Ala
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp His Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
                180                 185                 190

Ser Ala Glu Gln Gly Arg Pro
            195

(2) INFORMATION FOR SEQ ID NO:36:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU79

(xi) SEQUENCE DESCRIPTION: SEQ ID NO:36:

Met Leu Gly Lys Cys Leu Thr Val Gly Cys Cys Ser Arg Leu Leu Ser
1               5                   10                  15

Leu Trp Cys Ile Val Pro Phe Cys Phe Thr Val Leu Ala Asp Ala His
                20                  25                  30

Ser Asn Ser Ser Ser His Leu Gln Leu Ile Tyr Asn Leu Thr Leu Cys
            35                  40                  45

Glu Leu Asn Gly Thr Asp Trp Leu Ala Asp Arg Phe Asp Trp Ala Val
 50                  55                 60

Glu Ser Phe Val Ile Phe Pro Val Leu Thr His Ile Val Ser Tyr Gly
 65                  70                  75                  80

Ala Leu Thr Thr Ser His Phe Leu Asp Thr Ile Ala Leu Val Thr Val
                 85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Val Ile Arg Phe Val
        115                 120                 125

Lys Asn Cys Met Ser Trp Arg Tyr Ser Cys Thr Arg Tyr Thr Asn Phe
130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
```

```
                  180                 185                 190

Ser Ala Glu Gln Gly Arg Pro
            195

(2) INFORMATION FOR SEQ ID NO:37:

(i) SEQUENCE CHARACTERISTICS:
        (A) LENGTH: 199 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU22

(xi) SEQUENCE DESCRIPTION: SEQ ID NO:37:

Met Leu Gly Lys Cys Leu Thr Ala Gly Cys Cys Ser Arg Leu Leu Ser
1               5                  10                  15

Leu Trp Phe Ile Val Pro Phe Cys Phe Ala Val Leu Ala Ser Ala Ser
            20                  25                  30

Asn Ser Ser Ser Ser His Leu Gln Leu Ile Tyr Asn Leu Thr Leu Cys
        35                  40                  45

Glu Leu Asn Gly Thr Asp Trp Leu Ala Asn Lys Phe Asp Trp Ala Val
50                  55                  60

Glu Ser Phe Val Ile Phe Pro Val Leu Thr His Ile Val Ser Tyr Gly
65                  70                  75                  80

Ala Leu Thr Thr Ser His Phe Leu Asp Thr Val Ala Leu Val Thr Val
                85                  90                  95

Ser Thr Ala Gly Phe Val His Gly Arg Tyr Val Leu Ser Ser Ile Tyr
            100                 105                 110

Ala Val Cys Ala Leu Ala Ala Leu Thr Cys Phe Ile Ile Arg Phe Ala
        115                 120                 125

Lys Asn Cys Met Ser Trp Arg Tyr Ser Cys Thr Arg Tyr Thr Asn Phe
    130                 135                 140

Leu Leu Asp Thr Lys Gly Arg Leu Tyr Arg Trp Arg Ser Pro Val Ile
145                 150                 155                 160

Ile Glu Lys Arg Gly Lys Val Glu Val Glu Gly His Leu Ile Asp Leu
                165                 170                 175

Lys Arg Val Val Leu Asp Gly Ser Val Ala Thr Pro Ile Thr Arg Val
            180                 185                 190

Ser Ala Glu Gln Gly Arg Pro
            195

(2) INFORMATION FOR SEQ ID NO:38:

(i) SEQUENCE CHARACTERISTICS:
        (A) LENGTH: 198 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (B) STRAIN: Iowa
        (C) INDIVIDUAL ISOLATE: ISU3927

(xi) SEQUENCE DESCRIPTION: SEQ ID NO:38:
```

```
Met Leu Gly Lys Cys Leu Thr Ala Gly Cys Cys Ser Arg Ser Leu Phe
1               5                   10                  15

Leu Trp Cys Ile Val Pro Phe Cys Leu Ala Ala Leu Val Ser Ala Asn
            20                  25                  30

Asn Ser Ser Ser His Leu Gln Leu Ile Tyr Asn Leu Thr Leu Cys Glu
        35                  40                  45

Leu Asn Gly Thr Asp Trp Leu Ala Asn Lys Phe Asp Trp Ala Val Glu
        50                  55                  60

Ser Phe Val Ile Phe Pro Val Leu Thr His Ile Val Ser Tyr Gly Ala
65                  70                  75                  80

Leu Thr Thr Ser His Phe Leu Asp Thr Val Gly Leu Val Thr Val Ser
                85                  90                  95

Thr Ala Gly Phe His His Gly Arg Tyr Val Leu Ser Ser Ile Tyr Ala
            100                 105                 110

Val Cys Ala Leu Ala Ala Phe Ile Cys Phe Val Ile Arg Phe Ala Lys
            115                 120                 125

Asn Cys Met Ser Trp Arg Tyr Ser Cys Thr Arg Tyr Thr Asn Phe Leu
        130                 135                 140

Leu Asp Thr Lys Gly Arg Leu Tyr Arg Trp Arg Ser Pro Val Ile Ile
145                 150                 155                 160

Glu Lys Gly Gly Lys Val Glu Val Glu Gly His Leu Ile Asp Leu Lys
                165                 170                 175

Lys Val Val Leu Asp Gly Ser Ala Ala Thr Pro Leu Thr Arg Val Ser
            180                 185                 190

Ala Glu Gln Gly Arg Pro
                195

(2) INFORMATION FOR SEQ ID NO:39:

(i) SEQUENCE CHARACTERISTICS:
        (A) LENGTH: 200 amino acids
        (B) TYPE: amino acid
        (C) STRANDEDNESS:
        (D) TOPOLOGY: linear (ii) MOLECULE TYPE: protein (vi) ORIGINAL SOURCE:
        (A) ORGANISM: Porcine reproductive and respiratory virus
        (C) INDIVIDUAL ISOLATE: Lelystad virus (xi) SEQUENCE DESCRIPTION: SEQ ID NO:39:

Met Arg Cys Ser His Lys Leu Gly Arg Phe Leu Thr Pro His Ser Cys
1               5                   10                  15

Phe Trp Trp Leu Phe Leu Leu Cys Thr Gly Leu Ser Trp Ser Phe Ser
            20                  25                  30

Asp Asn Gly Gly Asp Ser Ser Thr Tyr Gln Tyr Ile Tyr Asn Leu Thr
        35                  40                  45

Ile Cys Glu Leu Asn Gly Thr Asp Trp Leu Ser Ser His Phe Gly Trp
        50                  55                  60

Ala Val Glu Thr Phe Val Leu Tyr Pro Val Ala Thr His Ile Leu Ser
65                  70                  75                  80

Leu Gly Phe Leu Thr Thr Ser His Phe Phe Asp Ala Leu Gly Leu Gly
                85                  90                  95

Ala Val Ser Thr Ala Gly Phe Val Gly Gly Arg Tyr Val Leu Cys Ser
            100                 105                 110

Val Tyr Gly Ala Cys Ala Phe Ala Ala Phe Val Cys Phe Val Ile Arg
```

```
              115                 120                 125
Ala Ala Lys Asn Cys Met Ala Cys Arg Tyr Ala Arg Thr Arg Phe Thr
        130                 135                 140

Asn Phe Ile Val Asp Asp Arg Gly Arg Val His Arg Trp Lys Ser Pro
145                 150                 155                 160

Ile Val Val Glu Lys Leu Gly Lys Ala Glu Val Asp Gly Asn Leu Val
                165                 170                 175

Thr Ile Lys His Val Val Leu Glu Gly Val Lys Ala Gln Pro Leu Thr
                180                 185                 190

Arg Thr Ser Ala Glu Gln Glu Ala
            195                 200

(2) INFORMATION FOR SEQ ID NO:40:

(i) SEQUENCE CHARACTERISTICS:
        (A) LENGTH: 3293 base pairs
        (B) TYPE: nucleic acid
        (C) STRANDEDNESS: unknown
        (D) TOPOLOGY: unknown (ii) MOLECULE TYPE: cDNA (vi) ORIGINAL SOURCE:
        (A) ORGANISM: Porcine reproductive and respiratory virus
        (B) STRAIN: Iowa
        (C) INDIVIDUAL ISOLATE: ISU79

(xi) SEQUENCE DESCRIPTION: SEQ ID NO:40:

GTTTTATTTC CCTCCGGGCC CTGTCATTGA ACCAACTTTA GGCCTGAATT GAAATGAAAT      60

GGGGTCCATG CAAAGCCTTT TTGACAAAAT TGGCCAACTT TTTGTGGATG CTTTCACGGA     120

GTTCTTGGTG TCCATTGTTG ATATCATTAT ATTCTTGGCC ATTTTGTTTG CTTCACCAT      180

CGCCGGTTGG CTGGTGGTCT TTTGCATCAG ATTGGTTTGC TCCGCGATAC TCCGTACGCG     240

CCCTGCCATT CACTCTGAGC AATTACAGAA GATCTTATGA GGCCTTTCTT TCCCAGTGCC     300

AAGTGGACAT TCCCACCTGG GGAACTAAAC ATCCTTTGGG GATGTTTTGG CACCATAAGG     360

TGTCAACCCT GATTGATGAG ATGGTGTCGC GTCGAATGTA CCGCATCATG GAAAAAGCAG     420

GACAGGCTGC CTGGAAACAG GTGGTGAGCG AGGCTACGCT GTCTCGCATT AGTAGTTTGG     480

ATGTGGTGGC TCATTTTCAG CATCTTGCCG CCATCGAAGC CGAGACCTGT AAATATTTGG     540

CCTCCCGGCT GCCCATGCTA CACAACCTGC GCATGACAGG GTCAAATGTA CCATAGTGT      600

ATAATAGTAC TTTGAATCGG GTGTTTGCTA TTTTCCCAAC CCCTGGTTCC CGGCCAAAGC     660

TTCATGACTT TCAGCAATGG CTAATAGCTG TGCATTCCTC CATATTTTCC TCTGTTGCAG     720

CTTCTTGTAC TCTCTTTGTT GTGCTGTGGT TGCGGGTTCC AATACTACGT ACTGTTTTTG     780

GTTTCCGCTG GTTAGGGGCA ATTTTTCTTT CGAACTCATA GTGAATTACA CGGTGTGCCC     840

ACCTTGCCTC ACCCGGCAAG CAGCCGCAGA GGCCTACGAA CCCGGTAGGT CTCTTTGGTG     900

CAGGATAGGG TACGATCGAT GTGGAGAGGA CGACCATGAC GAGCTAGGGT TTATGATACC     960

GTCTGGCCTC TCCAGCGAAG GCCACTTGAC CAGTGTTTAC GCCTGGTTGG CGTTCTTGTC    1020

CTTCAGCTAC ACGGCCCAGT TCCACCCCGA GATATTCGGG ATAGGGAATG TGAGTCGAGT    1080

TTATGTTGAC ATCAAACATC AACTCATCTG CGCCGAACAT GACGGGCAGA ACACCACCTT    1140

GCCTCGTCAT GACAACATTT CGGCCGTGTT TCAGACCTAT ACCAACATCA AGTCGACGG     1200

CGGCAATTGG TTTCACCTAG AATGGCTGCG TCCCTTCTTT TCCTCATGGT TGGTTTTAAA    1260

TGTCTCTTGG TTTCTCAGGC GTTCGCCTGC AAACCATGTT TCAGTTCGAG TCTTGCAGAC    1320
```

-continued

```
ATTAAGACCA ACACCACCGC AGCGGCAAGC TTTGCTGTCC TCCAAGACAT CAGTTGCCTT    1380

AGGCATCGCA ACTCGGCCTC TGAGGCGATT CGCAAAATCC CTCAGTGCCG TACGGCGATA    1440

GGGACACCTA TGTATATTAC CATCACAGCC AATGTGACAG ATGAAAATTA TTTACATTCT    1500

TCTGATCTCC TCATGCTCTC TTCTTGCCTT TTCTATGCTT CTGAGATGAG TGAAAAGGGA    1560

TTTGAGGTGG TTTTTGGCAA TGTGTCAGGC ATCGTGGCTG TGTGTGTCAA TTTTACCAGC    1620

TACGTTCAAC ATGTCAGGGA GTTTACCCAA CGCTCCTTGA TGGTCGACCA TGTGCGGCTG    1680

CTCCATTTCA TGACACCTGA GACCATGAGG TGGGCAACCG TTTTAGCCTG TCTTTTTGCT    1740

ATTCTGTTGG CAATTTGAAT GTTAAGTAT GTTGGGAAA TGCTTGACCG TGGGCTGTTG     1800

CTCGCGATTG CTTTCTTTGT GGTGTATCGT GCCGTTCTGT TTTACTGTGC TCGCCGACGC    1860

CCACAGCAAC AGCAGCTCTC ATCTGCAATT GATTTACAAC TTGACGCTAT GTGAGCTGAA    1920

TGGCACAGAT TGGCTAGCTG ATAGATTTGA TTGGGCAGTG GAGAGCTTTG TCATCTTTCC    1980

TGTTTTGACT CACATTGTCT CCTATGGCGC CCTCACCACC AGCCATTTCC TTGACACAAT    2040

TGCTTTAGTC ACTGTGTCTA CCGCCGGGTT TGTTCACGGG CGGTATGTCC TAAGTAGCAT    2100

CTACGCGGTC TGTGCCCTGG CTGCGTTGAC TTGCTTCGTC ATTAGGTTTG TGAAGAATTG    2160

CATGTCCTGG CGCTACTCAT GTACTAGATA TACCAACTTT CTTCTGGATA CTAAGGGCAG    2220

ACTCTATCGT TGGCGGTCGC CTGTCATCAT AGAGAAGAGG GGCAAAGTTG AGGTCGAAGG    2280

TCATCTGATC GATCTCAAAA GAGTTGTGCT TGATGGTTCC GTGGCAACCC CTATAACCAG    2340

AGTTTCAGCG GAACAATGGG GTCGTCCTTA GATGACTTCT GTTATGATAG TACGGCTCCA    2400

CAAAAGGTGC TTTTGGCATT TTCTATTACC TACACGCCAG TAATGATATA TGCCCTAAAG    2460

GTGAGTCGCG GCCGACTGCT AGGGCTTCTG CACCTTTTGA TTTTCCTGAA CTGTGCTTTC    2520

ACCTTCGGGT ACATGACATT CATGCACTTT CAGAGTACAA ATAAGGTCGC GCTCACTATG    2580

GGAGCAGTAG TTGCACTCCT TTGGGGGGTG TACTCAGCCA TAGAAACCTG GAAATTCATC    2640

ACCTCCAGAT GCCGTTTGTG CTTGCTAGGC CGCAAGTACA TTCTGGCCCC TGCCCACCAC    2700

GTTGAAAGTG CCGCAGGCTT TCATCCGATT GCGGCAAATG ATAACCACGC ATTTGTCGTC    2760

CGGCGTCCCG GCTCCACTAC GGTCAACGGC ACATTGGTGC CCGGGTTGAA AAGCCTCGTG    2820

TTGGGTGGCA GAAAAGCTGT TAAACAGGGA GTGGTAAACC TTGTCAAATA TGCCAAATAA    2880

CAACGGCAAG CAGCAGAAGA GAAAGAAGGG GGATGGCCAG CCAGTCAATC AGCTGTGCCA    2940

GATGCTGGGT AAGATCATCG CCCAGCAAAA CCAGTCTAGA GGCAAGGGAC CGGGAAAGAA    3000

AAATAAGAAG AAAAACCCGG AGAAGCCCCA TTTTCCTCTA GCGACTGAAG ATGATGTCAG    3060

ACATCACTTT ACCCCTAGTG AGCGGCAATT GTGTCTGTCG TCAATCCAAA CTGCCTTTAA    3120

TCAAGGCGCT GGGACTTGCA CCCTGTCAGA TTCAGGGAGG ATAAGTTACA CTGTGGAGTT    3180

TAGTTTGCCT ACGCATCATA CTGTGCGCTT GATCCGCGTC ACAGCATCAC CCTCAGCATG    3240

ATGGGCTGGC ATTCTTGAGG CATCCCAGTG TTTGAATTGG AAGAATGCGT GGT          3293
```

(2) INFORMATION FOR SEQ ID NO:41:

(i) SEQUENCE CHARACTERISTICS:
  (A) LENGTH: 3293 base pairs
  (B) TYPE: nucleic acid
  (C) STRANDEDNESS: unknown
  (D) TOPOLOGY: unknown (ii) MOLECULE TYPE: cDNA (vi) ORIGINAL SOURCE:
  (A) ORGANISM: Porcine reproductive and respiratory virus (B) STRAIN: Iowa
(C) INDIVIDUAL ISOLATE: ISU1894

(xi) SEQUENCE DESCRIPTION: SEQ ID NO:41:

```
GTTTTATTTC CCTCCGGGCC CCGTCATTGA ACCAACTTTA GGCCTGAATT GAAATGAAAT      60
GGGGTCCGTG CAAAGCCTTT TTGACAAAAT TGGCCAACTT TTTGTGGATG CTTTCACGGA     120
GTTCCTGGTG TCCATTGTTG ATATCATCAT ATTTTTGGCC ATTTTGTTTG GCTTCACCAT     180
CGCCGGTTGG CTGGTGGTCT TTTGCATCAG ATTGGTTTGC TCCGCGATAC TCCGTACGCG     240
CCCTGCCATT CACTCTGAGC AATTACAGAA GATCTTATGA GGCCTTTTTA TCCCAGTGCC     300
AAGTGGACAT TCCCACCTGG GGAACTAAAC ATCCTTTGGG GATGTTTTGG CACCATAAGG     360
TGTCAACCCT GATTGATGAA ATGGTGTCGC GTCGCATGTA CCGCATCATG GAAAAAGCAG     420
GGCAGGCTGC CTGGAAACAG GTGGTGAGCG AGGCTACGCT GTCCCGCATT AGTAGTTTGG     480
ATGTGGTGGC TCATTTTCAG CATCTTGCCG CCATTGAAGC CGAGACTTGT AAATATTTGG     540
CCTCCCGGCT GCCCATGCTA CATAACCTGC GCATAACAGG GTCAAATGTA ACCATAGTGT     600
ATAATAGTAC TTCGGAGCAG GTGTTTGCTA TTTTCCCAAC CCCTGGTTCC CGGCCAAAGC     660
TTCATGATTT TCAGCAATGG TTAATAGCTG TACATTCCTC CATATTTTCC TCTGTTGCAG     720
CTTCTTGTAC TCTTTTTGTT GTGCTGTGGC TGCGGGTTCC AATGCTACGT ACTGTTTTTG     780
GTTTCCGCTG GTTAGGGGGA ATTTTTCCTT CGAACTCATG GTGAATTACA CGGTGTGTCC     840
ACCTTGCCTC ACCCGGCAAG CAGCCGCAGA GGTCTACGAA CCCGGTAGGT CTCTTTGGTG     900
CAGGATAGGG TATGACCGAT GTGGGAGGA CGATCATGAC GAGCTAGGGT TTATGATACC      960
GCCTGGCCTC TCCAGCGAAG GCCACTTGAC TAGTGTTTAC GCCTGGTTGG CGTTTTTGTC    1020
CTTCAGCTAC ACGGCCCAGT TCCATCCCGA GATATTCGGG ATAGGGAATG TGAGTCGAGT    1080
TTATGTTGAC ATCAAACATC AACTCATTTG CGCCGAACAT GACGGACAGA ACGCCACCTT    1140
GCCTCGTCAT GACAATATTT CAGCCGTGTT TCAGACCTAT TACCAACATC AAGTCGATGG    1200
CGGCAATTGG TTTCACCTAG AATGGCTTCG TCCCTTCTTT TCCTCATGGT TGGTTTTAAA    1260
TGTCTCTTGG TATCTCAGGC GTTCGCCTGC AAACCATGCT TCAGTTCGAG TCTTGCAGAT    1320
ATTAAGACCA ACACTACCGC AGCGGCAAGC TTTGCTGTCC TCCAAGACAT CAGTTGCCTT    1380
AGGCATCGCA ACTCGGCCTC TGAGGCGATT CGCAAAATCC CTCAGTGCCG TACGGCGATA    1440
GGGACACCCG TGTATATTAC CATCACAGCC AATGTGACAG ATGAGAATTA TTTACATTCT    1500
TCTGATCTCC TCATGCTTTC TTCTTGCCTT TTCTACGCTT CTGAGATGAG TGAAAAAGGA    1560
TTCAAGGTGG TATTTGGCAA TGTGTCAGGC ATCGTGGCTG TGTGTGTCAA TTTTACCAGC    1620
TACGTCCAAC ATGTCAGGGA GTTTACCCAA CGCTCCCTGG TGGTCGACCA TGTGCGGTTG    1680
CTCCATTTCA TGACACCTGA AACCATGAGG TGGGCAACTG TTTTAGCCTG TCTTTTTGCC    1740
ATTCTGCTGG CAATTTGAAT GTTTAAGTAT GTTGGGAAA TGCTTGACCG CGGGCTGTTG     1800
CTCGCGATTG CTTTCTTTGT GGTGTATCGT GCCGTTCTGT TTTGCTGTGC TCGCCAACGC    1860
CAGCGCCAAC AGCAGCTCCC ATCTACAGCT GATTTACAAC TTGACGCTAT GTGAGCTGAA    1920
TGGCACAGAT TGGCTAGCTG ATAAATTTGA TTGGGCAGTG GAGAGTTTTG TCATCTTTCC    1980
CGTTTTGACT CACATTGTCT CCTATGGTGC CCTCACTACT AGCCATCTCC TTGACACAGT    2040
CGCCTTAGTC ACTGTGTCTA CCGCCGGGTT TGTTCACGGG CGGTATGTCC TAAGTAGCAT    2100
CTACGCGGTC TGTGCCCTGG CTGCGTTAGC TTGCTTCGTC ATTAGGTTTG CAAAGAATTG    2160
CATGTCCTGG CGCTATTCGT GTACCAGATA TACCAACTTT CTTCTGGACA CTAAGGGCAG    2220
```

-continued

```
ACTCTATCGT TGGCATTCGC CTGTCATCAT AGAGAAAAGG GGCAAAGTTG AGGTCGAAGG      2280

TCATCTGATC GACCTCAAAA GAGTTGTGCT TGACGGTTCC GTGGCAACCC CTATAACCAG      2340

AGTTTCAGCG GAACAATGGG GTCGTCCTTA GATGACTTCT GCCATGATAG TACGGCTCCA      2400

CAAAAGGTGC TTTTGGCGTT TTCTATTACC TACACGCCAG TGATGATATA TGCCCTAAAG      2460

GTGAGTCGCG GCCGACTGCT AGGGCTTCTG CACCTTTTGA TCTTCCTGAA TTGTGCTTTC      2520

ACCTTCGGGT ACATGACATT CGTGCACTTT CAGAGTACAA ATAAGGTCGC GCTCACTATG      2580

GGAGCAGTAG TTGCACTCCT TTGGGGGGTG TACTCAGCCA TAGAAACCTG GAAATTCATC      2640

ACCTCCAGAT GCCGTTTGTG CTTGCTAGGC CGCAAGTACA TTCTGGCCCC TGCCCACCAC      2700

GTTGAAAGTG CCGCAGGCTT TCATCCGATT GCGGCAAATG ATAACCACGC ATTTGTCGTC      2760

CGGCGTCCCG GCTCCACTAC GGTCAACGGC ACATTGGTGC CCGGGTTGAA AAGCCTCGTG      2820

TTGGGTGGCA GAAAAGCTGT TAAACAGGGA GTGGTAAACC TTGTCAAATA TGCCAAATAA      2880

CAACGGCAAG CAGCAGAAGA GAAAGAAGGG GGATGGCCAG CCAGTCAATC AGCTGTGCCA      2940

GATGCTGGGT AAGATCATCG CTCAGCAAAA CCAGTCCAGA GGCAAGGGAC CGGGAAAGAA      3000

AAACAAGAAG AAAAACCCGG AGAAGCCCCA TTTTCCTCTA GCGACTGAAG ATGATGTCAG      3060

ACATCACTTC ACCCCTAGTG AGCGGCAATT GTGTCTGTCG TCAATCCAGA CCGCCTTTAA      3120

TCAAGGCGCT GGGACTTGCA CCCTGTCAGA TTCAGGGAGG ATAAGTTACA CTGTGGAGTT      3180

TAGTTTGCCA ACGCATCATA CTGTGCGCTT GATCCGCGTC ACAGCATCAC CCTCAGCATG      3240

ATGGGCTGGC ATTCTTGAGG CATCCCAGTG TTTGAATTGG AAGAATGCGT GGT            3293
```

(2) INFORMATION FOR SEQ ID NO:42:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Pro Ser Ser Ser Trp
1               5
```

(2) INFORMATION FOR SEQ ID NO:43:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:43:

```
Arg Gln Arg Ile Ser
1               5
```

(2) INFORMATION FOR SEQ ID NO:44:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:44:

Phe Gln Thr Ser
1

(2) INFORMATION FOR SEQ ID NO:45:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:45:

Asn Gly Asn Ser Gly Ser Asn
1               5

(2) INFORMATION FOR SEQ ID NO:46:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:46:

Ser Asn Asp Ser Ser Ser His
1               5

(2) INFORMATION FOR SEQ ID NO:47:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:47:

Ser Ser Ser Asn Ser Ser His
1               5

(2) INFORMATION FOR SEQ ID NO:48:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:48:

Ser Ala Asn Ser Ser Ser His
1               5

(2) INFORMATION FOR SEQ ID NO:49:

(i) SEQUENCE CHARACTERISTICS:
         (A) LENGTH: 7 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:49:

His Ser Asn Ser Ser Ser His
1               5

(2) INFORMATION FOR SEQ ID NO:50:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:50:

Ser Asn Ser Ser Ser Ser His
1               5

(2) INFORMATION FOR SEQ ID NO:51:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:51:

Asn Asn Ser Ser Ser Ser His
1               5

(2) INFORMATION FOR SEQ ID NO:52:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:52:

Asn Gly Gly Asp Ser Ser Thr
1               5

(2) INFORMATION FOR SEQ ID NO:53:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:53:

Asn Gly Gly Asp Ser Ser Tyr
1               5

(2) INFORMATION FOR SEQ ID NO:54:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:54:

Ala Asn Lys Phe Asp Trp Ala Val Glu Thr
1               5                   10

(2) INFORMATION FOR SEQ ID NO:55:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:55:

Ala Asn Lys Phe Asp Trp Ala Val Glu Pro
1               5                   10

(2) INFORMATION FOR SEQ ID NO:56:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:56:

Ala Gly Glu Phe Asp Trp Ala Val Glu Thr
1               5                   10

(2) INFORMATION FOR SEQ ID NO:57:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:57:

Ala Asp Lys Phe Asp Trp Ala Val Glu Pro
1               5                   10

(2) INFORMATION FOR SEQ ID NO:58:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:58:

Ala Asp Arg Phe Asp Trp Ala Val Glu Pro
1               5                   10

(2) INFORMATION FOR SEQ ID NO:59:

(i) SEQUENCE CHARACTERISTICS:
            (A) LENGTH: 10 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:59:

Ser Ser His Phe Gly Trp Ala Val Glu Thr
1               5                   10

(2) INFORMATION FOR SEQ ID NO:60:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:60:

Leu Ile Cys Phe Val Ile Arg Leu Ala
1               5

(2) INFORMATION FOR SEQ ID NO:61:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:61:

Leu Thr Cys Phe Val Ile Arg Phe Ala
1               5

(2) INFORMATION FOR SEQ ID NO:62:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:62:

Leu Ile Cys Phe Val Ile Arg Phe Thr
1               5

(2) INFORMATION FOR SEQ ID NO:63:

(i) SEQUENCE CHARACTERISTICS:
            (A) LENGTH: 9 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:63:

Leu Ala Cys Phe Val Ile Arg Phe Ala
1               5

(2) INFORMATION FOR SEQ ID NO:64:

(i) SEQUENCE CHARACTERISTICS:
            (A) LENGTH: 9 amino acids
            (B) TYPE: amino acid
            (C) STRANDEDNESS:

(D) TOPOLOGY: linear (ii) MOLECULE TYPE: peptide (xi) SEQUENCE DESCRIPTION: SEQ ID NO:64:

Leu Thr Cys Phe Val Ile Arg Phe Val
1               5

(2) INFORMATION FOR SEQ ID NO:65:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:65:

Leu Thr Cys Phe Ile Ile Arg Phe Ala
1               5

(2) INFORMATION FOR SEQ ID NO:66:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:66:

Phe Ile Cys Phe Val Ile Arg Phe Ala
1               5

(2) INFORMATION FOR SEQ ID NO:67:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:67:

Phe Val Cys Phe Val Ile Arg Ala Ala
1               5

(2) INFORMATION FOR SEQ ID NO:68:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:68:

Leu Gln Leu Ile Tyr Asn Leu Thr Leu Cys Glu Leu Asn Gly Thr Asp
1               5                   10                  15

Trp Leu (2) INFORMATION FOR SEQ ID NO:69:

(i) SEQUENCE CHARACTERISTICS:

(A) LENGTH: 19 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:69:

CTGCAAGACT CGAACTGAA                                                      19

(2) INFORMATION FOR SEQ ID NO:70:

(i) SEQUENCE CHARACTERISTICS:
        (A) LENGTH: 24 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:70:

GGGGAATTCG GGATAGGGAA TGTG                                                24

(2) INFORMATION FOR SEQ ID NO:71:

(i) SEQUENCE CHARACTERISTICS:
        (A) LENGTH: 26 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:71:

GGGGGATCCT GTTGGTAATA GGTCTG                                              26

(2) INFORMATION FOR SEQ ID NO:72:

(i) SEQUENCE CHARACTERISTICS:
        (A) LENGTH: 26 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:72:

GGGGGATCCT GTTGGTAATA AGTCTG                                              26

(2) INFORMATION FOR SEQ ID NO:73:

(i) SEQUENCE CHARACTERISTICS:
        (A) LENGTH: 28 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:73:

GGTGAATTCG TTTTATTTCC CTCCGGGC                                            28

(2) INFORMATION FOR SEQ ID NO:74:

```
    (i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:74:

GATAGAGTCT GCCCTTAG                                              18

(2) INFORMATION FOR SEQ ID NO:75:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:75:

GGTTTCACCT AGAATGGC                                              18

(2) INFORMATION FOR SEQ ID NO:76:

(i) SEQUENCE CHARACTERISTICS:
        (A) LENGTH: 17 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:76:

GCTTCTGAGA TGAGTGA                                               17

(2) INFORMATION FOR SEQ ID NO:77:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:77:

CAACCAGGCG TAAACACT                                              18

(2) INFORMATION FOR SEQ ID NO:78:

(i) SEQUENCE CHARACTERISTICS:
        (A) LENGTH: 17 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:78:

CTGAGCAATT ACAGAAG                                               17

(2) INFORMATION FOR SEQ ID NO:79:
```

```
    (i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:79:

GACTGATGGT CTGGAAAG                                                    18

(2) INFORMATION FOR SEQ ID NO:80:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:80:

CTGTATCCGA TTCAAACC                                                    18

(2) INFORMATION FOR SEQ ID NO:81:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:81:

AGGTTGGCTG GTGGTCTT                                                    18

(2) INFORMATION FOR SEQ ID NO:82:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:82:

TCGCTCACTA CCTGTTTC                                                    18

(2) INFORMATION FOR SEQ ID NO:83:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:83:

TGTGCCCGCC TTGCCTCA                                                    18
```

```
(2) INFORMATION FOR SEQ ID NO:84:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:84:

AAACCAATTG CCCCCGTC                                                    18

(2) INFORMATION FOR SEQ ID NO:85:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:85:

TATATCACTG TCACAGCC                                                    18

(2) INFORMATION FOR SEQ ID NO:86:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:86:

CAAATTGCCA ACAGAATG                                                    18

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:87:

CAACTTGACG CTATGTGAGC                                                  20

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:88:

GCCGCGGAAC CATCAAGCAC                                                  20
```

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:89:

GACTGCTAGG GCTTCTGCAC                                20

(2) INFORMATION FOR SEQ ID NO:90:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:90:

CGTTGACCGT AGTGGAGC                                  18

(2) INFORMATION FOR SEQ ID NO:91:

(i) SEQUENCE CHARACTERISTICS:
        (A) LENGTH: 22 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:91:

CCCCATTTCC CTCTAGCGAC TG                             22

(2) INFORMATION FOR SEQ ID NO:92:

(i) SEQUENCE CHARACTERISTICS:
        (A) LENGTH: 22 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:92:

CGGCCGTGTG GTTCTCGCCA AT                             22

(2) INFORMATION FOR SEQ ID NO:93:

(i) SEQUENCE CHARACTERISTICS:
        (A) LENGTH: 19 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:93:

GACTGCTTTA CGGTCTCTC                                 19

-continued (2) INFORMATION FOR SEQ ID NO:94:

(i) SEQUENCE CHARACTERISTICS:
        (A) LENGTH: 18 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:94:

GATGCCTGAC ACATTGCC                                     18

(2) INFORMATION FOR SEQ ID NO:95:

(i) SEQUENCE CHARACTERISTICS:
        (A) LENGTH: 19 base pairs
        (B) TYPE: nucleic acid
        (C) STRANDEDNESS: unknown
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:95:

CTGCAAGACT CGAACTGAA                                    19

What is claimed as new and desired to be secured by Letters Patent of the United States is:

1. A composition comprising one or more purified polypeptides encoded by open reading frames (ORF's) 1–7 of a porcine reproductive and respiratory syndrome virus (PRRSV) wherein the virus is characterized as highly virulent as determined by its ability to induce lesions in at least 51.9% of lung tissue 10 days post-inoculation of five-week-old colostrum-deprived, caesarean-derived pigs with $10^5 TCID_{50}$ of said virus.

2. An immunogenic composition comprising (a) an effective amount of the composition of claim 1 to stimulate an immune response in a pig, and (b) a physiological acceptable carrier.

3. A composition comprising one or more purified polypeptides encoded by polynucleotides of a virus of claim 1, wherein the polynucleotides are at least
    (a) 99% identical to ORF 2 of the virus;
    (b) 98% identical to ORF 3 of the virus;
    (c) 98% identical to ORF 4 of the virus; or
    (d) 97% identical to ORF 5 of the virus;
    wherein the identity is determined using the following parameters:
        (i) a cost to open gap of 5;
        (ii) a cost to lengthen a gap of 25;
        (iii) a minimum diagonal length of 4; and
        (iv) a maximum diagonal offset of 10.

4. A composition comprising a purified polypeptide, wherein the polypeptide is at least 97% but less than 100% homologous with the polypeptide encoded by one or both of ORF 6 and ORF 7 of the PRRSV of claim 1 wherein the homology is determined using the following parameters:
    (i) a cost to open gap of 5;
    (ii) a cost to lengthen a gap of 25;
    (iii) a minimum diagonal length of 4; and
    (iv) a maximum diagonal offset of 10.

5. A composition comprising one or more purified polypeptides encoded by open reading frames (ORF's) 1–7 of ISU-51 (VR 2429), ISU-55 (VR 2430), ISU-3927 (VR 2431) and ISU-1894 (VR 2475).

6. An immunogenic composition, comprising (a) an effective amount of the the composition of claim 5 to stimulate a immune response in a pig, and (b) a physiological acceptable carrier.

7. A composition comprising one or more purified polypeptides encoded by polynucleotides of a virus of claim 5 wherein the polynucleotides are at least
    (a) 99% identical to ORF 2 of the virus;
    (b) 98% identical to ORF 3 of the virus;
    (c) 98% identical to ORF 4 of the virus; or
    (d) 97% identical to ORF 5 of the virus;
    wherein the identity is determined using the following parameters:
        (i) a cost to open gap of 5;
        (ii) a cost to lengthen a gap of 25;
        (iii) a minimum diagonal length of 4; and
        (iv) a maximum diagonal offset of 10.

8. A composition comprising at least one parified polypeptide, wherein the polypeptide is at least 97% but less than 100% homologous with the polypeptides encoded by one or both of ORF 6 and ORF 7 of a virus of claim 5 wherein the homology is determined using the following parameters:
    (i) a cost to open gap of 5;
    (ii) a cost to lengthen a gap of 25;
    (iii) a minimum diagonal length of 4; and
    (iv) a maximum diagonal offset of 10.

9. A composition containing at least one purified polypeptide of SEQ ID NOS:45–66.

* * * * *